(12) United States Patent
Li et al.

(10) Patent No.: US 11,440,962 B2
(45) Date of Patent: Sep. 13, 2022

(54) ANTI-CD3EPSILON ANTIBODIES

(71) Applicant: WuXi Biologics Ireland Limited, Dublin (IE)

(72) Inventors: Jing Li, Shanghai (CN); Qin Mei, Shanghai (CN)

(73) Assignee: WUXI BIOLOGICS IRELAND LIMITED, Dublin (IE)

( * ) Notice: Subject to any disclaimer, the term of this patent is extended or adjusted under 35 U.S.C. 154(b) by 285 days.

(21) Appl. No.: 16/649,149

(22) PCT Filed: Sep. 20, 2018

(86) PCT No.: PCT/CN2018/106618
§ 371 (c)(1),
(2) Date: Mar. 20, 2020

(87) PCT Pub. No.: WO2019/057099
PCT Pub. Date: Mar. 28, 2019

(65) Prior Publication Data
US 2020/0299384 A1 Sep. 24, 2020

(30) Foreign Application Priority Data
Sep. 21, 2017 (WO) ................ PCT/CN2017/102622

(51) Int. Cl.
*C07K 16/28* (2006.01)
*A61K 47/68* (2017.01)

(52) U.S. Cl.
CPC ...... *C07K 16/2809* (2013.01); *A61K 47/6803* (2017.08); *C07K 2317/24* (2013.01); *C07K 2317/31* (2013.01); *C07K 2317/33* (2013.01); *C07K 2317/565* (2013.01); *C07K 2317/567* (2013.01); *C07K 2317/77* (2013.01); *C07K 2317/92* (2013.01)

(58) Field of Classification Search
None
See application file for complete search history.

(56) References Cited

U.S. PATENT DOCUMENTS

| 10,865,251 B2 * | 12/2020 | Chen ................. A61P 35/00 |
| 2014/0080147 A1 | 3/2014 | Pass et al. |
| 2017/0204194 A1 | 7/2017 | Chen et al. |

FOREIGN PATENT DOCUMENTS

| WO | 00/41474 A2 | 7/2000 |
| WO | 2007/042261 A2 | 4/2007 |
| WO | 2008/119566 A2 | 10/2008 |
| WO | 2008/119567 A2 | 10/2008 |
| WO | 2015/181098 A1 | 12/2015 |
| WO | 2016/055592 A1 | 4/2016 |

OTHER PUBLICATIONS

Schafhar L et al: "Monoclonal antibody internalization and degradation during modulation of the CD3/T-cell receptor complex", Cellular Immunology, Academic Press, San Diego, CA, US, vol. 116, No. 1, Oct 1, 1988 (Oct 1, 1988), pp. 52-59, XP024005587, ISSN: 0008-8749, DOI: 10.1016/0008-8749(88)90209-2; [retrieved on Oct 1, 1988] abstract.
Partial Supplementary European Search Report (PSESR) for EP18859373.5, dated May 4, 2021.
Yu, X. Z. et al., "Anti-CD3E F(ab') 2 Prevents Graft-Versus-Host Disease by Selectively Depleting Donor T Cells Activated by Recipient Alloantigens", The Journal of Immunology, vol. 166, Dec. 31, 2001 (Dec. 31, 2001), pp. 5835-5839.
The first Examination Report for the corresponding SA application, dated May 30, 2022.

\* cited by examiner

*Primary Examiner* — Meera Natarajan
(74) *Attorney, Agent, or Firm* — Jun He Law Offices P.C.; James J. Zhu

(57) ABSTRACT

The present disclosure provides isolated monoclonal anti-CD3epsilon antibodies or antigen-binding fragments thereof comprising one or more heavy chain CDR sequences selected from the group consisting of: SEQ ID NOs: 1, 3, 5, 7, 9, 11, 13, 15, 17, 19, 21, 23, 25, 27, 29, 31, 33, 35, 37, 39, 41, 43, 45, and 47, and/or one or more kappa light chain CDR sequences selected from the group consisting of: SEQ ID NOs: 2, 4, 6, 8, 10, 12, 14, 16, 18, 20, 22, 24, 26, 28, 30, 32, 34, 36, 38, 40, 42, 44, 46 and 48, isolated polynucleotides encoding the same, pharmaceutical compositions comprising the same, and the use thereof.

19 Claims, 7 Drawing Sheets

Specification includes a Sequence Listing.

ANTI-CD3EPSILON ANTIBODIES

FIELD OF THE INVENTION

The present disclosure generally relates to novel anti-human CD3epsilon antibodies.

BACKGROUND

The CD3 (cluster of differentiation 3) T-cell co-receptor is a protein complex and is composed of four distinct chains, a CD3gamma chain, a CD3delta chain, and two CD3epsilon chains. These chains associate with a molecule known as the T-cell receptor (TCR) and the zeta-chain to generate activation signal in T lymphocytes. The TCR, zeta-chain, and CD3 molecules together comprise the TCR complex, in which TCR as a subunit recognizes and binds to antigen, and CD3 as a subunit transfers and conveys the antigen-stimulation to signaling pathway, and ultimately regulates T-cell activity. The CD3 protein is virtually present in all T cells.

The CD3 together with TCR forms a CD3-TCR complex, which plays pivotal role in modulating T cell vast functions in both innate and adoptive immune response, as well as cellular and humoral immune functions. These include eliminating pathogenic organisms and controlling tumor growth by broad range of cytotoxic effects.

Mouse monoclonal antibodies specific for human CD3, such as OKT3 (Kung et al. (1979) Science 206: 347-9), were the first generation CD3 antibodies for treatment. Although OKT3 has strong immunosuppressive potency, its clinical use was hampered by serious side effects linked to its immunogenic and mitogenic potentials (Chatenoud (2003) Nature Reviews 3:123-132). OKT3 induced an anti-globulin response, promoting its own rapid clearance and neutralization (Chatenoud et al. (1982) Eur. J. Immunol. 137:830-8). In addition, OKT3 induced T-cell proliferation and cytokine production in vitro, and led to a large scale release of cytokine in vivo (Hirsch et al. (1989) J. Immunol 142: 737-43, 1989). The cytokine release (also referred to as "cytokine storm") in turn led to a "flu-like" syndrome, characterized by fever, chills, headaches, nausea, vomiting, diarrhea, respiratory distress, septic meningitis and hypotension (Chatenoud, 2003). Such serious side effects limited the more widespread use of OKT3 in transplantation as well as the extension of its use to other clinical fields such as autoimmunity (Id.).

There is a significant need for novel anti-CD3 antibodies.

BRIEF SUMMARY OF THE INVENTION

Throughout the present disclosure, the articles "a," "an," and "the" are used herein to refer to one or to more than one (i.e., to at least one) of the grammatical object of the article. By way of example, "an antibody" means one antibody or more than one antibody.

The present disclosure provides novel monoclonal anti-CD3epsilon antibodies, amino acid and nucleotide sequences thereof, and uses thereof.

In one aspect, the present disclosure provides isolated antibodies or antigen-binding fragments thereof, comprising 1, 2, or 3 heavy chain CDR sequences selected from the group consisting of: SEQ ID NOs: 1, 3, 5, 7, 9, 11, 13, 15, 17, 19, 21, 23, 25, 27, 29, 31, 33, 35, 37, 39, 41, 43, 45, and 47, and/or 1, 2, or 3 kappa light chain CDR sequences selected from the group consisting of: SEQ ID NOs: 2, 4, 6, 8, 10, 12, 14, 16, 18, 20, 22, 24, 26, 28, 30, 32, 34, 36, 38, 40, 42, 44, 46 and 48.

In certain embodiments, the antibodies or antigen-binding fragments thereof comprise 1, 2, or 3 heavy chain CDR sequences having at least 80% (e.g. at least 85%, 88%, 90%, 91%, 92%, 93%, 94%, 95%, 96%, 97%, 98%, 99%) sequence identity to the sequence of SEQ ID NOs: 1, 3, 5, 7, 9, 11, 13, 15, 17, 19, 21, 23, 25, 27, 29, 31, 33, 35, 37, 39, 41, 43, 45, or 47. In certain embodiments, the antibodies or antigen-binding fragments thereof comprise 1, 2, or 3 light chain CDR sequences having at least 80% (e.g. at least 85%, 88%, 90%, 91%, 92%, 93%, 94%, 95%, 96%, 97%, 98%, 99%) sequence identity to the sequence of SEQ ID NOs: 2, 4, 6, 8, 10, 12, 14, 16, 18, 20, 22, 24, 26, 28, 30, 32, 34, 36, 38, 40, 42, 44, 46 or 48.

In certain embodiments, the antibodies or antigen-binding fragments thereof comprise a heavy chain variable region selected from the group consisting of:
a) a heavy chain variable region comprising 1, 2, or 3 CDR sequences selected from SEQ ID NO: 1, SEQ ID NO: 3, and SEQ ID NO: 5;
b) a heavy chain variable region comprising 1, 2, or 3 CDR sequences selected from SEQ ID NO: 7, SEQ ID NO: 9, and SEQ ID NO: 11;
c) a heavy chain variable region comprising 1, 2, or 3 CDR sequences selected from SEQ ID NO: 13, SEQ ID NO: 15, and SEQ ID NO: 17;
d) a heavy chain variable region comprising 1, 2, or 3 CDR sequences selected from SEQ ID NO: 19, SEQ ID NO: 21, and SEQ ID NO: 23;
e) a heavy chain variable region comprising 1, 2, or 3 CDR sequences selected from SEQ ID NO: 25, SEQ ID NO: 27, and SEQ ID NO: 29;
f) a heavy chain variable region comprising 1, 2, or 3 CDR sequences selected from SEQ ID NO: 31, SEQ ID NO: 33, and SEQ ID NO: 35;
g) a heavy chain variable region comprising 1, 2, or 3 CDR sequences selected from SEQ ID NO: 37, SEQ ID NO: 39, and SEQ ID NO: 41; and
h) a heavy chain variable region comprising 1, 2, or 3 CDR sequences selected from SEQ ID NO: 43, SEQ ID NO: 45, and SEQ ID NO: 47.

In certain embodiments, the antibodies or antigen-binding fragments thereof comprise a kappa light chain variable region selected from the group consisting of:
a) a kappa light chain variable region comprising 1, 2, or 3 CDR sequences selected from SEQ ID NO: 2, SEQ ID NO: 4, and SEQ ID NO: 6;
b) a kappa light chain variable region comprising 1, 2, or 3 CDR sequences selected from SEQ ID NO: 8, SEQ ID NO: 10, and SEQ ID NO: 12;
c) a kappa light chain variable region comprising 1, 2, or 3 CDR sequences selected from SEQ ID NO: 14, SEQ ID NO: 16 and/or SEQ ID NO: 18;
d) a kappa light chain variable region comprising 1, 2, or 3 CDR sequences selected from SEQ ID NO: 20, SEQ ID NO: 22, and SEQ ID NO: 24;
e) a kappa light chain variable region comprising 1, 2, or 3 CDR sequences selected from SEQ ID NO: 26, SEQ ID NO: 28, and SEQ ID NO: 30;
f) a kappa light chain variable region comprising 1, 2, or 3 CDR sequences selected from SEQ ID NO: 32, SEQ ID NO: 34, and SEQ ID NO: 36;
g) a kappa light chain variable region comprising 1, 2, or 3 CDR sequences selected from SEQ ID NO: 38, SEQ ID NO: 40, and SEQ ID NO: 42; and
h) a kappa light chain variable region comprising 1, 2, or 3 CDR sequences selected from SEQ ID NO: 44, SEQ ID NO: 46, and SEQ ID NO: 48.

In certain embodiments, the antibodies or antigen-binding fragments thereof comprise a heavy chain CDR3 sequence selected from the group consisting of SEQ ID NOs: 5, 11, 17, 23, 29, 35, 41, and 47.

In certain embodiments, the antibodies or antigen-binding fragments thereof comprise:
- a) a heavy chain CDR1 sequence selected from SEQ ID NO: 1, SEQ ID NO: 7, SEQ ID NO: 13, SEQ ID NO: 19, SEQ ID NO: 25, SEQ ID NO: 31, SEQ ID NO: 37, and SEQ ID NO: 43;
- b) a heavy chain CDR2 sequence selected from SEQ ID NO: 3, SEQ ID NO: 9, SEQ ID NO: 15, SEQ ID NO: 21, SEQ ID NO: 27, SEQ ID NO: 33, SEQ ID NO: 39, and SEQ ID NO: 45; and
- c) a heavy chain CDR3 sequence selected from SEQ ID NO: 5, SEQ ID NO: 11, SEQ ID NO: 17, SEQ ID NO: 23, SEQ ID NO: 29, SEQ ID NO: 35, SEQ ID NO: 41, and SEQ ID NO: 47.

In certain embodiments, the antibodies or antigen-binding fragments thereof comprise:
- a) a light chain CDR1 sequence selected from SEQ ID NO: 2, SEQ ID NO: 8, SEQ ID NO: 14, SEQ ID NO: 20, SEQ ID NO: 26, SEQ ID NO: 32, SEQ ID NO: 38, and SEQ ID NO: 44;
- b) a light chain CDR2 sequence selected from SEQ ID NO: 4, SEQ ID NO: 10, SEQ ID NO: 16, SEQ ID NO: 22, SEQ ID NO: 28, SEQ ID NO: 34, SEQ ID NO: 40, and SEQ ID NO: 46; and
- c) a light chain CDR3 sequence selected from SEQ ID NO: 6, SEQ ID NO: 12, SEQ ID NO: 18, SEQ ID NO: 24, SEQ ID NO: 30. SEQ ID NO: 36, SEQ ID NO: 42, and SEQ ID NO: 48.

In certain embodiments, the antibodies or antigen-binding fragments thereof comprises:
- a) a heavy chain CDR1 sequence selected from SEQ ID NO: 1, SEQ ID NO: 7, SEQ ID NO: 13, SEQ ID NO: 19, SEQ ID NO: 25, SEQ ID NO: 31, SEQ ID NO: 37, and SEQ ID NO: 43;
- b) a heavy chain CDR2 sequence selected from SEQ ID NO: 3, SEQ ID NO: 9, SEQ ID NO: 15, SEQ ID NO: 21, SEQ ID NO: 27, SEQ ID NO: 33, SEQ ID NO: 39, and SEQ ID NO: 45;
- c) a heavy chain CDR3 sequence selected from SEQ ID NO: 5, SEQ ID NO: 11, SEQ ID NO: 17, SEQ ID NO: 23, SEQ ID NO: 29, SEQ ID NO: 35, SEQ ID NO: 41, and SEQ ID NO: 47;
- d) a light chain CDR1 sequence selected from SEQ ID NO: 2, SEQ ID NO: 8, SEQ ID NO: 14, SEQ ID NO: 20, SEQ ID NO: 26, SEQ ID NO: 32, SEQ ID NO: 38, and SEQ ID NO: 44;
- e) a light chain CDR2 sequence selected from SEQ ID NO: 4, SEQ ID NO: 10, SEQ ID NO: 16, SEQ ID NO: 22, SEQ ID NO: 28, SEQ ID NO: 34, SEQ ID NO: 40, and SEQ ID NO: 46; and
- f) a light chain CDR3 sequence selected from SEQ ID NO: 6, SEQ ID NO: 12, SEQ ID NO: 18, SEQ ID NO: 24, SEQ ID NO: 30, SEQ ID NO: 36, SEQ ID NO: 42, and SEQ ID NO: 48.

In certain embodiments, the antibodies or antigen-binding fragments thereof comprises:
- a) a heavy chain variable region comprising 1, 2, or 3 CDR sequences selected from SEQ ID NO: 1, SEQ ID NO: 3, and SEQ ID NO: 5; and a kappa light chain variable region comprising 1, 2, or 3 CDR sequences selected from SEQ ID NO: 2, SEQ ID NO: 4, and SEQ ID NO: 6;
- b) a heavy chain variable region comprising 1, 2, or 3 CDR sequences selected from SEQ ID NO: 7, SEQ ID NO: 9, and SEQ ID NO: 11; and a kappa light chain variable region comprising 1, 2, or 3 CDR sequences selected from SEQ ID NO: 8, SEQ ID NO: 10, and SEQ ID NO: 12;
- c) a heavy chain variable region comprising 1, 2, or 3 CDR sequences selected from SEQ ID NO: 13, SEQ ID NO: 15, and SEQ ID NO: 17; and a kappa light chain variable region comprising 1, 2, or 3 CDR sequences selected from SEQ ID NO: 14, SEQ ID NO: 16, and SEQ ID NO: 18;
- d) a heavy chain variable region comprising 1, 2, or 3 CDR sequences selected from SEQ ID NO: 19, SEQ ID NO: 21, and SEQ ID NO: 23; and a kappa light chain variable region comprising 1, 2, or 3 CDR sequences selected from SEQ ID NO: 20, SEQ ID NO: 22, and SEQ ID NO: 24;
- e) a heavy chain variable region comprising 1, 2, or 3 CDR sequences selected from SEQ ID NO: 25, SEQ ID NO: 27, and SEQ ID NO: 29; and a kappa light chain variable region comprising 1, 2, or 3 CDR sequences selected from SEQ ID NO: 26, SEQ ID NO: 28, and SEQ ID NO: 30;
- f) a heavy chain variable region comprising 1, 2, or 3 CDR sequences selected from SEQ ID NO: 31, SEQ ID NO: 33, and SEQ ID NO: 35; and a kappa light chain variable region comprising 1, 2, or 3 CDR sequences selected from SEQ ID NO: 32, SEQ ID NO: 34, and SEQ ID NO: 36;
- g) a heavy chain variable region comprising 1, 2, or 3 CDR sequences selected from SEQ ID NO: 37, SEQ ID NO: 39, and SEQ ID NO: 41; and a kappa light chain variable region comprising 1, 2, or 3 CDR sequences selected from SEQ ID NO: 38, SEQ ID NO: 40, and SEQ ID NO: 42; or
- h) a heavy chain variable region comprising 1, 2, or 3 CDR sequences selected from SEQ ID NO: 43, SEQ ID NO: 45, and SEQ ID NO: 47; and a kappa light chain variable region comprising 1, 2, or 3 CDR sequences selected from SEQ ID NO: 44, SEQ ID NO: 46, and SEQ ID NO: 48.

In certain embodiments, the antibodies or antigen-binding fragments thereof further comprises 1, 2, 3 or 4 heavy chain framework region (FR) sequences selected from the group consisting of: SEQ ID NO: 57, 59, 61, 63, 73, 75, 77 and 79, and/or 1, 2, 3, or 4 light chain framework region (FR) sequences selected from SEQ ID NO: 58, 60, 62, 64, 74, 76, 78 and 80.

In certain embodiments, the antibodies or antigen-binding fragments thereof further comprises heavy chain FR1 sequence selected from SEQ ID NO: 57 and 73; heavy chain FR2 sequence selected from SEQ ID NO: 59 and 75; heavy chain FR3 sequence selected from SEQ ID NO: 61 and 77; and heavy chain FR4 sequence selected from SEQ ID NO: 63 and 79.

In certain embodiments, the antibodies or antigen-binding fragments thereof further comprises light chain FR1 sequence selected from SEQ ID NO: 58 and 74; light chain FR2 sequence selected from SEQ ID NO: 60 and 76; light chain FR3 sequence selected from SEQ ID NO: 62 and 78; and light chain FR4 sequence selected from SEQ ID NO: 64 and 80.

In certain embodiments, the antibodies or antigen-binding fragments thereof comprises a heavy chain variable region selected from the group consisting of: SEQ ID NO: 81, SEQ ID NO: 85, SEQ ID NO: 89, SEQ ID NO: 93, SEQ ID NO:

97, SEQ ID NO: 101, SEQ ID NO: 105, SEQ ID NO: 109, SEQ ID NO: 113, SEQ ID NO: 117 and a homologous sequence thereof having at least 80% (e.g. at least 85%, 88%, 90%, 91%, 92%, 93%, 94%, 95%, 96%, 97%, 98% or 99%) sequence identity.

In certain embodiments, the antibodies or antigen-binding fragments thereof comprises a light chain variable region selected from the group consisting of: SEQ ID NO: 83, SEQ ID NO: 87, SEQ ID NO: 91, SEQ ID NO: 95, SEQ ID NO: 99, SEQ ID NO: 103, SEQ ID NO: 107, SEQ ID NO: 111, SEQ ID NO: 115, SEQ ID NO: 119 and a homologous sequence thereof having at least 80% (e.g. at least 85%, 88%, 90%, 91%, 92%, 93%, 94%, 95%, 96%, 97%, 98% or 99%) sequence identity.

In some embodiments, the antibodies or antigen-binding fragments thereof comprises all or a portion of the heavy chain variable region sequence selected from the group consisting of: SEQ ID NO: 81, 85, 89, 93, 97, 101, 105, 109, 113, and 117; and/or, all or a portion of the light chain variable region sequence selected from the group consisting of: SEQ ID NO: 83, 87, 91, 95, 99, 103, 107, 111, 115, and 119. In one embodiment, the antibodies or antigen-binding fragments thereof is a single domain antibody which consists of all or a portion of the heavy chain variable region selected from the group consisting of: SEQ ID NO: 81, 85, 89, 93, 97, 101, 105, 109, 113, and 117.

In certain embodiments, the antibodies or antigen-binding fragments thereof comprises:
a) a heavy chain variable region comprising SEQ ID NO: 81 and a kappa light chain variable region comprising SEQ ID NO: 83;
b) a heavy chain variable region comprising SEQ ID NO: 85 and a kappa light chain variable region comprising SEQ ID NO: 87;
c) a heavy chain variable region comprising SEQ ID NO: 89 and a kappa light chain variable region comprising SEQ ID NO: 91;
d) a heavy chain variable region comprising SEQ ID NO: 93 and a kappa light chain variable region comprising SEQ ID NO: 95;
e) a heavy chain variable region comprising SEQ ID NO: 97 and a kappa light chain variable region comprising SEQ ID NO: 99;
f) a heavy chain variable region comprising SEQ ID NO: 101 and a kappa light chain variable region comprising SEQ ID NO: 103;
g) a heavy chain variable region comprising SEQ ID NO: 105 and a kappa light chain variable region comprising SEQ ID NO: 107;
h) a heavy chain variable region comprising SEQ ID NO: 109 and a kappa light chain variable region comprising SEQ ID NO: 111;
i) a heavy chain variable region comprising SEQ ID NO: 113 and a kappa light chain variable region comprising SEQ ID NO: 115; or
j) a heavy chain variable region comprising SEQ ID NO: 117 and a kappa light chain variable region comprising SEQ ID NO: 119.

In certain embodiments, the antibody or antigen-binding fragment thereof comprises one or more amino acid residue substitutions yet retains specific binding affinity to CD3epsilon.

In certain embodiments, the substitution is in one or more CDR sequences, or in one or more FR sequences, or in one or both variable region sequences, or in Fc region. In some embodiments, at least one (or all) of the substitution(s) in the CDR sequences, FR sequences, variable region sequences or Fc region comprises a conservative substitution.

In certain embodiments, the antibody or antigen-binding fragment thereof comprises no more than 10, 9, 8, 7, 6, 5, 4, 3, 2, or 1 amino acid residue substitutions in one or more CDR sequences selected from SEQ ID NO: 1-48. In certain embodiments, the antibody or antigen-binding fragment thereof comprises no more than 10, 9, 8, 7, 6, 5, 4, 3, 2, or 1 amino acid residue substitutions in one or more FR sequences selected from SEQ ID NO: 57-80. In certain embodiments, the antibody or antigen-binding fragment thereof comprises no more than 10, 9, 8, 7, 6, 5, 4, 3, 2, or 1 substitutions in total in CDR sequences and/or FR sequences of a heavy chain variable region sequences selected from SEQ ID NO: 81, 85, 89, 93, 97, 101, 105, 109, 113, and 117. In certain embodiments, the antibody or antigen-binding fragment thereof comprises no more than 10, 9, 8, 7, 6, 5, 4, 3, 2, or 1 amino acid residue substitutions in all the FRs of a light chain variable region sequences selected from SEQ ID NO: 83, 87, 91, 95, 99, 103, 107, 111, 115, and 119.

In certain embodiments, the substitution confers one or more desirable properties selected from: a) improving binding affinity to CD3epsilon, b) introducing or removing a glycosylation site, c) introducing a free cysteine residue, d) enhancing or reducing ADCC or CDC, e) increasing serum half-life; and f) increasing FcRn binding.

In certain embodiments, the antibody or antigen-binding fragment thereof further comprises an immunoglobulin constant region. In certain embodiments, the antibody or antigen-binding fragment thereof comprises a constant region of IgG. In certain embodiment, the antibody or antigen-binding fragment thereof comprises a constant region of human IgG1.

In certain embodiments, the antibodies or antigen-binding fragments thereof is a murine antibody or a humanized antibody.

In certain embodiments, the antibodies or antigen-binding fragments thereof are a camelized single domain antibody, a diabody, a scFv, an scFv dimer, a BsFv, a dsFv, a (dsFv)2, a dsFv-dsFv', an Fv fragment, a Fab, a Fab', a F(ab')2, a bispecific antibody, a ds diabody, a nanobody, a domain antibody, or a bivalent domain antibody.

In certain embodiments, the antibodies or antigen-binding fragments thereof is bispecific. In certain embodiments, the antibody or an antigen-binding fragment thereof has a first antigenic specificity for CD3epsilon, and a second antigenic specificity. In certain embodiments, the second antigenicity is for a second antigen different from CD3epsilon, wherein presence of the second antigen in proximity to a CD3epsilon-expressing T cells is desirable for the second antigen to be recognized by immune system. In certain embodiments, the first antigenic specificity is for CD3epsilon, and the second antigenic specificity is for a tumor associated antigen.

In certain embodiments, the antibodies or antigen-binding fragments thereof is linked to one or more conjugates. In certain embodiments, the conjugate can be a chemotherapeutic agent, a toxin, a radioactive isotope, a lanthanide, a luminescent label, a fluorescent label, or an enzyme-substrate label.

In certain embodiments, the antibody or an antigen-binding fragment thereof is capable of specifically binding to CD3epsilon. In certain embodiments, the CD3epsilon are derived from mouse, rat, monkey or human. In certain embodiments, the CD3epsilon is a recombinant CD3epsilon or a CD3epsilon expressed on a cell surface.

In certain embodiments, the antibodies or antigen-binding fragments thereof is capable of specifically binding to human CD3epsilon expressed on a cell surface at a $K_D$ value of no more than $5×10^{-9}$M, no more than $4×10^{-9}$M, no more than $3×10^{-9}$M, no more than $2×10^{-9}$M, no more than $10^{-9}$M, no more than $5×10^{-10}$M, no more than $4×10^{-10}$, no more than $3×10^{-10}$M, no more than $2×10^{-10}$M, no more than $10^{-10}$M, no more than $5×10^{-11}$ M, no more than $4×10^{-11}$ M, no more than $3×10^{-11}$ M, no more than $2×10^{-11}$ M, or no more than $10^{-11}$ M as measured by flow cytometry assay. In certain embodiments, the antibodies or antigen-binding fragments thereof is capable of specifically binding to human CD3epsilon expressed on surface of cells at an $EC_{50}$ of no more than 0.50 nM, or no more than 1.10 nM by flow cytometry assay.

In certain embodiments, the antibodies or antigen-binding fragments thereof is capable of specifically binding to recombinant Cynomolgus monkey CD3epsilon with an $EC_{50}$ of no more than 0.001 nM, no more than 0.005 nM, no more than 0.01 nM, no more than 0.02 nM, no more than 0.03 nM, no more than 0.04 nM, or no more than 0.05 nM as measured by ELISA.

In certain embodiments, the antibodies or antigen-binding fragments thereof is capable of specifically binding to recombinant human CD3epsilon at an $EC_{50}$ of no more than 0.01 nM, no more than 0.02 nM, no more than 0.03 nM, no more than 0.04 nM, no more than 0.05 nM, no more than 0.06 nM, no more than 0.07 nM or no more than 0.08 nM as measured by ELISA.

In certain embodiments, the antibodies or antigen-binding fragments thereof is capable of specifically binding to human CD3epsilon expressed on a CD3-expressing cell surface at an $EC_{50}$ of no more than 0.5 nM, no more than 0.6 nM, no more than 0.7 nM, no more than 0.8 nM, no more than 0.9 nM, no more than 1 nM, no more than 2 nM, no more than 3 nM, no more than 4 nM, no more than 5 nM, no more than 6 nM, no more than 7 nM, no more than 8 nM, no more than 9 nM or no more than 10 nM as measured by flow cytometry assay.

In certain embodiments, the antibodies or antigen-binding fragments thereof is a humanized antibody, which is capable of specifically binding to human CD3epsilon expressed on a CD4-expressing cell surface at an $EC_{50}$ of no more than 0.50 nM, or no more than 1.10 nM as measured by flow cytometry assay.

In one aspect, the present disclosure provides an antibody or an antigen-binding fragment thereof, which competes for the same epitope with the antibody or antigen-binding fragment thereof provided herein.

In one aspect, the present disclosure further provides a pharmaceutical composition comprising the antibody or antigen-binding fragment thereof provided herein and a pharmaceutically acceptable carrier. In certain embodiments, the pharmaceutical composition further comprises a second agent which is capable of enhancing a therapeutic effect of the antibody or antigen-binding fragment thereof and/or is capable of reducing a side effect of the antibody or antigen-binding fragment thereof.

In one aspect, the present disclosure further provides an isolated polynucleotide encoding the antibody or an antigen-binding fragment thereof provided herein. In certain embodiments, the isolated polynucleotide comprises a nucleotide sequence selecting from a group consisting of SEQ ID NO: 82, 84, 86, 88, 90, 92, 94, 96, 98, 100, 102, 104, 106, 108, 110, 112, 114, 116, 118 and 120.

In one aspect, the present disclosure further provides a vector comprising said isolated polynucleotide.

In one aspect, the present disclosure further provides a host cell comprising said vector.

In one aspect, the present disclosure further provides a method of expressing the antibody or antigen-binding fragment thereof provided herein, comprising culturing said host cell under the condition at which said polynucleotide is expressed.

In one aspect, the present disclosure further provides a method of treating a disease or condition in a subject that would benefit from modulation of CD3epsilon activity, comprising administering to the subject a therapeutically effective amount of the antibody or antigen-binding fragment thereof provided herein or the pharmaceutical composition provided herein. In certain embodiments, said subject is human. In certain embodiments, said disease or condition is a CD3 related disease or condition. In certain embodiments, said disease or condition is cancer, autoimmune disease, inflammatory disease, or infectious disease.

In one aspect, the present disclosure further provides a method of activating CD3epsilon-expressing T cells in vivo or in vitro, comprising contacting the CD3epsilon-expressing T cells with the antibody or antigen-binding fragment thereof provided herein.

In one aspect, the present disclosure further provides a method of modulating CD3 activity in a CD3epsilon-expressing cell, comprising exposing the CD3epsilon-expressing cell to the antibody or antigen-binding fragment thereof provided herein.

In one aspect, the present disclosure further provides a method of promoting in vivo or in vitro processing of a second antigen by CD3epsilon-expressing T cells, comprising contacting the CD3epsilon-expressing T cells with a bispecific antibody or antigen-binding fragment thereof provided herein, wherein the bispecific antibody or antigen-binding fragment is capable of specifically binding to both the CD3epsilon-expressing T cells and a second antigen thereby bringing both in close proximity.

In one aspect, the present disclosure further provides a method of detecting presence or amount of CD3epsilon in a sample, comprising contacting the sample with the antibody or antigen-binding fragment thereof provided herein, and determining the presence or the amount of CD3epsilon in the sample.

In one aspect, the present disclosure further provides a method of diagnosing a CD3 related disease or condition in a subject, comprising: a) obtaining a sample from the subject; b) contacting the sample with the antibodies or antigen-binding fragments thereof provided herein; c) determining presence or amount of CD3epsilon in the sample; and d) correlating the presence or the amount of CD3epsilon to a disease or condition in the subject.

In one aspect, the present disclosure further provides use of the antibody or antigen-binding fragment thereof provided herein in the manufacture of a medicament for treating a CD3 related disease or condition in a subject.

In one aspect, the present disclosure further provides use of the antibody or antigen-binding fragment thereof provided herein in the manufacture of a diagnostic reagent for diagnosing a CD3 related disease or condition.

In one aspect, the present disclosure further provides a kit comprising the antibody or antigen-binding fragment thereof provided herein, useful in detecting CD3epsilon. In certain embodiments, the kit comprises antibodies or antigen-binding fragment thereof useful in detecting recombinant CD3epsilon, CD3epsilon expressed on cell surface, or CD3epsilon-expressing cells.

DETAILED DESCRIPTION OF THE INVENTION

Figure 1:
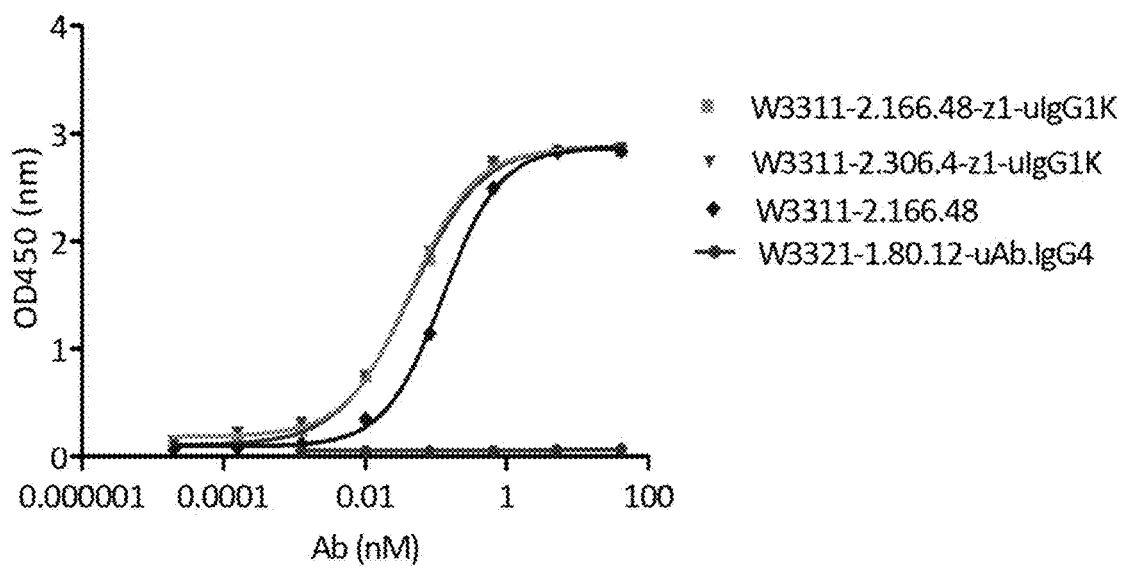
FIG. 1 shows binding of the monoclonal antibodies. WBP3311_2.166.48-uIgG1K, WBP3311_2.306.4-uIgG1K, and WBP3311_2.166.48, to recombinant Cynomolgus Monkey CD3epsilon protein as measured by ELISA assay.

The following description of the disclosure is merely intended to illustrate various embodiments of the disclosure. As such, the specific modifications discussed are not to be construed as limitations on the scope of the disclosure. It will be apparent to one skilled in the art that various equivalents, changes, and modifications may be made without departing from the scope of the disclosure, and it is understood that such equivalent embodiments are to be included herein. All references cited herein, including publications, patents and patent applications are incorporated herein by reference in their entirety.

Definitions

The term "antibody" as used herein includes any immunoglobulin, monoclonal antibody, polyclonal antibody, multivalent antibody, bivalent antibody, monovalent antibody, multispecific antibody, or bispecific antibody that binds to a specific antigen. A native intact antibody comprises two heavy (H) chains and two light (L) chains. Mammalian heavy chains are classified as alpha, delta, epsilon, gamma, and mu, each heavy chain consists of a variable region ($V_H$) and a first, second, and third constant region ($C_{H1}$, $C_{H2}$, $C_{H3}$, respectively); mammalian light chains are classified as λ or κ, while each light chain consists of a variable region ($V_L$ for λ light chain or $V_K$ for κlight chain, respectively) and a constant region($C_L$ for λ light chain or $C_K$ for κlight chain, respectively). The antibody has a "Y" shape, with the stem of the Y consisting of the second and third constant regions of two heavy chains bound together via disulfide bonding. Each arm of the Y includes the variable region and first constant region of a single heavy chain bound to the variable and constant regions of a single light chain. The variable regions of the light and heavy chains are responsible for antigen binding. The variable regions in both chains generally contain three highly variable loops called the complementarity determining regions (CDRs) (light chain CDRs including LCDR1, LCDR2, and LCDR3, heavy chain CDRs including HCDR1, HCDR2, HCDR3). CDR boundaries for the antibodies and antigen-binding fragments disclosed herein may be defined or identified by the conventions of Kabat, IMGT, Chothia, or Al-Lazikani (Al-Lazikani, B., Chothia, C., Lesk, A. M., J. Mol. Biol., 273(4), 927 (1997); Chothia, C. et al., J Mol Biol. December 5; 186(3):651-63 (1985); Chothia, C. and Lesk, A. M., J.Mol.Biol., 196,901 (1987); Chothia, C. et al., Nature. December 21-28; 342 (6252):877-83 (1989); Kabat E. A. et al., National Institutes of Health, Bethesda, Md. (1991)). The three CDRs are interposed between flanking stretches known as framework regions (FRs), which are more highly conserved than the CDRs and form a scaffold to support the hypervariable loops. The constant regions of the heavy and light chains are not involved in antigen-binding, but exhibit various effector functions. Antibodies are assigned to classes based on the amino acid sequence of the constant region of their heavy chain. The five major classes or isotypes of antibodies are IgA, IgD, IgE, IgG, and IgM, which are characterized by the presence of alpha, delta, epsilon, gamma, and mu heavy chains, respectively. Several of the major antibody classes are divided into subclasses such as IgG1 (gamma1 heavy chain), IgG2 (gamma2 heavy chain), IgG3 (gamma3 heavy chain), IgG4 (gamma4 heavy chain), IgA1 (alpha1 heavy chain), or IgA2 (alpha2 heavy chain).

The term "bivalent" as used herein refers to an antibody or an antigen-binding fragment having two antigen-binding sites; the term "monovalent" refers to an antibody or an antigen-binding fragment having only one single antigen-binding site; and the term "multivalent" refers to an antibody or an antigen-binding fragment having multiple antigen-binding sites. In some embodiments, the antibody or antigen-binding fragment thereof is bivalent.

As used herein, a "bispecific" antibody refers to an artificial antibody which has fragments derived from two different monoclonal antibodies and is capable of binding to two different epitopes. The two epitopes may present on the same antigen, or they may present on two different antigens.

The term "antigen-binding fragment" as used herein refers to an antibody fragment formed from a portion of an antibody comprising 1, 2 or 3 CDRs, or any other antibody fragment that binds to an antigen but does not comprise an intact native antibody structure. Examples of antigen-binding fragment include, without limitation, a diabody, a Fab, a Fab', a F(ab')$_2$, an Fv fragment, a disulfide stabilized Fv fragment (dsFv), a (dsFv)$_2$, a bispecific dsFv (dsFv-dsFv'), a disulfide stabilized diabody (ds diabody), a single-chain antibody molecule (scFv), an scFv dimer (bivalent diabody), a bispecific antibody, a multispecific antibody, a camelized single domain antibody, a nanobody, a domain antibody, and a bivalent domain antibody. An antigen-binding fragment is capable of binding to the same antigen to which the parent antibody binds.

"Fab" with regard to an antibody refers to that portion of the antibody consisting of a single light chain (both variable and constant regions) bound to the variable region and first constant region of a single heavy chain by a disulfide bond.

"Fab'" refers to a Fab fragment that includes a portion of the hinge region.

"F(ab')$_2$" refers to a dimer of Fab'. "Fv" with regard to an antibody refers to the smallest fragment of the antibody to bear the complete antigen-binding site. An Fv fragment consists of the variable region of a single light chain bound to the variable region of a single heavy chain.

A "dsFv" refers to a disulfide-stabilized Fv fragment that the linkage between the variable region of a single light chain and the variable region of a single heavy chain is a disulfide bond. In some embodiments, a "(dsFv)$_2$" or "(dsFv-dsFv')" comprises three peptide chains: two $V_H$ moieties linked by a peptide linker (e.g., a long flexible linker) and bound to two $V_L$ moieties, respectively, via disulfide bridges. In some embodiments, dsFv-dsFv' is bispecific in which each disulfide paired heavy and light chain has a different antigen specificity.

"Single-chain Fv antibody" or "scFv" refers to an engineered antibody consisting of a light chain variable region and a heavy chain variable region connected to one another directly or via a peptide linker sequence (Huston J S et al. Proc Natl Acad Sci USA, 85:5879(1988)).

"Fc" with regard to an antibody refers to that portion of the antibody consisting of the second and third constant regions of a first heavy chain bound to the second and third constant regions of a second heavy chain via disulfide bonding. The Fc portion of the antibody is responsible for various effector functions such as antibody-dependent cell-mediated cytotoxicity (ADCC), and complement dependent cytotoxicity (CDC), but does not function in antigen binding.

"Single-chain Fv-Fc antibody" or "scFv-Fc" refers to an engineered antibody consisting of a scFv connected to the Fc region of an antibody.

"Camelized single domain antibody," "heavy chain antibody," or "HCAb" refers to an antibody that contains two $V_H$ domains and no light chains (Riechmann L. and Muyldermans S., J Immunol Methods. December 10; 231(1-2): 25-38 (1999); Muyldermans S., J Biotechnol. June; 74(4): 277-302 (2001); WO94/04678: WO94/25591; U.S. Pat. No. 6,005,079). Heavy chain antibodies were originally derived from *Camelidae* (camels, dromedaries, and llamas). Although devoid of light chains, camelized antibodies have an authentic antigen-binding repertoire (Hamers-Casterman C. et al., Nature. June 3; 363(6428):446-8 (1993); Nguyen V K. et al. "Heavy-chain antibodies in *Camelidae*; a case of evolutionary innovation," Immunogenetics. April; 54(1):39-47 (2002); Nguyen V K. et al. Immunology. May; 109(1): 93-101 (2003)). The variable domain of a heavy chain antibody (VHH domain) represents the smallest known antigen-binding unit generated by adaptive immune responses (Koch-Nolte F. et al., FASEB J. November; 21(13):3490-8. Epub 2007 Jun. 15 (2007)).

A "nanobody" refers to an antibody fragment that consists of a VHH domain from a heavy chain antibody and two constant domains, CH2 and CH3.

"Diabodies" or "dAbs" include small antibody fragments with two antigen-binding sites, wherein the fragments comprise a $V_H$ domain connected to a $V_L$ domain in the same polypeptide chain ($V_H$-$V_L$ or $V_L$-$V_H$) (see, e.g., Holliger P. et al., Proc Natl Acad Sci USA. July 15; 90(14):6444-8 (1993); EP404097; WO93/11161). By using a linker that is too short to allow pairing between the two domains on the same chain, the domains are forced to pair with the complementary domains of another chain, thereby creating two antigen-binding sites. The antigen-binding sites may target the same or different antigens (or epitopes). In certain embodiments, a "bispecific ds diabody" is a diabody target two different antigens (or epitopes). In certain embodiments, an "scFv dimer" is a bivalent diabody or bivalent ScFv (BsFv) comprising $V_H$—$V_L$ (linked by a peptide linker) dimerized with another $V_H$-$V_L$ moiety such that $V_H$'s of one moiety coordinate with the $V_L$'s of the other moiety and form two binding sites which can target the same antigens (or eptipoes) or different antigens (or eptipoes). In other embodiments, an "scFv dimer" is a bispecific diabody comprising $V_{H1}$-$V_{L2}$ (linked by a peptide linker) associated with $V_{L1}$-$V_{H2}$ (also linked by a peptide linker) such that $V_{H1}$ and $V_{L1}$ coordinate and $V_{H2}$ and $V_{L2}$ coordinate and each coordinated pair has a different antigen specificity.

A "domain antibody" refers to an antibody fragment containing only the variable region of a heavy chain or the variable region of a light chain. In certain instances, two or more $V_H$ domains are covalently joined with a peptide linker to create a bivalent or multivalent domain antibody. The two $V_H$ domains of a bivalent domain antibody may target the same or different antigens.

The term "chimeric" as used herein, means an antibody or antigen-binding fragment, having a portion of heavy and/or light chain derived from one species, and the rest of the heavy and/or light chain derived from a different species. In an illustrative example, a chimeric antibody may comprise a constant region derived from human and a variable region from a non-human animal, such as from mouse. In some embodiments, the non-human animal is a mammal, for example, a mouse, a rat, a rabbit, a goat, a sheep, a guinea pig, or a hamster.

The term "humanized" as used herein means that the antibody or antigen-binding fragment comprises CDRs derived from non-human animals, FR regions derived from human, and when applicable, the constant regions derived from human.

"CD3" as used herein, refers to the Cluster of Differentiation 3 protein derived from any vertebrate source, including mammals such as primates (e.g. humans, monkeys) and rodents (e.g., mice and rats). In mammals, the CD3 molecule is a multi-protein complex of six chains, including: a CD3gamma chain, a CD3delta chain, two CD3epsilon chains, and a homodimer of CD3zeta chains, wherein the CD3zeta chain is the intracellular tail of CD3 molecule, and the CD3gamma, CD3delta and CD3epsilon chains all contain extracellular domain (ECD) expressed on surface of T cells. Exemplary sequence of human CD3 includes human CD3epsilon protein (NCBI Ref Seq No. NP_000724), human CD3 delta protein (NCBI Ref Seq No. NP_000723), and human CD3gamma protein (NCBI Ref Seq No. NP_000064). Exemplary sequence of non-human CD3 includes *Macaca fascicularis* (monkey) CD3epsilon protein (NCBI Ref Seq No. NP_001270544), *Macaca fascicularis* (monkey) CD3delta protein (NCBI Ref Seq No. NP_001274617), *Macaca fascicularis* (monkey) CD3gamma protein (NCBI Ref Seq No. NP_001270839); mouse CD3epsilon protein (NCBI Ref Seq No. NP_031674), mouse CD3delta protein (NCBI Ref Seq No. NP_038515), mouse CD3gamma protein (NCBI Ref Seq No. AAA37400); *Rattus norvegicus* (Rat) CD3epsilon protein (NCBI Ref Seq No. NP_001101610), *Rattus norvegicus* (Rat) CD3delta protein (NCBI Ref Seq No. NP_037301), *Rattus norvegicus* (Rat) CD3gamma protein (NCBI Ref Seq No. NP_001071114). In certain embodiments, CD3 used herein can also be recombinant CD3, for example, including recombinant CD3epsilon protein, recombinant CD3delta protein, and recombinant CD3gamma protein, which may optionally be expressed as a recombinant CD3 complex. The recombinant CD3 complex may be expressed on a cell surface, or alternatively may be expressed as a soluble form which is not associated on a cell surface.

The term "CD3epsilon" as used herein is intended to encompass any form of CD3epsilon, for example, 1) native unprocessed CD3epsilon molecule, "full-length" CD3epsilon chain or naturally occurring variants of CD3epsilon, including, for example, splice variants or allelic variants; 2) any form of CD3epsilon that results from processing in the cell; or 3) full length, a fragment (e.g., a truncated form, an extracellular/transmembrane domain) or a modified form (e.g. a mutated form, a glycosylated/PEGylated, a His-tag/immunofluorescence fused form) of CD3epsilon subunit generated through recombinant method.

The term "anti-CD3epsilon antibody" refers to an antibody that is capable of specific binding CD3epsilon (e.g. human or monkey CD3epsilon).

The term "specific binding" or "specifically binds" as used herein refers to a non-random binding reaction between two molecules, such as for example between an antibody and an antigen. In certain embodiments, the antibodies or antigen-binding fragments provided herein specifically bind to human and/or CD3epsilon with a binding affinity ($K_D$) of $\leq 10^{-6}$ M (e.g., $\leq 5\times 10^{-7}$ M, $\leq 2\times 10^{-7}$ M, $\leq 10^{-7}$ M, $\leq 5\times 10^{-8}$ M, $\leq 2\times 10^{-8}$ M, $\leq 10^{-8}$ M, $\leq 5\times 10^{-9}$ M, $\leq 4\times 10^{-9}$M, $\leq 3\times 10^{-9}$ M, $\leq 2\times 10^{-9}$ M, or $\leq 10^{-9}$ M). $K_D$ used herein refers to the ratio of the dissociation rate to the association rate ($k_{off}/k_{on}$), which may be determined by using any conventional method known in the art, including but are not limited to surface plasmon resonance method, microscale thermophoresis method, HPLC-MS method and flow cytometry (such as FACS) method. In certain embodiments, the $K_D$ value can be appropriately determined by using flow cytometry.

The ability to "block binding" or "compete for the same epitope" as used herein refers to the ability of an antibody or antigen-binding fragment to inhibit the binding interaction between two molecules (e.g. human CD3epsilon and an anti-CD3epsilon antibody) to any detectable degree. In certain embodiments, an antibody or antigen-binding fragment that blocks binding between two molecules inhibits the binding interaction between the two molecules by at least 85%, or at least 90%. In certain embodiments, this inhibition may be greater than 85%, or greater than 90%.

The term "epitope" as used herein refers to the specific group of atoms or amino acids on an antigen to which an antibody binds. Two antibodies may bind the same or a closely related epitope within an antigen if they exhibit competitive binding for the antigen. For example, if an antibody or antigen-binding fragment blocks binding of a reference antibody to the antigen (e.g., recombinant human/monkey CD3epsilon or CD3epsilon expressed on surface of cells in the present disclosure) by at least 85%, or at least 90%, then the antibody or antigen-binding fragment may be considered to bind the same/closely related epitope as the reference antibody.

Those skilled in the art will recognize that it is possible to determine, without undue experimentation, if a human monoclonal antibody binds to the same epitope as the antibody of present disclosure (e.g., mouse monoclonal antibodies WBP3311_2.166.48, WBP3311_2.306.4, WBP3311_2.383.47, WBP3311_2.400.5, WBP3311_2.482.5, WBP331_2.488.33, WBP3311_2.615.8, WBP3311_2.844.8, and humanized antibodies WBP3311_2.166.48-z1 and WBP3311_2.306.4-z1) by ascertaining whether the former prevents the latter from binding to a CD3epsilon antigen polypeptide. If the test antibody competes with the antibody of present disclosure, as shown by a decrease in binding by the antibody of present disclosure to the CD3epsilon antigen polypeptide, then the two antibodies bind to the same, or a closely related, epitope. Or if the binding of a test antibody to the CD3epsilon antigen polypeptide was inhibited by the antibody of present disclosure, then the two antibodies bind to the same, or a closely related, epitope.

The various symbols used in the antibody names as provided herein are of different representation: "mIgG2" refers to an antibody with mouse constant region of IgG2 isotype; "uIgG1" refers an antibody with human constant region of IgG1 isotype; "K" or "L" refers to an antibody using the kappa or lambda light chain.

A "conservative substitution" with reference to amino acid sequence refers to replacing an amino acid residue with a different amino acid residue having a side chain with similar physiochemical properties. For example, conservative substitutions can be made among amino acid residues with hydrophobic side chains (e.g. Met, Ala, Val, Leu, and Ile), among residues with neutral hydrophilic side chains (e.g. Cys, Ser, Thr, Asn and Gin), among residues with acidic side chains (e.g. Asp, Glu), among amino acids with basic side chains (e.g. His, Lys, and Arg), or among residues with aromatic side chains (e.g. Trp, Tyr, and Phe). As known in the art, conservative substitution usually does not cause significant change in the protein conformational structure, and therefore could retain the biological activity of a protein.

The term "homologue" and "homologous" as used herein are interchangeable and refer to nucleic acid sequences (or its complementary strand) or amino acid sequences that have sequence identity of at least 80% (e.g., at least 85%, 88%, 90%, 91%, 92%, 93%, 94%, 95%, 96%, 97%, 98%, 99%) to another sequences when optimally aligned.

"Percent (%) sequence identity" with respect to amino acid sequence (or nucleic acid sequence) is defined as the percentage of amino acid (or nucleic acid) residues in a candidate sequence that are identical to the amino acid (or nucleic acid) residues in a reference sequence, after aligning the sequences and, if necessary, introducing gaps, to achieve the maximum number of identical amino acids (or nucleic acids). Conservative substitution of the amino acid residues may or may not be considered as identical residues. Alignment for purposes of determining percent amino acid (or nucleic acid) sequence identity can be achieved, for example, using publicly available tools such as BLASTN, BLASTp (available on the website of U.S. National Center for Biotechnology Information (NCBI), see also, Altschul S. F. et al, J. Mol. Biol., 215:403-410 (1990); Stephen F. et al, Nucleic Acids Res., 25:3389-3402 (1997)), ClustalW2 (available on the website of European Bioinformatics Institute, see also, Higgins D. G. et al, Methods in Enzymology, 266:383-402 (1996); Larkin M. A. et al, Bioinformatics (Oxford, England), 23(21): 2947-8 (2007)), and ALIGN or Megalign (DNASTAR) software. Those skilled in the art may use the default parameters provided by the tool, or may customize the parameters as appropriate for the alignment, such as for example, by selecting a suitable algorithm.

"Effector functions" as used herein refer to biological activities attributable to the binding of Fc region of an antibody to its effectors such as C1 complex and Fc receptor. Exemplary effector functions include: complement dependent cytotoxicity (CDC) induced by interaction of antibodies and C1q on the C1 complex; antibody-dependent cell-mediated cytotoxicity (ADCC) induced by binding of Fc region of an antibody to Fc receptor on an effector cell; and phagocytosis.

"Treating" or "treatment" of a condition as used herein includes preventing or alleviating a condition, slowing the onset or rate of development of a condition, reducing the risk of developing a condition, preventing or delaying the development of symptoms associated with a condition, reducing or ending symptoms associated with a condition, generating a complete or partial regression of a condition, curing a condition, or some combination thereof.

An "isolated" substance has been altered by the hand of man from the natural state. If an "isolated" composition or substance occurs in nature, it has been changed or removed from its original environment, or both. For example, a polynucleotide or a polypeptide naturally present in a living animal is not "isolated," but the same polynucleotide or polypeptide is "isolated" if it has been sufficiently separated from the coexisting materials of its natural state so as to exist in a substantially pure state. An "isolated nucleic acid sequence" refers to the sequence of an isolated nucleic acid molecule. In certain embodiments, an "isolated antibody or antigen-binding fragment thereof" refers to the antibody or antigen-binding fragments having a purity of at least 60%, 70%, 75%, 80%, 81%, 82%, 83%, 84%, 85%, 86%, 87%, 88%, 89%, 90%, 91%, 92%, 93%, 94%, 95%, 96%, 97%, 98%, 99% as determined by electrophoretic methods (such as SDS-PAGE, isoelectric focusing, capillary electrophoresis), or chromatographic methods (such as ion exchange chromatography or reverse phase HPLC).

The term "vector" as used herein refers to a vehicle into which a polynucleotide encoding a protein may be operably inserted so as to bring about the expression of that protein. A vector may be used to transform, transduce, or transfect a host cell so as to bring about expression of the genetic element it carries within the host cell. Examples of vectors include plasmids, phagemids, cosmids, artificial chromosomes such as yeast artificial chromosome (YAC), bacterial artificial chromosome (BAC), or P1-derived artificial chromosome (PAC), bacteriophages such as lambda phage or M13 phage, and animal viruses. Categories of animal viruses used as vectors include retrovirus (including lentivirus), adenovirus, adeno-associated virus, herpesvirus (e.g., herpes simplex virus), poxvirus, baculovirus, papillomavirus, and papovavirus (e.g., SV40). A vector may contain a variety of elements for controlling expression, including promoter sequences, transcription initiation sequences, enhancer sequences, selectable elements, and reporter genes. In addition, the vector may contain an origin of replication. A vector may also include materials to aid in its entry into the cell, including but not limited to a viral particle, a liposome, or a protein coating. A vector can be an expression vector or a cloning vector. The present disclosure provides vectors (e.g., expression vectors) containing the nucleic acid sequence provided herein encoding the antibody or antigen-binding fragment thereof, at least one promoter (e.g., SV40, CMV, EF-1α) operably linked to the nucleic acid sequence, and at least one selection marker. Examples of vectors include, but are not limited to, retrovirus (including lentivirus), adenovirus, adeno-associated virus, herpesvirus (e.g., herpes simplex virus), poxvirus, baculovirus, papillomavirus, papovavirus (e.g., SV40), lambda phage, and M13 phage, plasmid pcDNA3.3, pMD18-T, pOptivec, pCMV, pEGFP, pIRES, pQD-Hyg-GSeu, pALTER, pBAD, pcDNA, pCal, pL, pET, pGEMEX, pGEX, pCI, pEGFT, pSV2, pFUSE, pVITRO, pVIVO, pMAL, pMONO, pSELECT, pUNO, pDUO, Psg5L, pBABE, pWPXL, pBI, p15TV-L, pPro18, pTD, pRS10, pLexA, pACT2.2, pCMV-SCRIPT®, pCDM8, pCDNA1.1/amp, pcDNA3.1, pRc/RSV, PCR 2.1, pEF-1, pFB, pSG5, pXT1, pCDEF3, pSVSPORT, pEF-Bos etc.

The phrase "host cell" as used herein refers to a cell into which an exogenous polynucleotide and/or a vector has been introduced.

A "CD3 related disease or condition" as used herein refers to any disease or condition caused by, exacerbated by, or otherwise linked to increased or decreased expression or activities of CD3. In some embodiments, the CD3 related condition is immune-related disorder, such as, for example, cancer, autoimmune disease, inflammatory disease or infectious disease.

"Cancer" as used herein refers to any medical condition characterized by malignant cell growth or neoplasm, abnormal proliferation, infiltration or metastasis, and includes both solid tumors and non-solid cancers (hematologic malignancies) such as leukemia. As used herein "solid tumor" refers to a solid mass of neoplastic and/or malignant cells.

The term "pharmaceutically acceptable" indicates that the designated carrier, vehicle, diluent, excipient(s), and/or salt is generally chemically and/or physically compatible with the other ingredients comprising the formulation, and physiologically compatible with the recipient thereof.

Anti-CD3epsilon Antibody

The present disclosure provides anti-CD3epsilon antibodies and antigen-binding fragments thereof comprising one or more (e.g. 1, 2, 3, 4, 5, or 6) CDR sequences of an anti-CD3epsilon antibody WBP3311_2.166.48, WBP3311_2.306.4, WBP3311_2.383.47, WBP3311_2.400.5, WBP3311_2.482.5, WBP331_2.488.33, WBP3311_2.615.8, or WBP3311_2.844.8. Throughout the present disclosure, the term "WBP3311" with respect to the antibody names is used interchangeably with "W3311". For example, antibody WBP3311_2.166.48 is also referred to as W3311_2.166.48 and such names refer to the same antibody.

"WBP3311_2.166.48" as used herein refers to a mouse monoclonal antibody having a heavy chain variable region of SEQ ID NO: 81, and a kappa light chain variable region of SEQ ID NO: 83.

"WBP3311_2.306.4" as used herein refers to a mouse monoclonal antibody having a heavy chain variable region of SEQ ID NO: 85, and a kappa light chain variable region of SEQ ID NO: 87.

"WBP3311_2.383.47" as used herein refers to a mouse monoclonal antibody having a heavy chain variable region of SEQ ID NO: 89, and a kappa light chain variable region of SEQ ID NO: 91.

"WBP3311_2.400.5" as used herein refers to a mouse monoclonal antibody having a heavy chain variable region of SEQ ID NO: 93, and a kappa light chain variable region of SEQ ID NO: 95.

"WBP3311_2.482.5" as used herein refers to a mouse monoclonal antibody having a heavy chain variable region of SEQ ID NO: 97, and a kappa light chain variable region of SEQ ID NO: 99.

"WBP331_2.488.33" as used herein refers to a mouse monoclonal antibody having a heavy chain variable region of SEQ ID NO: 101, and a kappa light chain variable region of SEQ ID NO: 103.

"WBP3311_2.615.8" as used herein refers to a mouse monoclonal antibody having a heavy chain variable region of SEQ ID NO: 105, and a kappa light chain variable region of SEQ ID NO: 107.

"WBP3311_2.844.8" as used herein refers to a mouse monoclonal antibody having a heavy chain variable region of SEQ ID NO: 109, and a kappa light chain variable region of SEQ ID NO: 111.

Table 1 shows the CDR sequences of these 8 anti-CD3epsilon antibodies. The heavy chain and light chain variable region sequences are also provided below.

Heavy or kappa light chain variable region sequences of WBP3311_2.166.48, WBP3311_2.306.4, WBP3311_2.383.47, WBP3311_2.400.5, WBP3311_2.482.5, WBP331_2.488.33, WBP3311_2.615.8, and WBP3311_2.844.8, and humanized WBP3311_2.166.48 and WBP3311_2.306.4 antibodies are provided below.

WBP3311_2.166.48-VH
Amino acid sequence (SEQ ID NO: 81):
QVQLQQSGPELVKPGASVKIACKAS<u>GYSFTTYYIH</u>WVKQRPGQGLEWIG<u>W</u>
<u>IFPGNDNIKYSEKFKG</u>KATLTADTSSSTAYMQLSSLTSEDSAVYFCAI<u>DS</u>
<u>VSIYYFDY</u>WGQGTTLTVSS

TABLE 1

| Antibody ID: | | CDR1 | CDR2 | CDR3 |
|---|---|---|---|---|
| WBP3311_2.166.48 | VH | SEQ ID NO: 1<br>GYSFTTYYIH | SEQ ID NO: 3<br>WIFPGNDNIKYSEKFKG | SEQ ID NO: 5<br>DSVSIYYFDY |
| WBP3311_2.166.48 | VK | SEQ ID NO: 2<br>KSSQSLLNSRTRKNYLA | SEQ ID NO: 4<br>WASTRKS | SEQ ID NO: 6<br>TQSFILRT |
| WBP3311_2.306.4 | VH | SEQ ID NO: 7<br>GFAFTDYYIH | SEQ ID NO: 9<br>WISPGNVNTKYNENFKG | SEQ ID NO: 11<br>DGYSLYYFDY |
| WBP3311_2.306.4 | VK | SEQ ID NO: 8<br>KSSQSLLNSRTRKNYLA | SEQ ID NO: 10<br>WASTRQS | SEQ ID NO: 12<br>TQSHTLRT |
| WBP3311_2.383.47 | VH | SEQ ID NO: 13<br>GFTFTNYYIH | SEQ ID NO: 15<br>WISPENGNTKYNENFQD | SEQ ID NO: 17<br>DGYSLYYFDY |
| WBP3311_2.383.47 | VK | SEQ ID NO: 14<br>KSSQSLLNSRTRKNYLA | SEQ ID NO: 16<br>WASIRVS | SEQ ID NO: 18<br>TQSHTLRT |
| WBP3311_2.400.5 | VH | SEQ ID NO: 19<br>GYSFTNYYLH | SEQ ID NO: 21<br>WIFPESDNTKYNEKLKG | SEQ ID NO: 23<br>DSVGNYFFDF |
| WBP3311_2.400.5 | VK | SEQ ID NO: 20<br>KSSQSLVNNRTRKNYLA | SEQ ID NO: 22<br>WASTRES | SEQ ID NO: 24<br>AQSFILRT |
| WBP3311_2.482.5 | VH | SEQ ID NO: 25<br>GYTFTTYYIH | SEQ ID NO: 27<br>WIFPGSDNIKYNENFKD | SEQ ID NO: 29<br>DSVSRYYFDY |
| WBP3311_2.482.5 | VK | SEQ ID NO: 26<br>KSSQSLVNDRTRKNYLA | SEQ ID NO: 28<br>WASTRES | SEQ ID NO: 30<br>AQSFILRT |
| WBP331_2.488.33 | VH | SEQ ID NO: 31<br>GFSFTNYYIH | SEQ ID NO: 33<br>WIFPGTVNTKYNEKFKG | SEQ ID NO: 35<br>DSVGIYYFDF |
| WBP331_2.488.33 | VK | SEQ ID NO: 32<br>KSSQSLLNNRTRKNYLA | SEQ ID NO: 34<br>WASTRES | SEQ ID NO: 36<br>TQSFILRT |
| WBP3311_2.615.8 | VH | SEQ ID NO: 37<br>GYSFTDFYTH | SEQ ID NO: 39<br>WIFPGSDNIKYNEKFKG | SEQ ID NO: 41<br>DSVSVYYFDY |
| WBP3311_2.615.8 | VK | SEQ ID NO: 38<br>KSSQSLLNIRTRKNYLA | SEQ ID NO: 40<br>WASTRDS | SEQ ID NO: 42<br>TQSFILRT |
| WBP3311_2.844.8 | VH | SEQ ID NO: 43<br>GFAFTDYYIH | SEQ ID NO: 45<br>WISPGNVNTKYNENFKG | SEQ ID NO: 47<br>DGYSLYYFDY |
| WBP3311_2.844.8 | VK | SEQ ID NO: 44<br>KSSQSLLNSRTRKNYLA | SEQ ID NO: 46<br>WASTRES | SEQ ID NO: 48<br>TQSHTLRT |

Nucleic acid sequence (SEQ ID NO: 82):
CAGGTCCAGCTGCAGCAGTCTGGACCTGAGCTGGTGAAACCTGGGGCTTC

AGTGAAGATTGCCTGCAAGGCTTCTGGCTACAGCTTCACAACCTACTATA

TACACTGGGTGAAGCAGAGGCCTGGACAGGGACTTGAGTGGATTGGATGG

ATTTTTCCTGGAAATGATAATATTAAGTACAGTGAGAAGTTCAAGGGCAA

GGCCACACTGACGGCAGACACTTCCTCCAGTACAGCCTACATGCAGCTCA

GCAGCCTGACATCTGAGGACTCTGCTGTCTATTTCTGTGCTATAGACTCC

GTTAGTATCTACTACTTTGACTATTGGGGCCAAGGCACCACTCTCACAGT

CTCCTCA

WBP3311_2.166.48-VK
Amino acid sequence (SEQ ID NO: 83):
DIVMSQSPSSLAVSAGEKVTMSCKSSQSLLNSRTRKNYLAWYQQKPGQSP

KLLIYWASTRKSGVPDRFTGSGSGTDFTLTINSVQAEDLAVYYCTQSFIL

RTFGGGTKLEIK

Nucleic acid sequence (SEQ ID NO: 84):
GACATTGTGATGTCACAGTCTCCATCCTCCCTGGCTGTGTCAGCAGGAGA

GAAGGTCACTATGAGCTGCAAATCCAGTCAGAGTCTGCTCAACAGTAGAA

CCCGAAAGAACTACTTGGCTTGGTACCAGCAGAAACCAGGGCAGTCTCCT

AAACTGCTGATCTACTGGGCATCCACTAGGAAATCTGGGGTCCCTGATCG

CTTCACAGGCAGTGGATCTGGGACAGATTTCACTCTCACCATCAACAGTG

TGCAGGCTGAAGACCTGGCAGTTTATTACTGCACGCAATCTTTTATTCTT

CGGACGTTCGGTGGAGGCACCAAGCTGGAAATCAAA

WBP3311_2.306.4-VH
Amino acid sequence (SEQ ID NO: 85):
QVQLQQSGPELVKPGASVRISCKASGFAFTDYYIHWVKQRPGQGLEWIGW

ISPGNVNTKYNENFKGRATLTADLSSSTAYMQLSSLTSEDSAVYFCARDG

YSLYYFDYWGQGTTLTVSS

Nucleic acid sequence (SEQ ID NO: 86):
CAGGTCCAGCTGCAGCAGTCTGGACCTGAATTGGTGAAGCCTGGGGCTTC

CGTGAGGATATCCTGCAAGGCTTCTGGCTTCGCCTTCACAGACTACTATA

TACACTGGGTGAAGCAGAGGCCTGGACAGGGTCTTGAGTGGATTGGATGG

ATTTCTCCTGGAAATGTTAATACTAAATACAATGAAAACTTCAAGGGCAG

GGCCACACTGACTGCAGACCTATCCTCCAGCACAGCCTACATGCAGCTCA

GCAGCCTGACCTCTGAGGACTCTGCGGTCTATTTCTGTGCAAGAGATGGA

TATTCCCTGTATTACTTTGACTACTGGGGCCAAGGCACCACTCTCACAGT

CTCCTCA

WBP3311_2.306.4-VK
Amino acid sequence (SEQ ID NO: 87):
DIVMSQSPSSLTVSAGEKVTMSCKSSQSLLNSRTRKNYLAWYQQKPGQSP

KLLIYWASTRQSGVPDRFTGSGSGTAFTLTISGVQAEDLAVYFCTQSHTL

RTFGGGTKLEIK

Nucleic acid sequence (SEQ ID NO: 88):
GACATTGTGATGTCACAGTCTCCATCCTCCCTGACTGTGTCAGCAGGAGA

GAAGGTCACTATGAGCTGCAAATCCAGTCAGAGTCTGCTCAACAGTAGAA

CCCGAAAGAACTACTTGGCTTGGTACCAGCAGAAGCCAGGGCAGTCTCCT

AAACTACTAATCTACTGGGCATCCACTAGGCAATCTGGGGTCCCTGATCG

CTTCACAGGCAGTGGATCTGGGACAGCTTTCACTCTCACCATCAGCGGTG

TGCAGGCTGAAGACCTGGCAGTTTATTTCTGCACGCAATCTCATACTCTT

CGGACGTTCGGTGGAGGCACCAAGCTGGAAATCAAA

WBP3311_2.383.47-VH
Amino acid sequence (SEQ ID NO: 89):
QVQLQQSGPELVKPGASVRISCKTSGFTFTNYYIHWVIQRPGQGLEWIGW

ISPENGNTKYNENFQDKATLTADISSSTAYMHLSSLTSEDSAVYFCARDG

YSLYYFDYWGQGTTLTVSS

Nucleic acid sequence (SEQ ID NO: 90):
CAGGTCCAGCTGCAGCAGTCTGGACCTGAATTGGTGAAGCCTGGGGCTTG

AGTGAGGATATCCTGCAAGACTTCTGGCTTCACCTTCACAAACTACTATA

TACACTGGGTGATACAGAGGCCTGGACAGGGACTTGAGTGGATTGGTTGG

ATTTCTCCTGAAAATGGTAATACTAAATACAATGAAAACTTCCAGGACAA

GGCCACACTGACTGCAGACATATCGTCCAGCACAGCCTACATGCACCTCA

GCAGCCTGACCTCTGAGGACTCTGCGGTCTATTTCTGTGCAAGAGATGGG

TATTCCCTTTACTACTTTGACTACTGGGGCCAAGGCACCACTCTCACAGT

CTCCTCA

WBP3311_2.383.47-VK
Amino acid sequence (SEQ ID NO: 91):
DIVMSQSPSSLTVSAGEKVTMSCKSSQSLLNSRTRKNYLAWYQQKPGQSP

KLLIYWASIRVSGVPDRFTGSGSGTTFTLTISGVQAEDLAVYYCTQSHTL

RTFGGGTKLEIK

Nucleic acid sequence (SEQ ID NO: 92):
GACATTGTGATGTCACAGTCTCCATCCTCCCTGACTGTGTCAGCAGGAGA

GAAGGTCACTATGAGCTGCAAATCCAGTCAGAGTCTGCTCAACAGTAGAA

CCCGAAAGAACTACTTGGCTTGGTACCAGCAGAAACCAGGGCAGTCTCCT

AAGCTACTGATCTACTGGGCATCCATTAGGGTATCTGGGGTCCCTGATCG

CTTCACAGGCAGTGGATCTGGGACAACTTTCACTCTCACCATCAGCGGTG

TGCAGGCTGAAGACCTGGCAGTTTATTATTGCACGCAATCTCATACTCTT

CGGACGTTCGGTGGAGGCACCAAGCTGGAAATCAAA

WBP3311_2.400.5-VH
Amino acid sequence (SEQ ID NO: 93):
QVQLQQSGPELVNPGASVKISCKASGYSFTNYYLHWVKQRPGQGLEWIGW

IFPESDNTKYNEKLKGKATLTADTSSDTAYMHLSSLTFEDSAVYFCARDS

VGNYFFDFWGQGTTLTVSS

Nucleic acid sequence (SEQ ID NO: 94):
CAGGTCCAGCTGCAGCAGTCTGGACCTGAGCTGGTGAATCCTGGGGCTTC

AGTGAAGATATCCTGCAAGGCTTCTGGCTACAGTTTCACAAACTACTATT

TACACTGGGTGAAACAGAGGCCTGGACAGGGACTTGAGTGGATTGGATGG

ATTTTTCCTGAAAGTGATAATACCAAGTACAATGAGAAATTGAAGGGCAA

GGCCACACTGACGGCAGACACATCCTCCGATACAGCCTACATGCACCTCA

GCAGCCTGACATTTGAGGACTCTGCAGTCTATTTCTGTGCAAGAGACTCC

GTTGGAAACTACTTCTTTGACTTCTGGGGCCAAGGCACCACTCTCACAGT

CTCCTCA

WBP3311_2.400.5-VK
Amino acid sequence (SEQ ID NO: 95):
DIVMSQSPSSLAVSAGEKVTMRC<u>KSSQSLVNNRTRKNYLA</u>WYQQKPGQPP KLLIY<u>WASTRES</u>GVPDRFTGSGSGTDFTLTISSVQAEDLAVYYC<u>AQSFIL</u>

<u>RT</u>FGGGTKLEIK

Nucleic acid sequence (SEQ ID NO: 96):
GACATTGTGATGTCACAGTCTCCATCCTCCCTGGCTGTGTCAGCGGGAGA

GAAGGTCACTATGAGGTGCAAATCCAGTCAGAGTCTGGTCAACAATAGAA

CCCGAAAGAACTACTTGGCATGGTACCAGCAGAAACCAGGGCAGCCTCCT

AAACTATTGATCTACTGGGCATCCACTAGGGAATCTGGGGTCCCTGATCG

CTTCACAGGCAGTGGATCTGGGACAGATTTCACTCTCACCATCAGCAGTG

TGCAGGCTGAAGACCTGGCAGTTTATTACTGCGCGCAATCTTTTATTCTT

CGGACGTTCGGTGGAGGCACCAAACTGGAAATCAAA

WBP3311_2.482.5-VH
Amino acid sequence (SEQ ID NO: 97):
QVQLQQSGPELVKPGSSVKISCKPS<u>GYTFTTYYIH</u>WVKQRPGQGLEWIG<u>W</u>

<u>IFPGSDNIKYNENFKD</u>KATLTADTSSSTAYMQLSSLTSEDSAVYFCAR<u>DS</u>

<u>VSRYYFDY</u>WGQGTILTVSS

Nucleic acid sequence (SEQ ID NO: 98):
CAGGTTCAGCTGCAGCAGTCTGGACCTGAGCTGGTGAAACCTGGGTCTTC

AGTGAAGATATCCTGCAAACCTTCTGGCTACACCTTCACAACTTACTATA

TACATTGGGTGAAGCAGAGGCCTGGACAGGGACTTGAGTGGATTGGATGG

ATTTTTCCTGGAAGTGATAATATTAAATACAATGAGAATTTCAAGGACAA

GGCCACACTGACGGCAGACACATCCTCCAGCACAGCCTACATGCAGCTCA

GCAGCCTGACATCTGAAGACTCTGCAGTCTATTTCTGTGCAAGAGACTCC

GTCAGTAGGTACTACTTTGACTACTGGGGCCAAGGCACCATTCTCACAGT

TTCTTCA

WBP3311_2.482.5-VK
Amino acid sequence (SEQ ID NO: 99):
DIVMSQSPSSLAVSAGEKVTMSC<u>KSSQSLVNDRTRKNYLA</u>WYQQKPGLSP KLLIY<u>WASTRES</u>GVPDRFTGSGSGTDFTLTISSVQAEDLAVYYC<u>AQSFIL</u>

<u>RT</u>FGGGTKLEIK

Nucleic acid sequence (SEQ ID NO: 100):
GACATTGTGATGTCACAGTCTCCATCCTCCCTGGCTGTGTCAGCAGGAGA

GAAGGTCACTATGAGCTGCAAATCCAGTCAGAGTCTGGTCAATGATAGAA

CCCGAAAAAACTACTTGGCTTGGTACCAGCAGAAACCAGGGCTGTCTCCT

AAACTGCTGATCTACTGGGCTTCCACTAGGGAATCTGGGGTCCCTGATCG

CTTCACAGGCAGTGGATCTGGGACAGATTTCACTCTCACCATCAGCAGTG

TGCAGGCTGAAGACCTGGCTGTTTATTACTGCGCGCAATCTTTTATTCTT

CGGACGTTCGGTGGAGGCACCAAGCTGGAAATCAAA

WBP331_2.488.33-VH
Amino acid sequence (SEQ ID NO: 101):
QVQLQQSGPELVKPGTSVKISCKAS<u>GFSFTNYYIH</u>WVKQRPGQGPEWIG<u>W</u>

<u>IFPGTVNTKYNEKFKG</u>KATLTADTSSNTAFMQLSSLTSADSAVYFCARDS

<u>VGIYYFDF</u>WGLGTTLTVSS

Nucleic acid sequence (SEQ ID NO: 102):
CAGGTCCAGCTGCAACAGTCTGGACCTGAACTGGTGAAACCTGGGACTTC

AGTGAAGATATCCTGCAAGGCTTCTGGCTTCAGCTTCACAAACTACTATA

TACACTGGGTGAAGCAGAGGCCTGGACAGGGACCTGAGTGGATTGGATGG

ATTTTTCCTGGAACTGTTAATACTAAGTACAATGAGAAGTTCAAGGGTAA

GGCCACACTGACGGCAGACACATCCTCCAATACAGCCTTCATGCAGCTCA

GCAGCCTGACTTCTGCGGACTCTGCAGTCTATTTCTGTGCAAGAGACTCC

GTTGGTATCTACTACTTTGACTTCTGGGGCCTAGGCACCACTCTCACAGT

CTCCTCA

WBP331_2.488.33-VK
Amino acid sequence (SEQ ID NO: 103):
DIVMSQSPSSLAVSAGEKVTVSC<u>KSSQSLLNNRTRKNYLA</u>WYQQKPGQSP KLLIY<u>WASTRES</u>GVPDRFTGSGSGTDFTLTISSVQAEDLAVYYC<u>TQSFIL</u>

<u>RT</u>FGGGTKLEIK

Nucleic acid sequence (SEQ ID NO: 104):
GACATTGTGATGTCACAGTCTCCATCCTCCCTGGCTGTGTCAGCAGGAGA

GAAGGTCACTGTGAGTTGCAAATCCAGTCAGAGTCTGCTCAACAATAGAA

CCCGAAAAAACTACTTGGCTTGGTACCAGCAGAAACCAGGGCAGTCTCCT

AAACTACTAATCTACTGGGCATCCACTAGGGAATCTGGGGTCCCTGATCG

CTTCACAGGCAGTGGATCTGGTACAGATTTCACTCTCACCATCAGCAGTG

TGCAGGCTGAAGACCTGGCAGTTTATTACTGCACGCAATCTTTTATTCTT

CGGACGTTCGGTGGAGGCACCAAGCTGGAGATCAAA

WBP3311_2.615.8-VH
Amino acid sequence (SEQ ID NO: 105):
QVQLQQSGPELVKPGTSMKISCKAS<u>GYSFTDFYTH</u>WVRQRPGQGLEWIG<u>W</u>

<u>IFPGSDNIKYNEKFKG</u>KATLTADTSSSTAYMQLSSLTSEDSAVYFCAR<u>DS</u>

<u>VSVYYFDY</u>WGQGTTLTVSS

Nucleic acid sequence (SEQ ID NO: 106):
CAGGTCCAGCTGCAGCAGTCTGGACCTGAGCTGGTAAAACCTGGACTTC

AATGAAAATATCCTGCAAGGCTTCTGGCTACAGTTTCACAGACTTCTATA

CACACTGGGTGAGGCAGAGGCCTGGACAGGGACTTGAGTGGATTGGATGG

ATTTTTCCTGGAAGTGATAATATTAAATACAATGAAGTTCAAGGGCAA

GGCCACACTGACGGCAGACACATCCTCCAGCACAGCCTACATGCAGCTCA

GCAGCCTGACATCTGAGGACTCTGCAGTCTATTTCTGTGCAAGAGACTCC

GTTAGTGTCTACTACTTTGACTATTGGGGCCAAGGCACCACTCTCACAGT

CTCCTCA

WBP3311_2.615.8-VK
Amino acid sequence (SEQ ID NO: 107):
DIVMSQSPSSLAVTAGEKVTMSC<u>KSSQSLLNIRTRKNYLA</u>WYQQKPGQSP KLLIY<u>WASTRDS</u>GVPDRFTGSGSGTDFTLTISSVQAEDLAVYYC<u>TQSFIL</u>

<u>RT</u>FGGGTKLEIK

Nucleic acid sequence (SEQ ID NO: 108):
GACATCGTGATGTCACAGTCTCCATCCTCCCTGGCTGTGACAGCAGGAGA

GAAGGTCACTATGAGCTGCAAATCCAGTCAGAGTCTGCTCAACATTAGAA

CCCGAAAGAACTACTTGGCTTGGTACCAACAGAAACCAGGGCAGTCTCCT

-continued
AAACTGCTGATCTACTGGGCATCCACTAGGGACTCTGGGGTCCCTGATCG

CTTCACAGGCAGTGGATCTGGGACAGATTTCACTCTCACCATCAGCAGTG

TGCAGGCTGAAGACCTGGCAGTTTATTACTGCACGCAATCTTTTATTCTT

CGGACGTTCGGTGGAGGCACCAAGCTGGAAATCAAA

WBP3311_2.844.8-VH
Amino acid sequence (SEQ ID NO: 109):
QVQLQQSGPELVKPGASVRISCKAS<u>GFAFTDYYIH</u>WVKQRPGQGLEWIG<u>W ISPGNVNTKYNENFKG</u>RATLTADLSSSTAYMQLSSLTSEDSAVYFCARD<u>G YSLYYFDY</u>WGQGTTLTVSS Nucleic acid sequence (SEQ ID NO: 110):
CAGGTCCAGCTGCAGCAGTCTGGACCTGAATTGGTGAAGCCTGGGCTTC

CGTGAGGATATCCTGCAAGGCTTCTGGCTTCGCCTTCACAGACTACTATA

TACACTGGGTGAAGCAGAGGCCTGGACAGGGTCTTGAGTGGATTGGATGG

ATTTCTCCTGGAAATGTTAATACTAAATACAATGAAAACTTCAAGGGCAG

GGCCACACTGACTGCAGACCTATCCTCCAGCACAGCCTACATGCAGCTCA

GCAGCCTGACCTCTGAGGACTCTGCGGTCTATTTCTGTGCAAGAGATGGA

TATTCCCTGTATTACTTTGACTACTGGGGCCAAGGCACCACTCTCACAGT

CTCCTCA

WBP3311_2.844.8-VK
Amino acid sequence (SEQ ID NO: 111):
DIVMSQSPSSLTVSAGEKVTMSC<u>KSSQSLLNSRTRKNYLA</u>WYQQKPGQSP KLLIY<u>WASTRES</u>GVPDRFTGSGSGTAFTLTISGVQAEDLAVYFC<u>TQSHTL RT</u>FGGGTKLEIK Nucleic acid sequence (SEQ ID NO: 112):
GACATTGTGATGTCACAGTCTCCATCCTCCCTGACTGTGTCAGCAGGAGA

GAAGGTCACTATGAGCTGCAAATCCAGTCAGAGTCTGCTCAACAGTAGAA

CCCGAAAGAACTACTTGGCTTGGTACCAGCAGAAACCAGGGCAGTCTCCT

AAGCTACTAATCTACTGGGCATCCACTAGGGAATCTGGGGTCCCTGATCG

CTTCACAGGCAGTGGATCTGGGACAGCTTTCACTCTCACCATCAGCGGTG

TGCAGGCTGAAGACCTGGCAGTTTATTTCTGCACGCAATCTCATACTCTT

CGGACGTTCGGTGGAGGCACCAAGCTGGAAATCAAA

CDRs are known to be responsible for antigen binding, however, it has been found that not all of the 6 CDRs are indispensable or unchangeable. In other words, it is possible to replace or change or modify one or more CDRs in anti-CD3epsilon antibody WBP3311_2.166.48, WBP3311_2.306.4, WBP3311_2.383.47, WBP3311_2.400.5, WBP3311_2.482.5, WBP331_2.488.33, WBP3311_2.615.8, or WBP3311_2.844.8, yet substantially retain the specific binding affinity to CD3epsilon.

In certain embodiments, the anti-CD3epsilon antibodies and the antigen-binding fragments provided herein comprise a heavy chain CDR3 sequence of one of the anti-CD3epsilon antibodies WBP3311_2.166.48, WBP3311_2.306.4, WBP3311_2.383.47, WBP3311_2.400.5, WBP3311_2.482.5, WBP331_2.488.33, WBP3311_2.615.8, and WBP3311_2.844.8. In certain embodiments, the anti-CD3epsilon antibodies and the antigen-binding fragments provided herein comprise a heavy chain CDR3 sequence selected from the group consisting of SEQ ID NOs: 5, 11, 17, 23, 29, 35, 41, and 47. Heavy chain CDR3 regions are located at the center of the antigen-binding site, and therefore are believed to make the most contact with antigen and provide the most free energy to the affinity of antibody to antigen. It is also believed that the heavy chain CDR3 is by far the most diverse CDR of the antigen-binding site in terms of length, amino acid composition and conformation by multiple diversification mechanisms (Tonegawa S. Nature. 302:575-81). The diversity in the heavy chain CDR3 is sufficient to produce most antibody specificities (Xu J L, Davis M M. Immunity. 13:37-45) as well as desirable antigen-binding affinity (Schier R, etc. J Mol Biol. 263:551-67).

In certain embodiments, the antibodies and antigen-binding fragments thereof provided herein comprise suitable framework region (FR) sequences, as long as the antibodies and antigen-binding fragments thereof can specifically bind to CD3epsilon. The CDR sequences provided in Table 1 are obtained from mouse antibodies, but they can be grafted to any suitable FR sequences of any suitable species such as mouse, human, rat, rabbit, among others, using suitable methods known in the art such as recombinant techniques.

In certain embodiments, the antibodies and antigen-binding fragments thereof provided herein are humanized. A humanized antibody or antigen-binding fragment is desirable in its reduced immunogenicity in human. A humanized antibody is chimeric in its variable regions, as non-human CDR sequences are grafted to human or substantially human FR sequences. Humanization of an antibody or antigen-binding fragment can be essentially performed by substituting the non-human (such as murine) CDR genes for the corresponding human CDR genes in a human immunoglobulin gene (see, for example, Jones et al. (1986) Nature 321:522-525; Riechmann et al. (1988) Nature 332:323-327; Verhoeyen et al. (1988) Science 239:1534-1536).

Suitable human heavy chain and light chain variable domains can be selected to achieve this purpose using methods known in the art. In an illustrative example, "best-fit" approach can be used, where a non-human (e.g. rodent) antibody variable domain sequence is screened or BLASTed against a database of known human variable domain sequences, and the human sequence closest to the non-human query sequence is identified and used as the human scaffold for grafting the non-human CDR sequences (see, for example, Sims et al, (1993) J. Immunol. 151:2296; Chothia et al. (1987) J. Mot. Biol. 196:901). Alternatively, a framework derived from the consensus sequence of all human antibodies may be used for the grafting of the non-human CDRs (see, for example, Carter et al. (1992) Proc. Natl. Acad. Sci. USA, 89:4285; Presta et al. (1993) J. Immunol., 151:2623).

In certain embodiments, the humanized antibodies or antigen-binding fragments provided herein are composed of substantially all human sequences except for the CDR sequences which are non-human. In some embodiments, the variable region FRs, and constant regions if present, are entirely or substantially from human immunoglobulin sequences. The human FR sequences and human constant region sequences may be derived different human immunoglobulin genes, for example, FR sequences derived from one human antibody and constant region from another human antibody. In some embodiments, the humanized antibody or antigen-binding fragment comprise human FR1-4 and human JH and Jκ.

In certain embodiments, the humanized antibodies and antigen-binding fragment thereof provided herein comprise one or more FR sequences of WBP3311_2.166.48-z1 or WBP3311_2.306.4-z1. Table 2 below shows the FR sequences of WBP3311_2.166.48-z1 or WBP3311_2.306.4-z1. The native mouse FR sequences are also listed in Table 2. The heavy chain and light chain variable region sequences are also provided below.

"WBP3311_2.166.48-z1" as used herein refers to a humanized antibody based on WBP3311_2.166.48 that comprises a heavy chain variable region of SEQ ID NO: 113, and a kappa light chain variable region of SEQ ID NO: 115. WBP3311_2.166.48-z1 has comparable affinity to the antigen as compared with its parent antibody WBP3311_2.166.48.

"WBP3311_2.306.4-z1" as used herein refers to a humanized antibody based on WBP3311_2.306.4 that comprises a heavy chain variable region of SEQ ID NO: 117, and a kappa light chain variable region of SEQ ID NO: 119. WBP3311_2.306.4-z1 has comparable affinity to the antigen as compared with its parent antibody WBP3311_2.306.4.

```
WBP3311_2.166.48-z1-VH
Amino acid sequence (SEQ ID NO: 113):
QVQLVQSGAEVKKPGSSVKVSCKASGYSFTTYYIHWVRQAPGQGLEWMGW

IFPGNDNIKYSEKFKGRVTITADKSTSTAYMELSSLRSEDTAVYYCAIDS

VSIYYFDYWGQGTLVTVSS

Nucleic acid sequence (SEQ ID NO: 114):
CAGGTGCAACTCGTGCAGTCTGGAGCTGAAGTGAAGAAGCCTGGGTCTTC

AGTCAAGGTCAGTTGCAAGGCCAGTGGGTATTCCTTCACTACCTACTACA

TCCACTGGGTGCGGCAGGCACCAGGACAGGGGCTTGAGTGGATGGGCTGG

ATCTTTCCCGGCAACGATAATATTAAGTACAGCGAGAAGTTCAAAGGGAG

GGTCACCATTACCGCCGACAAATCCACTTCCACAGCCTACATGGAGTTGA

GCAGCCTGAGATCCGAGGATACAGCCGTGTACTACTGTGCCATTGACAGC
```

TABLE 2

|  | FR1 | FR2 | FR3 | FR4 |
| --- | --- | --- | --- | --- |
| WBP3311_2.166.48-VH | SEQ ID NO: 49<br>QVQLQQSGPEL<br>VKPGASVKIAC<br>KAS | SEQ ID NO: 51<br>WVKQRPGQGLE<br>WIG | SEQ ID NO: 53<br>KATLTADTSSS<br>TAYMQLSSLTS<br>EDSAVYFCAI | SEQ ID NO: 55<br>WGQGTTLTVSS |
| WBP3311_2.166.48-z1-VH | SEQ ID NO: 57<br>QVQLVQSGAEV<br>KKPGSSVKVSC<br>KAS | SEQ ID NO: 59<br>WVRQAPGQGLE<br>WMG | SEQ ID NO: 61<br>RVTITADKSTS<br>TAYMELSSLRS<br>EDTAVYYCAI | SEQ ID NO: 63<br>WGQGTLVTVSS |
| WBP3311_2.166.48-VK | SEQ ID NO: 50<br>DIVMSQSPSSL<br>AVSAGEKVTMS<br>C | SEQ ID NO: 52<br>WYQQKPGQSPK<br>LLIY | SEQ ID NO: 54<br>GVPDRFTGSGS<br>GTDFTLTINSV<br>QAEDLAVYYC | SEQ ID NO: 56<br>FGGGTKLEIK |
| WBP3311_2.166.48-z1-VK | SEQ ID NO: 58<br>DIVMTQSPDSL<br>AVSLGERATIN<br>C | SEQ ID NO: 60<br>WYQQKPGQPPK<br>LLIY | SEQ ID NO: 62<br>GVPDRFSGSGS<br>GTDFTLTISSL<br>QAEDVAVYYC | SEQ ID NO: 64<br>FGGGTKVEIK |
| WBP3311_2.306.4-VH | SEQ ID NO: 65<br>QVQLQQSGPEL<br>VKPGASVRLSC<br>KAS | SEQ ID NO: 67<br>WMKQRPGQGLE<br>WIG | SEQ ID NO: 69<br>RATVTADLSSS<br>TAYMQLSSLTS<br>EDSAVYFCAR | SEQ ID NO: 71<br>WGQGTTLTVSS |
| WBP3311_2.306.4-z1-VH | SEQ ID NO: 73<br>QVQLVQSGAEV<br>KKPGSSVKVSC<br>KAS | SEQ ID:NO: 75<br>WVRQAPGQGLE<br>WMG | SEQ ID NO: 77<br>RVTITADKSTS<br>TAYMELSSLRS<br>EDTAVYYCAR | SEQ ID NO: 79<br>WGQGTLVTVSS |
| WBP3311_2.306.4-VK | SEQ ID NO: 66<br>DIVMSQSPSSL<br>TVSAGEKVTMS<br>C | SEQ ID NO: 68<br>WYQQKPGQSPK<br>LLIY | SEQ ID NO: 70<br>GVPDRFTGSGS<br>GTAFTLTISGV<br>QAEDLAVYFC | SEQ ID NO: 72<br>FGGGTKLEIK |
| WBP3311_2.306.4-z1-VK | SEQ ID NO: 74<br>DIVMTQSPDSL<br>AVSLGERATIN<br>C | SEQ ID NO: 76<br>WYQQKPGQPPK<br>LLIY | SEQ ID NO: 78<br>GVPDRFSGSGS<br>GTDFTLTISSL<br>QAEDVAVYYC | SEQ ID NO: 80<br>FGGGTKVEIK |

-continued
GTGTCCATCTACTACTTTGACTACTGGGGCCAGGGCACACTGGTCACAGT

GAGCAGC

WBP3311_2.166.48-z1-VK
Amino acid sequence (SEQ ID NO: 115):
DIVMTQSPDSLAVSLGERATINCKSSQSLLNSRTRKNYLAWYQQKPGQPP

KLLIYWASTRKSGVPDRFSGSGSGTDFTLTISSLQAEDVAVYYCTQSFIL

RTFGGGTKVEIK

Nucleic acid sequence (SEQ ID NO: 116):
GACATCGTCATGACCCAGTCCCCAGACTCTTTGGCAGTGTCTCTCGGGGA

AAGAGCTACCATCAACTGCAAGAGCAGCCAGTCCCTTCTGAACAGCAGGA

CCAGGAAGAATTACCTCGCCTGGTACCAACAGAAGCCCGGACAGCCTCCT

AAGCTCCTGATCTACTGGGCCTCAACCCGGAAGAGTGGAGTGCCCGATCG

CTTTAGCGGGAGCGGCTCCGGGACAGATTTCACACTGACAATTTCCTCCC

TGCAGGCCGAGGACGTCGCCGTGTATTACTGTACTCAGAGCTTCATTCTG

CGGACATTTGGCGGCGGGACTAAAGTGGAGATTAAG

WBP3311_2.306.4-z1-VH
Amino acid sequence (SEQ ID NO: 117):
QVQLVQSGAEVKKPGSSVKVSCKASGFAFTDYYIHWVRQAPGQGLEWMGW

ISPGNVNTKYNENFKGRVTITADKSTSTAYMELSSLRSEDTAVYYCARDG

YSLYYFDYWGQGTLVTVSS

Nucleic acid sequence (SEQ ID NO: 118):
CAGGTGCAGCTTGTGCAGTCTGGGGCAGAAGTGAAGAAGCCTGGGTCTAG

TGTCAAGGTGTCATGCAAGGCTAGCGGGTTCGCCTTTACTGACTACTACA

TCCACTGGGTGCGGCAGGCTCCCGGACAAGGGTTGGAGTGGATGGGATGG

ATCTCCCCAGGCAATGTCAACACAAAGTACAACGAGAACTTCAAAGGCCG

CGTCACCATTACCGCCGACAAGAGCACCTCCACAGCCTACATGGAGCTGT

CCAGCCTCAGAAGCGAGGACACTGCCGTCTACTACTGTGCCAGGGATGGG

TACTCCCTGTATTACTTTGATTACTGGGGCCAGGGCACACTGGTGACAGT

GAGCTCC

WBP3311_2.306.4-z1-VK
Amino acid sequence (SEQ ID NO: 119):
DIVMTQSPDSLAVSLGERATINCKSSQSLLNSRTRKNYLAWYQQKPGQPP

KLLIYWASTRQSGVPDRFSGSGSGTDFTLTISSLQAEDVAVYYCTQSHTL

RTFGGGTKVEIK

Nucleic acid sequence (SEQ ID NO: 120):
GATATCGTGATGACCCAGAGCCCAGACTCCCTTGCTGTCTCCCTCGGCGA

AAGAGCAACCATCAACTGCAAGAGCTCCCAAAGCCTGCTGAACTCCAGGA

CCAGGAAGAATTACCTGGCCTGGTATCAGCAGAAGCCCGGCCAGCCTCCT

AAGCTGCTCATCTACTGGGCCTCCACCCGGCAGTCTGGGGTGCCCGATCG

GTTTAGTGGATCTGGGAGCGGGACAGACTTCACATTGACAATTAGCTCAC

TGCAGGCCGAGGACGTGGCCGTCTACTACTGTACTCAGAGCCACACTCTC

CGCACATTCGGCGGAGGGACTAAAGTGGAGATTAAG

The two exemplary humanized anti-CD3epsilon antibodies WBP3311_2.166.48-z1 or WBP3311_2.306.4-z1 both retained the specific binding affinity to CD3-expressing cell (e.g. CD4 T cell), and are at least comparable to, or even better than, the parent mouse antibodies in that aspect. The two exemplary humanized antibodies both retained their functional interaction with CD3-expressing cell, in that both can activate human T cells and trigger cytokine release of TNFalpha and IFNgamma.

In some embodiments, the FR regions derived from human may comprise the same amino acid sequence as the human immunoglobulin from which it is derived. In some embodiments, one or more amino acid residues of the human FR are substituted with the corresponding residues from the parent non-human antibody. This may be desirable in certain embodiments to make the humanized antibody or its fragment closely approximate the non-human parent antibody structure. In certain embodiments, the humanized antibody or antigen-binding fragment provided herein comprises no more than 10, 9, 8, 7, 6, 5, 4, 3, 2, or 1 amino acid residue substitutions in each of the human FR sequences, or no more than 10, 9, 8, 7, 6, 5, 4, 3, 2, or 1 amino acid residue substitutions in all the FRs of a heavy or a light chain variable domain. In some embodiments, such change in amino acid residue could be present in heavy chain FR regions only, in light chain FR regions only, or in both chains.

In certain embodiments, the antibodies and antigen-binding fragments thereof provided herein comprise a heavy chain variable domain sequence selected from the group consisting of SEQ ID NO: 81, SEQ ID NO: 85, SEQ ID NO: 89, SEQ ID NO: 93, SEQ ID NO: 97, SEQ ID NO: 101, SEQ ID NO: 105, SEQ ID NO: 109, SEQ ID NO: 113, SEQ ID NO: 117. In certain embodiments, the antibodies and antigen-binding fragments thereof provided herein comprise a light chain variable domain sequence selected from the group consisting of SEQ ID NO: 83, SEQ ID NO: 87, SEQ ID NO: 91, SEQ ID NO: 95, SEQ ID NO: 99, SEQ ID NO: 103, SEQ ID NO: 107, SEQ ID NO: 111, SEQ ID NO: 115, SEQ ID NO: 119.

In some embodiments, the anti-CD3epsilon antibodies and the antigen-binding fragments provided herein comprise all or a portion of the heavy chain variable domain and/or all or a portion of the light chain variable domain. In one embodiment, the anti-CD3epsilon antibodies and the antigen-binding fragments provided herein is a single domain antibody which consists of all or a portion of the heavy chain variable domain provided herein. More information of such a single domain antibody is available in the art (see, e.g., U.S. Pat. No. 6,248,516).

In certain embodiments, the anti-CD3epsilon antibodies and the fragments thereof provided herein further comprise an immunoglobulin constant region. In some embodiments, an immunoglobulin constant region comprises a heavy chain and/or a light chain constant region. The heavy chain constant region comprises CH1, hinge, and/or CH2-CH3 regions. In certain embodiments, the heavy chain constant region comprises an Fc region. In certain embodiments, the light chain constant region comprises Cκ.

In some embodiments, the anti-CD3epsilon antibodies and antigen-binding fragments thereof have a constant region of IgG1 or IgG2a isotype, which has reduced or depleted effector function such as ADCC or CDC, which can be evaluated using various assays such as Fc receptor binding assay, C1q binding assay, and cell lysis assay.

Binding affinity of the antibody and antigen-binding fragment provided herein can be represented by $K_D$ value, which represents the ratio of dissociation rate to association rate ($k_{off}/k_{on}$) when the binding between the antigen and antigen-binding molecule reaches equilibrium. The antigen-binding affinity (e.g. $K_D$) can be appropriately determined using suitable methods known in the art, including, for example, flow cytometry assay. In some embodiments, binding of the antibody to the antigen at different concentrations can be determined by flow cytometry, the determined mean fluorescence intensity (MFI) can be firstly plotted against antibody concentration, $K_D$ value can then be calculated by fitting the dependence of specific binding fluorescence intensity (Y) and the concentration of antibodies (X) into the one site saturation equation: $Y=B_{max}*X/(K_D+X)$ using Prism version 5 (GraphPad Software, San Diego, Calif.), wherein $B_{max}$ refers to the maximum specific binding of the tested antibody to the antigen.

In certain embodiments, the anti-CD3epsilon antibodies and antigen-binding fragments thereof provided herein are capable of specifically binding to human CD3epsilon expressed on a cell surface, or a recombinant human CD3epsilon. CD3epsilon is a receptor expressed on cell. A recombinant CD3epsilon is soluble CD3epsilon which is recombinantly expressed and is not associated with a cell membrane. A recombinant CD3epsilon can be prepared by various recombinant technologies. In one example, the CD3 epsilon DNA sequence encoding the extracellular domain of human CD3 epsilon (NP_000724.1) (Met1-Asp126) can be fused with a polyhistidine tag at the C-terminus in an expression vector, and then transfected and expressed in 293E cells and purified by Ni-Affinity chromatography.

In some embodiments, the anti-CD3epsilon antibodies and antigen-binding fragments thereof provided herein are capable of specifically binding to human CD3epsilon expressed on surface of cells with a binding affinity ($K_D$) of no more than $5\times10^{-9}$M, no more than $4\times10^{-9}$M, no more than $3\times10^{-9}$M, no more than $2\times10^{-9}$M, no more than $10^{-9}$M, no more than $5\times10^{-10}$M, no more than $4\times10^{-10}$M, no more than $3\times10^{-10}$M, no more than $2\times10^{-10}$M, no more than $10^{-10}$M, no more than $5\times10^{-11}$ M, or no more than $4\times10^{-11}$ M, no more than $3\times10^{-11}$ M, or no more than $2\times10^{-11}$ M, or no more than $10^{-11}$ M as measured by flow cytometry assay.

In certain embodiments, the anti-CD3epsilon antibodies and antigen-binding fragments thereof provided herein cross-react with Cynomolgus monkey CD3epsilon, for example, Cynomolgus monkey CD3epsilon expressed on a cell surface, or a soluble recombinant Cynomolgus monkey CD3epsilon.

Binding of the antibodies to recombinant CD3epsilon or CD3epsilon expressed on surface of cells can also be represented by "half maximal effective concentration" ($EC_{50}$) value, which refers to the concentration of an antibody where 50% of its maximal effect (e.g., binding or inhibition etc.) is observed. The $EC_{50}$ value can be measured by methods known in the art, for example, sandwich assay such as ELISA, Western Blot, flow cytometry assay, and other binding assay. In certain embodiments, the antibodies and the fragments thereof provided herein specifically bind to recombinant human CD3epsilon at an $EC_{50}$ (i.e. 50% binding concentration) of no more than 0.01 nM, no more than 0.02 nM, no more than 0.03 nM, no more than 0.04 nM, no more than 0.05 nM, no more than 0.06 nM, no more than 0.07 nM or no more than 0.08 nM by ELISA. In certain embodiments, the antibodies and the fragments thereof provided herein specifically bind to human CD3epsilon expressed on surface of cells at an $EC_{50}$ of no more than 0.5 nM, no more than 0.6 nM, no more than 0.7 nM, no more than 0.8 nM, no more than 0.9 nM, no more than 1 nM, no more than 2 nM, no more than 3 nM, no more than 4 nM, no more than 5 nM, no more than 6 nM, no more than 7 nM, no more than 8 nM, no more than 9 nM or no more than 10 nM by flow cytometry assay.

In certain embodiments, the antibodies and antigen-binding fragments thereof bind to Cynomolgus monkey CD3epsilon with a binding affinity similar to that of human CD3epsilon. For example, binding of the exemplary antibodies WBP3311_2.166.48, WBP3311_2.306.4, WBP3311_2.383.47, WBP3311_2.400.5, WBP3311_2.482.5, WBP3311_2.488.33, WBP3311_2.615.8, WBP3311_2.844.8 to Cynomolgus monkey CD3epsilon is at a similar affinity or $EC_{50}$ value to that of human CD3epsilon.

In certain embodiments, the antibodies and the fragments thereof provided herein specifically bind to recombinant Cynomolgus monkey CD3epsilon with an $EC_{50}$ of no more than 0.001 nM, no more than 0.005 nM, no more than 0.01 nM, no more than 0.02 nM, no more than 0.03 nM, no more than 0.04 nM, or no more than 0.05 nM by ELISA.

In certain embodiments, the antibodies and the fragments thereof provided herein have a specific binding affinity to human CD3epsilon which is sufficient to provide for diagnostic and/or therapeutic use. A number of therapeutic strategies modulate T cell immunity by targeting TCR signaling, particularly by anti-human CD3 monoclonal antibodies that are clinically used.

The antibodies or antigen-binding fragments thereof provided herein can be a monoclonal antibody, polyclonal antibody, humanized antibody, chimeric antibody, recombinant antibody, bispecific antibody, labeled antibody, bivalent antibody, or anti-idiotypic antibody. A recombinant antibody is an antibody prepared in vitro using recombinant methods rather than in animals.

Antibody Variants

The present disclosure also encompasses various variants of the antibodies and antigen-binding fragments thereof provided herein. In certain embodiments, the present disclosure encompasses various types of variants of an exemplary antibody provided herein, i.e., WBP3311_2.166.48, WBP3311_2.306.4, WBP3311_2.383.47, WBP3311_2.400.5, WBP3311_2.482.5, WBP331_2.488.33, WBP3311_2.615.8, and WBP3311_2.844.8.

In certain embodiments, the antibody variants comprise one or more modifications or substitutions in one or more CDR sequences as provided in Table 1, one or more FR sequences provided in Table 2, the heavy or light chain variable region sequences provided herein, and/or the constant region (e.g. Fc region). Such variants retain specific binding affinity to CD3epsilon of their parent antibodies, but have one or more desirable properties conferred by the modification(s) or substitution(s). For example, the antibody variants may have improved antigen-binding affinity, improved glycosylation pattern, reduced risk of glycosylation, reduced deamination, reduced or depleted effector function(s), improved FcRn receptor binding, increased pharmacokinetic half-life, pH sensitivity, and/or compatibility to conjugation (e.g. one or more introduced cysteine residues).

The parent antibody sequence may be screened to identify suitable or preferred residues to be modified or substituted, using methods known in the art, for example "alanine scanning mutagenesis" (see, for example, Cunningham and Wells (1989) Science, 244:1081-1085). Briefly, target residues (e.g., charged residues such as Arg, Asp, His, Lys, and Glu) can be identified and replaced by a neutral or negatively charged amino acid (e.g., alanine or polyalanine), and the modified antibodies are produced and screened for the interested property. If substitution at a particular amino acid location demonstrates an interested functional change, then the position can be identified as a potential residue for modification or substitution. The potential residues may be further assessed by substituting with a different type of residue (e.g. cysteine residue, positively charged residue, etc.).

Affinity Variant

Affinity variant may contain modifications or substitutions in one or more CDR sequences as provided in Table 1, one or more FR sequences provided in Table 2, or the heavy or light chain variable region sequences provided herein. The affinity variants retain specific binding affinity to CD3epsilon of the parent antibody, or even have improved CD3epsilon specific binding affinity over the parent antibody. In certain embodiments, at least one (or all) of the substitution(s) in the CDR sequences, FR sequences, or variable region sequences comprises a conservative substitution.

A skilled artisan will understand that in the CDR sequences and FR sequences provided in Table 1 and Table 2, one or more amino acid residues may be substituted yet the resulting antibody or antigen-binding fragment still retain the binding affinity to CD3epsilon, or even have an improved binding affinity. Various methods known in the art can be used to achieve this purpose. For example, a library of antibody variants (such as Fab or scFv variants) can be generated and expressed with phage display technology, and then screened for the binding affinity to human CD3epsilon. For another example, computer software can be used to virtually simulate the binding of the antibodies to human CD3epsilon, and identify the amino acid residues on the antibodies which form the binding interface. Such residues may be either avoided in the substitution so as to prevent reduction in binding affinity, or targeted for substitution to provide for a stronger binding.

In certain embodiments, the humanized antibody or antigen-binding fragment provided herein comprises one or more amino acid residue substitutions in one or more CDR sequences, and/or one or more FR sequences. In certain embodiments, an affinity variant comprises no more than 10, 9, 8, 7, 6, 5, 4, 3, 2, or 1 substitutions in the CDR sequences and/or FR sequences in total.

In certain embodiments, the anti-CD3epsilon antibodies and antigen-binding fragments thereof comprise 1, 2, or 3 CDR sequences having at least 80% (e.g. at least 85%, 88%, 90%, 91%, 92%, 93%, 94%, 95%, 96%, 97%, 98%, 99%) sequence identity to that (or those) listed in Table 1, and in the meantime retain the binding affinity to CD3epsilon at a level similar to or even higher than its parent antibody.

In certain embodiments, the anti-CD3epsilon antibodies and antigen-binding fragments thereof comprise one or more FR sequences having at least 80% (e.g. at least 85%, 88%, 900%, 91%, 92%, 93%, 94%, 95%, 96%, 97%, 98%, 99%) sequence identity to that (or those) listed in Table 2, and in the meantime retain the binding affinity to CD3epsilon at a level similar to or even higher than its parent antibody.

In certain embodiments, the anti-CD3epsilon antibodies and antigen-binding fragments thereof comprise one or more variable region sequences having at least 80% (e.g. at least 85%, 88%, 90%, 91%, 92%, 93%, 94%, 95%, 96%, 97%, 98%, 99%) sequence identity to that (or those) listed in SEQ ID NO: 81, SEQ ID NO: 85, SEQ ID NO: 89, SEQ ID NO: 93, SEQ ID NO: 97, SEQ ID NO: 101, SEQ ID NO: 105, SEQ ID NO: 109, SEQ ID NO: 113, SEQ ID NO: 117, SEQ ID NO: 83, SEQ ID NO: 87, SEQ ID NO: 91, SEQ ID NO: 95, SEQ ID NO: 99, SEQ ID NO: 103, SEQ ID NO: 107, SEQ ID NO: 111, SEQ ID NO: 115, SEQ ID NO: 119, and in the meantime retain the binding affinity to CD3epsilon at a level similar to or even higher than its parent antibody. In some embodiments, a total of 1 to 10 amino acids have been substituted, inserted, or deleted in a sequence selected from SEQ ID NO: 81, SEQ ID NO: 85, SEQ ID NO: 89, SEQ ID NO: 93, SEQ ID NO: 97, SEQ ID NO: 101, SEQ ID NO: 105, SEQ ID NO: 109, SEQ ID NO: 113, SEQ ID NO: 117, SEQ ID NO: 83, SEQ ID NO: 87, SEQ ID NO: 91, SEQ ID NO: 95, SEQ ID NO: 99, SEQ ID NO: 103, SEQ ID NO: 107, SEQ ID NO: 111, SEQ ID NO: 115, and SEQ ID NO: 119. In some embodiments, the substitutions, insertions, or deletions occur in regions outside the CDRs (i.e., in the FRs).

Glycosylation Variant

The anti-CD3epsilon antibodies and antigen-binding fragments provided herein also encompass a glycosylation variant, which can be obtained to either increase or decrease the extent of glycosylation of the antibody or antigen binding fragment.

The antibody or antigen binding fragment thereof may comprise one or more amino acid residues with a side chain to which a carbohydrate moiety (e.g. an oligosaccharide structure) can be attached. Glycosylation of antibodies is typically either N-linked or O-linked. N-linked refers to the attachment of the carbohydrate moiety to the side chain of an asparagine residue, for example, an asparagine residue in a tripeptide sequence such as asparagine-X-serine and asparagine-X-threonine, where X is any amino acid except proline. O-linked glycosylation refers to the attachment of one of the sugars N-aceylgalactosamine, galactose, or xylose to a hydroxyamino acid, most commonly to serine or threonine. Removal of a native glycosylation site can be conveniently accomplished, for example, by altering the amino acid sequence such that one of the above-described tripeptide sequences (for N-linked glycosylation sites) or serine or threonine residues (for O-linked glycosylation sites) present in the sequence is substituted. A new glycosylation site can be created in a similar way by introducing such a tripeptide sequence or serine or threonine residue.

Cysteine-Engineered Variant

The anti-CD3epsilon antibodies and antigen-binding fragments provided herein also encompass a cysteine-engineered variant, which comprises one or more introduced free cysteine amino acid residues.

A free cysteine residue is one which is not part of a disulfide bridge. A cysteine-engineered variant is useful for conjugation with for example, a cytotoxic and/or imaging compound, a label, or a radioisoptype among others, at the site of the engineered cysteine, through for example a maleimide or haloacetyl. Methods for engineering antibodies or antigen-binding fragments to introduce free cysteine residues are known in the art, see, for example, WO2006/034488.

Fc Variant

The anti-CD3epsilon antibodies and antigen-binding fragments provided herein also encompass an Fc variant, which comprises one or more amino acid residue modifications or substitutions at its Fc region and/or hinge region.

In certain embodiments, the anti-CD3epsilon antibodies or antigen-binding fragments comprise one or more amino acid substitution(s) that improves pH-dependent binding to neonatal Fc receptor (FcRn). Such a variant can have an extended pharmacokinetic half-life, as it binds to FcRn at acidic pH which allows it to escape from degradation in the lysosome and then be translocated and released out of the cell. Methods of engineering an antibody and antigen-binding fragment thereof to improve binding affinity with FcRn are well-known in the art, see, for example, Vaughn, D. et al, Structure, 6(1): 63-73, 1998; Kontermann, R. et al, Antibody Engineering, Volume 1, Chapter 27: Engineering of the Fc region for improved PK, published by Springer, 2010; Yeung, Y. et al, Cancer Research, 70: 3269-3277 (2010); and Hinton, P. et al, J. Immunology, 176:346-356 (2006).

In certain embodiments, the anti-CD3epsilon antibodies or antigen-binding fragments comprise one or more amino acid substitution(s) that alters the antibody-dependent cellular cytotoxicity (ADCC). Certain amino acid residues at CH2 domain of the Fc region can be substituted to provide for enhanced ADCC activity. Alternatively or additionally, carbohydrate structures on the antibody can be changed to enhance ADCC activity. Methods of altering ADCC activity by antibody engineering have been described in the art, see for example, Shields R L. et al., J Biol Chem. 2001. 276(9): 6591-604; Idusogie E E. et al., J Immunol. 2000.164(8): 4178-84; Steurer W. et al., J Immunol. 1995, 155(3): 1165-74; Idusogie E E. et al., J Immunol. 2001, 166(4): 2571-5; Lazar G A. et al., PNAS, 2006, 103(11): 4005-4010; Ryan M C. et al., Mol. Cancer Ther., 2007, 6: 3009-3018; Richards J O. et al., Mol Cancer Ther. 2008, 7(8): 2517-27; Shields R. L. et al, J. Biol. Chem, 2002, 277: 26733-26740; Shinkawa T. et al, J. Biol. Chem, 2003, 278: 3466-3473.

In certain embodiments, the anti-CD3epsilon antibodies or antigen-binding fragments comprise one or more amino acid substitution(s) that alters Complement Dependent Cytotoxicity (CDC), for example, by improving or diminishing C1q binding and/or CDC (see, for example, WO99/51642; Duncan & Winter Nature 322:738-40 (1988); U.S. Pat. Nos. 5,648,260; 5,624,821); and WO94/29351 concerning other examples of Fc region variants.

In certain embodiments, the anti-CD3epsilon antibodies or antigen-binding fragments comprise one or more amino acid substitution(s) in the interface of the Fc region to facilitate and/or promote heterodimerization. These modifications comprise introduction of a protuberance into a first Fc polypeptide and a cavity into a second Fc polypeptide, wherein the protuberance can be positioned in the cavity so as to promote interaction of the first and second Fc polypeptides to form a heterodimer or a complex. Methods of generating antibodies with these modifications are known in the art, e.g., as described in U.S. Pat. No. 5,731,168.

Antigen-Binding Fragments

Provided herein are also anti-CD3epsilon antigen-binding fragments. Various types of antigen-binding fragments are known in the art and can be developed based on the anti-CD3epsilon antibodies provided herein, including for example, the exemplary antibodies whose CDR and FR sequences are shown in Tables 1 and 2, and their different variants (such as affinity variants, glycosylation variants, Fc variants, cysteine-engineered variants and so on).

In certain embodiments, an anti-CD3epsilon antigen-binding fragment provided herein is a camelized single domain antibody, a diabody, a single chain Fv fragment (scFv), an scFv dimer, a BsFv, a dsFv, a (dsFv)$_2$, a dsFv-dsFv', an Fv fragment, a Fab, a Fab', a F(ab')$_2$, a bispecific antibody, a ds diabody, a nanobody, a domain antibody, a single domain antibody, or a bivalent domain antibody.

Various techniques can be used for the production of such antigen-binding fragments. Illustrative methods include, enzymatic digestion of intact antibodies (see, e.g., Morimoto et al., Journal of Biochemical and Biophysical Methods 24:107-117 (1992); and Brennan et al., Science, 229:81 (1985)), recombinant expression by host cells such as E. Coli (e.g. for Fab, Fv and ScFv antibody fragments), screening from a phage display library as discussed above (e.g. for ScFv), and chemical coupling of two Fab'-SH fragments to form F(ab')$_2$ fragments (Carter et al., Bio/Technology 10:163-167 (1992)). Other techniques for the production of antibody fragments will be apparent to a skilled practitioner.

In certain embodiments, the antigen-binding fragment is a scFv. Generation of scFv is described in, for example, WO 93/16185; U.S. Pat. Nos. 5,571,894; and 5,587,458. scFv may be fused to an effector protein at either the amino or the carboxy terminus to provide for a fusion protein (see, for example, Antibody Engineering, ed. Borrebaeck).

Bispecific Antibodies, Multivalent Antibodies

In certain embodiments, the antibodies and antigen-binding fragments thereof provided herein are bivalent, tetravalent, hexavalent, or multivalent. In certain embodiments, the antibodies and antigen-binding fragments thereof provided herein are monospecific, or bispecific.

The term "valent" as used herein refers to the presence of a specified number of antigen binding sites in a given molecule. As such, the terms "bivalent", "tetravalent", and "hexavalent" denote the presence of two binding site, four binding sites, and six binding sites, respectively, in an antigen-binding molecule. A bivalent molecule can be monospecific if the two binding sites are both for specific binding of the same antigen or the same epitope. Similarly, a trivalent molecule can be bispecific, for example, when two binding sites are monospecific for a first antigen (or epitope) and the third binding site is specific for a second antigen (or epitope).

In certain embodiments, the antibodies and antigen-binding fragments thereof provided herein can be monospecific but bivalent, trivalent, or tetravalent, with at least two binding sites specific for the same antigen or epitope. This, in certain embodiments, provides for stronger binding to the antigen or the epitope than a monovalent counterpart. In certain embodiments, in a bivalent antigen-binding moiety, the first valent of binding site and the second valent of binding site are structurally identical (i.e. having the same sequences), or structurally different (i.e. having different sequences albeit with the same specificity).

In certain embodiments, the antibodies and antigen-binding fragments thereof provided herein are bispecific. In some embodiments, the bispecific antibodies and antigen-binding fragments thereof provided herein has a first specificity for CD3epsilon, and a second specificity. In some embodiments, the second specificity is for CD3epsilon but to different epitopes. In some embodiments, the second specificity is for a second antigen different from CD3epsilon and whose presence in proximity to CD3epsilon-expressing T cells is desirable for the second antigen to be recognized by immune system. For example, bringing CD3epsilon-expressing T cells in close proximity to a tumor antigen or a pathogen antigen and hence promoting recognition or elimination of such an antigen by the immune system.

In certain embodiments, the second specificity is for a tumor associated antigen or an epitope thereof. The term "tumor associated antigen" refers to an antigen that is or can be presented on a tumor cell surface and that is located on or within tumor cells. In some embodiments, the tumor associated antigens can be presented only by tumor cells and not by normal, i.e. non-tumor cells. In some other embodiments, the tumor associated antigens can be exclusively expressed on tumor cells or may represent a tumor specific mutation compared to non-tumor cells. In some other embodiments, the tumor associated antigens can be found in both tumor cells and non-tumor cells, but is overexpressed on tumor cells when compared to non-tumor cells or are accessible for antibody binding in tumor cells due to the less compact structure of the tumor tissue compared to non-tumor tissue. In some embodiments, the tumor associated antigen is located on the vasculature of a tumor.

Illustrative examples of a tumor associated antigen are CD10, CD19, CD20, CD21, CD22, CD25, CD30, CD33, CD34, CD37, CD44v6, CD45, CD133, Fms-like tyrosine kinase 3 (FLT-3, CD135), chondroitin sulfate proteoglycan 4 (CSPG4, melanoma-associated chondroitin sulfate proteoglycan), Epidermal growth factor receptor (EGFR), Her2, Her3, IGFR, IL3R, fibroblast activating protein (FAP), CDCP1, Derlin1, Tenascin, frizzled 1-10, the vascular antigens VEGFR2 (KDR/FLK 1), VEGFR3 (FLT4, CD309), PDGFR-alpha (CD140a), PDGFR-beta (CD140b), Endoglin, CLEC 14, Tem 1-8, and Tie2. Further examples may include A33, CAMPATH-1 (CDw52), Carcinoembryonic antigen (CEA), Carboanhydrase IX (MN/CA IX), de2-7, EGFR, EGFRvIII, EpCAM, Ep-CAM, Folate-binding protein, G250, Fms-like tyrosine kinase 3 (FLT-3, CD135), c-Kit (CD117), CSF1R (CD115), HLA-DR, IGFR, IL-2 receptor, IL3R, MCSP (Melanoma-associated cell surface chondroitin sulphate proteoglycane), Muc-1, Prostate-specific membrane antigen (PSMA), Prostate stem cell antigen (PSCA), Prostate specific antigen (PSA), and TAG-72.

The bispecific antibodies and antigen-binding fragments provided herein can be made with any suitable methods known in the art. In a conventional approach, two immunoglobulin heavy chain-light chain pairs having different antigenic specificities can be co-expressed in a host cell to produce bispecific antibodies in a recombinant way (see, for example, Milstein and Cuello, Nature, 305: 537 (1983)), followed by purification by affinity chromatography.

Recombinant approach may also be used, where sequences encoding the antibody heavy chain variable domains for the two specificities are respectively fused to immunoglobulin constant domain sequences, followed by insertion to an expression vector which is co-transfected with an expression vector for the light chain sequences to a suitable host cell for recombinant expression of the bispecific antibody (see, for example, WO 94/04690; Suresh et al., Methods in Enzymology, 121:210 (1986)). Similarly, scFv dimers can also be recombinantly constructed and expressed from a host cell (see, e.g. Gruber et al., J. Immunol., 152:5368 (1994).)

In another method, leucine zipper peptides from the Fos and Jun proteins can be linked to the Fab' portions of two different antibodies by gene fusion. The linked antibodies are reduced at the hinge region to four half antibodies (i.e. monomers) and then re-oxidized to form heterodimers (Kostelny et al., J. Immunol., 148(5):1547-1553 (1992)).

The two antigen-binding domains may also be conjugated or cross-linked to form a bispecific antibody or antigen-binding fragment. For example, one antibody can be coupled to biotin while the other antibody to avidin, and the strong association between biotin and avidin would complex the two antibodies together to form a bispecific antibody (see, for example, U.S. Pat. No. 4,676,980; WO 91/00360, WO 92/00373, and EP 03089). For another example, the two antibodies or antigen-binding fragments can be cross-linked by conventional methods known in the art, for example, as disclosed in U.S. Pat. No. 4,676,980.

Bispecific antigen-binding fragments may be generated from a bispecific antibody, for example, by proteolytic cleavage, or by chemical linking. For example, an antigen-binding fragment (e.g. Fab') of an antibody may be prepared and converted to Fab'-thiol derivative and then mixed and reacted with another converted Fab' derivative having a different antigenic specificity to form a bispecific antigen-binding fragment (see, for example, Brennan et al., Science, 229: 81 (1985)).

In certain embodiments, the bispecific antibody or antigen-binding fragments may be engineered at the interface so that a knob-into-hole association can be formed to promote heterodimerization of the two different antigen-binding sites. "Knob-into-hole" as used herein, refers to an interaction between two polypeptides (such as CH3 domain), where one polypeptide has a protuberance (i.e. "knob") due to presence of an amino acid residue having a bulky side chain (e.g. tyrosine or tryptophan), and the other polypeptide has a cavity (i.e. "hole") where a small side chain amino acid residue resides (e.g. alanine or threonine), and the protuberance is positionable in the cavity so as to promote interaction of the two polypeptides to form a heterodimer or a complex. Methods of generating polypeptides with knobs-into-holes are known in the art, e.g., as described in U.S. Pat. No. 5,731,168.

Conjugates

In some embodiments, the anti-CD3epsilon antibodies and antigen-binding fragments thereof further comprise a conjugate. The conjugate can be linked to the antibodies and antigen-binding fragments thereof. A conjugate is a non-proteinaceous moiety that can be attached to the antibody or antigen-binding fragment thereof. It is contemplated that a variety of conjugates may be linked to the antibodies or antigen-binding fragments provided herein (see, for example, "Conjugate Vaccines", Contributions to Microbiology and Immunology, J. M. Cruse and R. E. Lewis, Jr. (eds.), Carger Press, New York, (1989)). These conjugates may be linked to the antibodies or antigen-binding fragments by covalent binding, affinity binding, intercalation, coordinate binding, complexation, association, blending, or addition, among other methods.

In certain embodiments, the antibodies and antigen-binding fragments disclosed herein may be engineered to contain specific sites outside the epitope binding portion that may be utilized for binding to one or more conjugates. For example, such a site may include one or more reactive amino acid residues, such as for example cysteine or histidine residues, to facilitate covalent linkage to a conjugate.

In certain embodiments, the antibodies may be linked to a conjugate indirectly, or through another conjugate. For example, the antibody or antigen-binding fragments may be conjugated to biotin, then indirectly conjugated to a second conjugate that is conjugated to avidin. The conjugate can be a toxin (e.g., a chemotherapeutic agent), a detectable label (e.g., a radioactive isotope, a lanthanide, a luminescent label, a fluorescent label, or an enzyme-substrate label).

A "toxin" can be any agent that is detrimental to cells or that can damage or kill cells. Examples of toxin include, without limitation, taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, puromycin and analogs thereof, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

Examples of detectable label may include a fluorescent labels (e.g. fluorescein, rhodamine, dansyl, phycoerythrin, or Texas Red), enzyme-substrate labels (e.g. horseradish peroxidase, alkaline phosphatase, luceriferases, glucoamylase, lysozyme, saccharide oxidases or β-D-galactosidase), radioisotopes (e.g. $^{123}I$, $^{124}I$, $^{125}I$, $^{131}I$, $^{35}S$, $^{3}H$, $^{111}In$, $^{112}In$, $^{14}C$, $^{64}Cu$, $^{67}Cu$, $^{86}Y$, $^{88}Y$, $^{90}Y$, $^{177}Lu$, $^{211}At$, $^{186}Re$, $^{188}Re$, $^{153}Sm$, $^{212}Bi$, and $^{32}P$, other lanthanides, luminescent labels), chromophoric moiety, digoxigenin, biotin/avidin, a DNA molecule or gold for detection.

In certain embodiments, the conjugate can be a pharmacokinetic modifying moiety which helps increase half-life of the antibody. Illustrative example include water-soluble polymers, such as PEG, carboxymethylcellulose, dextran, polyvinyl alcohol, polyvinyl pyrrolidone, copolymers of ethylene glycol/propylene glycol, and the like. The polymer may be of any molecular weight, and may be branched or unbranched. The number of polymers attached to the antibody may vary, and if more than one polymer are attached, they can be the same or different molecules.

In certain embodiments, the conjugate can be a purification moiety such as a magnetic bead.

In certain embodiments, the antibodies and antigen-binding fragments thereof provided herein is used for a base for a conjugate.

Polynucleotides and Recombinant Methods

The present disclosure provides isolated polynucleotides that encode the anti-CD3epsilon antibodies and antigen-binding fragments thereof. In certain embodiments, the isolated polynucleotides comprise one or more nucleotide sequences as shown in SEQ IN NO: 82, 84, 86, 88, 90, 92, 94, 96, 98, 100, 102, 104, 106, 108, 110, 112, 114, 116, 118, and/or 120, which encodes the variable region of the exemplary antibodies provided herein. DNA encoding the monoclonal antibody is readily isolated and sequenced using conventional procedures (e.g., by using oligonucleotide probes that are capable of binding specifically to genes encoding the heavy and light chains of the antibody). The encoding DNA may also be obtained by synthetic methods.

The isolated polynucleotide that encodes the anti-CD3epsilon antibodies and antigen-binding fragments thereof (e.g. including the sequences in as shown in SEQ IN NO: 82, 84, 86, 88, 90, 92, 94, 96, 98, 100, 102, 104, 106, 108, 110, 112, 114, 116, 118, and/or 120) can be inserted into a vector for further cloning (amplification of the DNA) or for expression, using recombinant techniques known in the art. Many vectors are available. The vector components generally include, but are not limited to, one or more of the following: a signal sequence, an origin of replication, one or more marker genes, an enhancer element, a promoter (e.g. SV40, CMV, EF-1α), and a transcription termination sequence.

In some embodiments, the vector system includes mammalian, bacterial, yeast systems, etc, and comprises plasmids such as, but not limited to, pALTER, pBAD, pcDNA, pCal, pL, pET, pGEMEX, pGEX, pCI, pCMV, pEGFP, pEGFT, pSV2, pFUSE, pVITRO, pVIVO, pMAL, pMD18-T, pMONO, pSELECT, pUNO, pDUO, Psg5L, pBABE, pWPXL, pBI, p15TV-L, pPro18, pTD, pRS420, pLexA, pACT2.2 etc, and other laboratorial and commercially available suitable vectors may include, plasmid, or viral vectors (e.g., replication defective retroviruses, adenoviruses and adeno-associated viruses).

Vectors comprising the polynucleotide sequence encoding the antibody or antigen-binding fragment can be introduced to a host cell for cloning or gene expression. Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, for example, Enterobacteriaceae such as *Escherichia*, e.g., *E. coli*, *Enterobacter*, *Erwinia*, *Klebsiella*, *Proteus*, *Salmonella*, e.g., *Salmonella typhimurium*, *Serratia*, e.g., *Serratia marcescans*, and *Shigella*, as well as Bacilli such as *B. subtilis* and *B. licheniformis*, *Pseudomonas* such as *P. aeruginosa*, and *Streptomyces*.

In addition to prokaryotes, eukaryotic microbes such as filamentous fungi or yeast are suitable cloning or expression hosts for anti-CD3epsilon antibody-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe*; *Kluyveromyces* hosts such as, e.g., *K. lactis*, *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus*; *yarrowia* (EP 402,226); *Pichia pastoris* (EP 183,070); *Candida*; *Trichoderma reesia* (EP 244,234); *Neurospora crassa*; *Schwanniomyces* such as *Schwanniomyces occidentalis*; and filamentous fungi such as, e.g., *Neurospora*, *Penicillium*, *Tolypocladium*, and *Aspergillus* hosts such as *A. nidulans* and *A. niger*.

Suitable host cells for the expression of glycosylated antibodies or antigen-fragment provided here are derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruiffly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells. Plant cell cultures of cotton, corn, potato, soybean, petunia, tomato, and tobacco can also be utilized as hosts.

However, interest has been greatest in vertebrate cells, and propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., J. Gen Virol. 36:59 (1977)); baby hamster kidney cells (BHK, ATCC CCL 10); Chinese hamster ovary cells/-DHFR (CHO, Urlaub et al., Proc. Natl. Acad. Sci. USA 77:4216 (1980)); mouse sertoli cells (TM4, Mather, Biol. Reprod. 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci. 383:44-68

(1982)); MRC 5 cells; FS4 cells; and a human hepatoma line (Hep G2). In some preferable embodiments, the host cell is 293F cell.

Host cells are transformed with the above-described expression or cloning vectors for anti-CD3epsilon antibody production and cultured in conventional nutrient media modified as appropriate for inducing promoters, selecting transformants, or amplifying the genes encoding the desired sequences. In another embodiment, the antibody may be produced by homologous recombination known in the art.

The host cells used to produce the antibodies or antigen-binding fragments provided herein may be cultured in a variety of media. Commercially available media such as Ham's F10 (Sigma), Minimal Essential Medium (MEM), (Sigma), RPMI-1640 (Sigma), and Dulbecco's Modified Eagle's Medium (DMEM), Sigma) are suitable for culturing the host cells. In addition, any of the media described in Ham et al., Meth. Enz. 58:44 (1979), Barnes et al., Anal. Biochem. 102:255 (1980), U.S. Pat. Nos. 4,767,704; 4,657,866; 4,927,762; 4,560,655; or 5,122,469; WO 90/03430; WO 87/00195; or U.S. Pat. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

When using recombinant techniques, the antibody can be produced intracellularly, in the periplasmic space, or directly secreted into the medium. If the antibody is produced intracellularly, as a first step, the particulate debris, either host cells or lysed fragments, is removed, for example, by centrifugation or ultrafiltration. Carter et al., Bio/Technology 10:163-167 (1992) describe a procedure for isolating antibodies which are secreted to the periplasmic space of E. coli. Briefly, cell paste is thawed in the presence of sodium acetate (pH 3.5), EDTA, and phenylmethylsulfonylfluoride (PMSF) over about 30 min. Cell debris can be removed by centrifugation. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The anti-CD3epsilon antibodies and antigen-binding fragments thereof prepared from the cells can be purified using, for example, hydroxylapatite chromatography, gel electrophoresis, dialysis, DEAE-cellulose ion exchange chromatography, ammonium sulfate precipitation, salting out, and affinity chromatography, with affinity chromatography being the preferred purification technique.

In certain embodiments, Protein A immobilized on a solid phase is used for immunoaffinity purification of the antibody and antigen-binding fragment thereof. The suitability of protein A as an affinity ligand depends on the species and isotype of any immunoglobulin Fc domain that is present in the antibody. Protein A can be used to purify antibodies that are based on human gamma1, gamma2, or gamma4 heavy chains (Lindmark et al., J. Immunol. Meth. 62:1-13 (1983)). Protein G is recommended for all mouse isotypes and for human gamma3 (Guss et al., EMBO J. 5:1567 1575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a CH3 domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5-4.5, preferably performed at low salt concentrations (e.g., from about 0-0.25M salt).

Pharmaceutical Composition

The present disclosure further provides pharmaceutical compositions comprising the anti-CD3epsilon antibodies or antigen-binding fragments thereof and one or more pharmaceutically acceptable carriers.

Pharmaceutical acceptable carriers for use in the pharmaceutical compositions disclosed herein may include, for example, pharmaceutically acceptable liquid, gel, or solid carriers, aqueous vehicles, nonaqueous vehicles, antimicrobial agents, isotonic agents, buffers, antioxidants, anesthetics, suspending/dispending agents, sequestering or chelating agents, diluents, adjuvants, excipients, or non-toxic auxiliary substances, other components known in the art, or various combinations thereof.

Suitable components may include, for example, antioxidants, fillers, binders, disintegrants, buffers, preservatives, lubricants, flavorings, thickeners, coloring agents, emulsifiers or stabilizers such as sugars and cyclodextrins. Suitable antioxidants may include, for example, methionine, ascorbic acid, EDTA, sodium thiosulfate, platinum, catalase, citric acid, cysteine, thioglycerol, thioglycolic acid, thiosorbitol, butylated hydroxanisol, butylated hydroxytoluene, and/or propyl gallate. As disclosed herein, inclusion of one or more antioxidants such as methionine in a composition comprising an antibody or antigen-binding fragment and conjugates as provided herein decreases oxidation of the antibody or antigen-binding fragment. This reduction in oxidation prevents or reduces loss of binding affinity, thereby improving antibody stability and maximizing shelf-life. Therefore, in certain embodiments compositions are provided that comprise one or more antibodies or antigen-binding fragments as disclosed herein and one or more antioxidants such as methionine. Further provided are methods for preventing oxidation of, extending the shelf-life of, and/or improving the efficacy of an antibody or antigen-binding fragment as provided herein by mixing the antibody or antigen-binding fragment with one or more antioxidants such as methionine.

To further illustrate, pharmaceutical acceptable carriers may include, for example, aqueous vehicles such as sodium chloride injection, Ringer's injection, isotonic dextrose injection, sterile water injection, or dextrose and lactated Ringer's injection, nonaqueous vehicles such as fixed oils of vegetable origin, cottonseed oil, corn oil, sesame oil, or peanut oil, antimicrobial agents at bacteriostatic or fungistatic concentrations, isotonic agents such as sodium chloride or dextrose, buffers such as phosphate or citrate buffers, antioxidants such as sodium bisulfate, local anesthetics such as procaine hydrochloride, suspending and dispersing agents such as sodium carboxymethylcelluose, hydroxypropyl methylcellulose, or polyvinylpyrrolidone, emulsifying agents such as Polysorbate 80 (TWEEN-80), sequestering or chelating agents such as EDTA (ethylenediaminetetraacetic acid) or EGTA (ethylene glycol tetraacetic acid), ethyl alcohol, polyethylene glycol, propylene glycol, sodium hydroxide, hydrochloric acid, citric acid, or lactic acid. Antimicrobial agents utilized as carriers may be added to pharmaceutical compositions in multiple-dose containers that include phenols or cresols, mercurials, benzyl alcohol, chlorobutanol, methyl and propyl p-hydroxybenzoic acid esters, thimerosal, benzalkonium chloride and benzethonium chloride. Suitable excipients may include, for example, water, saline, dextrose, glycerol, or ethanol. Suitable non-toxic auxiliary substances may include, for example, wetting or emulsifying agents, pH buffering agents, stabilizers, solubility enhancers, or agents such as sodium acetate, sorbitan monolaurate, triethanolamine oleate, or cyclodextrin.

The pharmaceutical compositions can be a liquid solution, suspension, emulsion, pill, capsule, tablet, sustained release formulation, or powder. Oral formulations can include standard carriers such as pharmaceutical grades of mannitol, lactose, starch, magnesium stearate, polyvinyl pyrollidone, sodium saccharine, cellulose, magnesium carbonate, etc.

In certain embodiments, the pharmaceutical compositions are formulated into an injectable composition. The injectable pharmaceutical compositions may be prepared in any conventional form, such as for example liquid solution, suspension, emulsion, or solid forms suitable for generating liquid solution, suspension, or emulsion. Preparations for injection may include sterile and/or non-pyretic solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use, and sterile and/or non-pyretic emulsions. The solutions may be either aqueous or nonaqueous.

In certain embodiments, unit-dose parenteral preparations are packaged in an ampoule, a vial or a syringe with a needle. All preparations for parenteral administration should be sterile and not pyretic, as is known and practiced in the art.

In certain embodiments, a sterile, lyophilized powder is prepared by dissolving an antibody or antigen-binding fragment as disclosed herein in a suitable solvent. The solvent may contain an excipient which improves the stability or other pharmacological components of the powder or reconstituted solution, prepared from the powder. Excipients that may be used include, but are not limited to, water, dextrose, sorbital, fructose, corn syrup, xylitol, glycerin, glucose, sucrose or other suitable agent. The solvent may contain a buffer, such as citrate, sodium or potassium phosphate or other such buffer known to those of skill in the art at, in one embodiment, about neutral pH. Subsequent sterile filtration of the solution followed by lyophilization under standard conditions known to those of skill in the art provides a desirable formulation. In one embodiment, the resulting solution will be apportioned into vials for lyophilization. Each vial can contain a single dosage or multiple dosages of the anti-CD3epsilon antibody or antigen-binding fragment thereof or composition thereof. Overfilling vials with a small amount above that needed for a dose or set of doses (e.g., about 10%) is acceptable so as to facilitate accurate sample withdrawal and accurate dosing. The lyophilized powder can be stored under appropriate conditions, such as at about 4° C. to room temperature.

Reconstitution of a lyophilized powder with water for injection provides a formulation for use in parenteral administration. In one embodiment, for reconstitution the sterile and/or non-pyretic water or other liquid suitable carrier is added to lyophilized powder. The precise amount depends upon the selected therapy being given, and can be empirically determined.

Methods of Use

The present disclosure also provides therapeutic methods comprising: administering a therapeutically effective amount of the antibody or antigen-binding fragment as provided herein to a subject in need thereof, thereby treating or preventing a CD3-related condition or a disorder. In some embodiment, the CD3-related condition or a disorder is cancer, autoimmune disease, inflammatory disease, or infectious disease.

Examples of cancer include but are not limited to, non-small cell lung cancer (squamous/nonsquamous), small cell lung cancer, renal cell cancer, colorectal cancer, colon cancer, ovarian cancer, breast cancer (including basal breast carcinoma, ductal carcinoma and lobular breast carcinoma), pancreatic cancer, gastric carcinoma, bladder cancer, esophageal cancer, mesothelioma, melanoma, head and neck cancer, thyroid cancer, sarcoma, prostate cancer, glioblastoma, cervical cancer, thymic carcinoma, melanoma, myelomas, mycoses fungoids, merkel cell cancer, hepatocellular carcinoma (HCC), fibrosarcoma, myxosarcoma, liposarcoma, chondrosarcoma, osteogenic sarcoma, and other sarcomas, synovioma, mesothelioma, Ewing's tumor, leiomyosarcoma, rhabdomyosarcoma, lymphoid malignancy, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, hepatoma, bile duct carcinoma, choriocarcinoma, Wilms' tumor, cervical cancer, testicular tumor, seminoma, classical Hodgkin lymphoma (CHL), primary mediastinal large B-cell lymphoma, T-cell/histiocyte-rich B-cell lymphoma, acute lymphocytic leukemia, acute myelocytic leukemia, acute myelogenous leukemia, chronic myelocytic (granulocytic) leukemia, chronic myelogenous leukemia, chronic lymphocytic leukemia, polycythemia vera, mast cell derived tumors, EBV-positive and -negative PTLD, and diffuse large B-cell lymphoma (DLBCL), plasmablastic lymphoma, extranodal NK/T-cell lymphoma, nasopharyngeal carcinoma, HHV8-associated primary effusion lymphoma, non-Hodgkin's lymphoma, multiple myeloma, Waldenstrom's macroglobulinemia, heavy chain disease, myelodysplastic syndrome, hairy cell leukemia and myelodysplasia, primary CNS lymphoma, spinal axis tumor, brain stem glioma, astrocytoma, medulloblastoma, craniopharyogioma, ependymoma, pinealoma, hemangioblastoma, acoustic neuroma, oligodendroglioma, menangioma, melanoma, neuroblastoma and retinoblastoma.

Autoimmune diseases include, but are not limited to, Acquired Immunodeficiency Syndrome (AIDS, which is a viral disease with an autoimmune component), alopecia areata, ankylosing spondylitis, antiphospholipid syndrome, autoimmune Addison's disease, autoimmune hemolytic anemia, autoimmune hepatitis, autoimmune inner ear disease (AIED), autoimmune lymphoproliferative syndrome (ALPS), autoimmune thrombocytopenic purpura (ATP), Behcet's disease, cardiomyopathy, celiac sprue-dermatitis hepetiformis; chronic fatigue immune dysfunction syndrome (CFIDS), chronic inflammatory demyelinating polyneuropathy (CIPD), cicatricial pemphigold, cold agglutinin disease, crest syndrome, Crohn's disease, Degos' disease, dermatomyositis-juvenile, discoid lupus, essential mixed cryoglobulinemia, fibromyalgia-fibromyositis, Graves' disease, Guillain-Barre syndrome, Hashimoto's thyroiditis, idiopathic pulmonary fibrosis, idiopathic thrombocytopenia purpura (ITP), IgA nephropathy, insulin-dependent diabetes mellitus, juvenile chronic arthritis (Still's disease), juvenile rheumatoid arthritis, Meniere's disease, mixed connective tissue disease, multiple sclerosis, myasthenia gravis, pemacious anemia, polyarteritis nodosa, polychondritis, polyglandular syndromes, polymyalgia rheumatica, polymyositis and dermatomyositis, primary agammaglobulinemia, primary biliary cirrhosis, psoriasis, psoriatic arthritis. Raynaud's phenomena, Reiter's syndrome, rheumatic fever, rheumatoid arthritis, sarcoidosis, scleroderma (progressive systemic sclerosis (PSS), also known as systemic sclerosis (SS)), Sjogren's syndrome, stiff-man syndrome, systemic lupus erythematosus, Takayasu arteritis, temporal arteritis/giant cell arteritis, ulcerative colitis, uveitis, vitiligo and Wegener's granulomatosis. Inflammatory disorders, include, for example, chronic and acute inflammatory disorders. Examples of inflammatory disorders include Alzheimer's disease, asthma, atopic allergy, allergy, atherosclerosis, bronchial asthma, eczema, glomerulonephritis, graft vs. host disease, hemolytic anemias, osteoarthritis, sepsis, stroke, transplantation of tissue and organs, vasculitis, diabetic retinopathy and ventilator induced lung injury. In some embodiments, the CD3 associated conditions are inflammatory diseases such as systemic lupus erythematosus (SLE), intestinal mucosal inflammation, wasting disease associated with colitis, multiple sclerosis, viral infections, rheumatoid arthritis, osteoarthritis, Cohn's disease, and inflammatory bowel disease, psoriasis, systemic scleroderma, autoimmune diabetes and the like.

Infectious disease include, but are not limited to, fungus infection, parasite/protozoan infection or chronic viral infection, for example, malaria, coccidioiodmycosis immitis, histoplasmosis, onychomycosis, aspergilosis, blastomycosis, candidiasis albicans, paracoccidioiomycosis, microsporidiosis, *Acanthamoeba keratitis*, Amoebiasis, Ascariasis, Babesiosis, Balantidiasis, Baylisascariasis, Chagas disease, Clonorchiasis, Cochliomyia, Cryptosporidiosis, Diphyllobothriasis, Dracunculiasis, Echinococcosis, Elephantiasis, Enterobiasis, Fascioliasis, Fasciolopsiasis, Filariasis, Giardiasis, Gnathostomiasis, Hymenolepiasis, Isosporiasis, Katayama fever, Leishmaniasis, Lyme disease, Metagonimiasis, Myiasis, Onchocerciasis, Pediculosis, Scabies, Schistosomiasis, Sleeping sickness, Strongyloidiasis, Taeniasis, Toxocariasis, Toxoplasmosis, Trichinosis, Trichuriasis, Trypanosomiasis, helminth infection, infection of hepatitis B (HBV), hepatitis C (HCV), herpes virus, Epstein-Barr virus, HIV, cytomegalovirus, herpes simplex virus type I, herpes simplex virus type II, human papilloma virus, adenovirus, human immunodeficiency virus I, human immunodeficiency virus II, Kaposi West sarcoma associated herpes virus epidemics, thin ring virus (Torquetenovirus), human T lymphotrophic viruse I, human T lymphotrophic virus II, varicella zoster, JC virus or BK virus.

In another aspect, methods are provided to treat a condition in a subject that would benefit from upregulation of immune response, comprising administering a therapeutically effective amount of the antibody or antigen-binding fragment as provided herein to a subject in need thereof.

The therapeutically effective amount of an antibody or antigen-binding fragment as provided herein will depend on various factors known in the art, such as for example body weight, age, past medical history, present medications, state of health of the subject and potential for cross-reaction, allergies, sensitivities and adverse side-effects, as well as the administration route and extent of disease development. Dosages may be proportionally reduced or increased by one of ordinary skill in the art (e.g., physician or veterinarian) as indicated by these and other circumstances or requirements.

In certain embodiments, an antibody or antigen-binding fragment as provided herein may be administered at a therapeutically effective dosage of about 0.01 mg/kg to about 100 mg/kg (e.g., about 0.01 mg/kg, about 0.5 mg/kg, about 1 mg/kg, about 2 mg/kg, about 3 mg/kg, about 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 55 mg/kg, about 60 mg/kg, about 65 mg/kg, about 70 mg/kg, about 75 mg/kg, about 80 mg/kg, about 85 mg/kg, about 90 mg/kg, about 95 mg/kg, or about 100 mg/kg). In certain of these embodiments, the antibody or antigen-binding fragment is administered at a dosage of about 50 mg/kg or less, and in certain of these embodiments the dosage is 10 mg/kg or less, 5 mg/kg or less, 3 mg/kg or less, 1 mg/kg or less, 0.5 mg/kg or less, or 0.1 mg/kg or less. In certain embodiments, the administration dosage may change over the course of treatment. For example, in certain embodiments the initial administration dosage may be higher than subsequent administration dosages. In certain embodiments, the administration dosage may vary over the course of treatment depending on the reaction of the subject.

Dosage regimens may be adjusted to provide the optimum desired response (e.g., a therapeutic response). For example, a single dose may be administered, or several divided doses may be administered over time.

The antibodies and antigen-binding fragments disclosed herein may be administered by any route known in the art, such as for example parenteral (e.g., subcutaneous, intraperitoneal, intravenous, including intravenous infusion, intramuscular, or intradermal injection) or non-parenteral (e.g., oral, intranasal, intraocular, sublingual, rectal, or topical) routes.

In some embodiments, the antibodies or antigen-binding fragments disclosed herein may be administered alone or in combination with one or more additional therapeutic means or agents. For example, the antibodies or antigen-binding fragments disclosed herein may be administered in combination with another therapeutic agent, for example, an chemotherapeutic agent or an anti-cancer drug.

In certain of these embodiments, an antibody or antigen-binding fragment as disclosed herein that is administered in combination with one or more additional therapeutic agents may be administered simultaneously with the one or more additional therapeutic agents, and in certain of these embodiments the antibody or antigen-binding fragment and the additional therapeutic agent(s) may be administered as part of the same pharmaceutical composition. However, an antibody or antigen-binding fragment administered "in combination" with another therapeutic agent does not have to be administered simultaneously with or in the same composition as the agent. An antibody or antigen-binding fragment administered prior to or after another agent is considered to be administered "in combination" with that agent as the phrase is used herein, even if the antibody or antigen-binding fragment and second agent are administered via different routes. Where possible, additional therapeutic agents administered in combination with the antibodies or antigen-binding fragments disclosed herein are administered according to the schedule listed in the product information sheet of the additional therapeutic agent, or according to the Physicians' Desk Reference 2003 (Physicians' Desk Reference, 57th Ed; Medical Economics Company; ISBN: 1563634457; 57th edition (November 2002)) or protocols well known in the art.

The present disclosure further provides methods of using the anti-CD3epsilon antibodies or antigen-binding fragments thereof. In some embodiments, the present disclosure provides methods of activating CD3epsilon-expressing T cells in vivo or in vitro, comprising: contacting the CD3epsilon-expressing T cells with the antibody or antigen-binding fragment thereof provided herein. In some embodiments, the present disclosure provides methods of modulating CD3 activity in a CD3epsilon-expressing cell, comprising exposing the CD3epsilon-expressing cell to the antibody or antigen-binding fragment thereof provided herein.

In some embodiments, the present disclosure provides methods of promoting in vivo or in vitro processing of a second antigen by CD3epsilon-expressing T cell, comprising contacting the CD3epsilon-expressing T cells with the bispecific antibody or antigen-binding fragment thereof provided herein, wherein the bispecific antibody or antigen-binding fragment is capable of specifically binding to both the CD3epsilon-expressing T cells and a second antigen thereby bringing both in close proximity.

In some embodiments, the present disclosure provides methods of detecting presence or amount of CD3epsilon in a sample, comprising contacting the sample with the antibody or antigen-binding fragment thereof, and determining the presence or the amount of CD3epsilon in the sample.

In some embodiments, the present disclosure provides methods of diagnosing a CD3 related disease or condition in a subject, comprising: a) obtaining a sample from the subject; b) contacting the sample obtained from the subject with the antibody or antigen-binding fragment thereof provided herein; c) determining presence or amount of CD3epsilon in the sample; and d) correlating the existence of the CD3epsilon to the CD3 related disease or condition in the subject.

In some embodiments, the present disclosure also provides use of the antibody or antigen-binding fragment thereof provided herein in the manufacture of a medicament for treating a CD3 related disease or condition in a subject, in the manufacture of a diagnostic reagent for diagnosing a CD3 related disease or condition.

The following examples are provided to better illustrate the claimed invention and are not to be interpreted as limiting the scope of the invention. All specific compositions, materials, and methods described below, in whole or in part, fall within the scope of the present invention. These specific compositions, materials, and methods are not intended to limit the invention, but merely to illustrate specific embodiments falling within the scope of the invention. One skilled in the art may develop equivalent compositions, materials, and methods without the exercise of inventive capacity and without departing from the scope of the invention. It will be understood that many variations can be made in the procedures herein described while still remaining within the bounds of the present invention. It is the intention of the inventors that such variations are included within the scope of the invention.

Example 1: Generation of Hybridoma Antibody 1.1 Animal Immunization

Recombinant extracellular domains (ECD) proteins of human CD3, including human CD3 epsilon (CD3epsilon) with His Tag (cat. No.: 10977-H08H; Sino Biological Inc. Beijing, China), human CD3 Gamma (CD3gamma) (cat. No.: ab140563; Abcam Shanghai China) and human CD3 delta (CD3delta) with His Tag (cat. No.: 10977-H08H; Sino Biological Inc. Beijing, China) were used as immunogens for animal immunization. Balb/c mice were purchased from Shanghai SLAC laboratory animal Co, Ltd. and were housed in an IACUC approved animal facility. Mice were immunized with the ECD protein mixture of CD3epsilon, CD3gamma and CD3delta or immunized with $7\times10^6$ freshly isolated human T-cells for each mouse, mixed with the Titermax adjuvant by subcutaneous and footpad injections every other week.

Blood were collected from mice before and after immunization and serum titers against target proteins were monitored by ELISA.

1.2 Hybridoma Generation

The mouse with the highest serum titer was chosen for cell fusion. The B cells from mouse spleen and lymphanodes were fused with SP2/0 myeloma cells by electro-fusion according to general electro-fusion procedures. After cell fusion, the cells were plated in 96-well plates with DMEM medium supplemented with 200/% FBS and 1% HAT selective reagents.

Antibodies presented in the supernatant of hybridoma medium were screened using CD3-expressing Jurkat cells by Flow cytometer assay (FACS), and counter-screened using CD3-negative MOLT-4 T cells by FACS. The hybridoma cells with binding activity to Jurkat cells, but not cross binding to MOLT-4 cells were collected as positive hybridoma cell lines, and then proceed to subcloning stage using semi-solid medium approach.

Single colonies were picked into 96-well plates with DMEM medium supplemented with 10% FBS for 2~3 days, and re-screened against target of CD3 using CD3-expressing Jurkat cells by Flow cytometer assay (FACS), and counter-screened using CD3-negative MOLT-4 T cells by FACS assay.

1.3 Hybridoma Sequencing

RNA was extracted from hybridoma cells and cDNA was amplified by using 5'-RACE kit, followed by PCR amplification using 3'-degenerated primers. PCR products were then cloned into pMD18-T vector, transformed, amplified and sequenced.

Eight mouse monoclonal antibodies were generated, CDR sequences of which are shown in Table 1 above.

Example 2: Generation of Humanized Antibody 2.1 IgG Conversion and Humanization

Generation of Chimeric Antibody from Marine-Derived mAbs:
WBP3311_2.166.48 and WBP3311_2.306.4 and WBP3312_3.179.16 VH and VL genes were re-amplified with cloning primers containing appropriate restriction sites and cloned into WuXi Biologics' proprietary expression vector to create corresponding clones of chimeric antibodies with constant region of human IgG1.

Humanization and Synthesis of Humanized V-Genes:

"Best Fit" approach was used to humanize WBP3311_2.166.48 and WBP3311_2.306.4 light and heavy chains. For light chains amino acid sequences of corresponding V-genes were blasted against in-house human germline V-gene database. The sequence of humanized VL-gene was derived by replacing human CDR sequences in the top hit with mouse CDR sequences using Kabat CDR definition. Frameworks were defined using extended CDR where Kabat CDR1 was extended by 5 amino acids at N-terminus. Multiple humanized sequences were created for each heavy chain and light chain by blasting mouse frameworks against human germline immunoglobulin database. Different FR combinations were created and analyzed for binding affinity, top three hits were used to derive sequences of humanized VH-genes. Humanized genes were back-translated, codon-optimized for mammalian expression, and synthesized by GeneArt Costum Gene Synthesis (Life Technologies). Synthetic genes were re-cloned into IgG expression vector, expressed and purified. FRs of the two humanized antibodies and their parental mouse antibodies were shown in Table 2 above.

Transient Expression and Purification of Chimeric and Humanized Antibodies:

The chimeric and humanized antibodies described above were constructed into WuXi Biologics' proprietary expression vector and expressed from 293F cells. The culture supernatant containing corresponding antibodies were harvested and purified using Protein A chromatography.

Example 3: In Vitro Characterization 3.1 Antibody Binding by ELISA and FACS

Antigens, antibodies and cells used in the ELISA and FACS described below are listed in table 3.

Binding of Antibodies to Protein by ELISA and $EC_{50}$:

Human CD3epsilon, CD3delta and CD3gamma proteins were pre-coated in 96-well plates, respectively. The binding affinity of eight mAbs at various concentrations to these three different CD3 protein extracellular domain was detected by corresponding HRP labeled $2^{nd}$ antibodies. The binding $EC_{50}$ (concentration of the test antibody when reaching half maximum binding) were analyzed by using GraphPad Prism software equation: Nonlinear regression (curve fit)—log (agonist) vs. response-Variable slope.

Specific Binding of Antibodies to Human CD3epsilon Protein by ELISA:

Eight mouse mAbs showed highly specific binding activity to human CD3epsilon without binding to CD3gamma and CD3delta and data were shown in Table 5.

TABLE 5

Specific binding against human CD3epsilon sub-unit protein

| | ELISA (A450) | | |
| --- | --- | --- | --- |
| mAbs | Human CD3epsilon (PC: 1.6; NC: 0.05) | Human CD3gamma (PC: 1.21; NC: 0.05) | Human CD3delta (PC: 1.9; NC: 0.05) |
| W3311-2.166.48 | 1.64 | 0.05 | 0.05 |
| W3311-2.306.4 | 1.46 | 0.06 | 0.05 |
| W3311-2.383.47 | 1.61 | 0.05 | 0.05 |
| W3311-2.400.5 | 1.57 | 0.05 | 0.05 |
| W3311-2.482.5 | 1.33 | 0.06 | 0.05 |
| W3311-2.488.33 | 1.70 | 0.06 | 0.05 |
| W3311-2.615.8 | 1.55 | 0.05 | 0.05 |
| W3311-2.844.8 | 1.54 | 0.07 | 0.06 |

Cellular Binding of Antibodies by FACS and $EC_{50}$:

Various concentrations of testing mAbs were added to Jurkat cells, and then the binding activity of mAbs onto the surface of cells was detected by 2nd antibody-FITC. OKT3 was used as the positive control. The stained cells were analyzed by using a BD Biosciences FACSCanto II instrument and Flow Jo Version software. The binding $EC_{50}$ were

TABLE 3

Antigens, antibodies and cells used in ELISA and FACS

| Material | Company | Cat. log No. |
| --- | --- | --- |
| Human CD3 epsilon (CD3epsilon) protein His Tag) | Sino Biological Inc. | 10977-H08H |
| Human CD3 delta (CD3 delta) protein (His Tag) | Sino Biological Inc. | 10981-H08H |
| Human CD3 Garmma (CD3gamma) protein | Abcam | ab140563 |
| Cynomolgus Monkey CD3 epsilon protein | ACRO | CDE-C5226 |
| Cyno PBMCs | PharmaLegacy Laboratories (Shanghai) Co. | |
| Mouse anti human CD3 epsilon monoclonal antibody | Sino Biological Inc. | 10977-MM03 (Clone NO.: 1A7E5G5) |
| Mouse anti-human CD3 delta monoclonal Antibody | Sino Biological Inc. | 10981-MM08 |
| Mouse anti-human CD3gamma monoclonal Antibody | SANTA CRUZ BIOTECHNOLOGY, INC | sc-55563 |
| Benchmark antibody OKT3 | Abcam | ab86883 |
| Jurkat cells | ATCC | TIB-152 |
| HUT78 cells | ATCC | ECACC-880401901 |
| MOLT-4 cells | ATCC | CRL-1582 |
| Semi-solid medium | Stemcells | 03814 | calculated by using GraphPad Prism software equation: Nonlinear regression (curve fit)—log (agonist) vs. response-Variable slope.

Specific Binding to Human CD3 Receptor on T Cell Surface:

Eight mAbs showed highly specific binding activity to human CD3 expressing cells (Jurkat cells), without binding to CD3-negative cells (MOTL-4 cells and 293F cells) in Table 6.

TABLE 6

Specific binding to human CD3 receptor cross multiple cell lines by FACS

| mAbs | MFI (FACS) (JurkatB10: 3145~4045) | MFI (FACS) (MOLT-4: 22.7~27.3) | MFI (FACS) (293F: 22.6~24.6) |
|---|---|---|---|
| W3311-2.166.48 | 2139 | 42.5 | 24.9 |
| W3311-2.306.4 | 3365 | 53.5 | 29.1 |
| W3311-2.383.47 | 2132 | 44.5 | 29.8 |
| W3311-2.400.5 | 2741 | 54.5 | 25.1 |
| W3311-2.482.5 | 2390 | 54.8 | 25.0 |
| W3311-2.488.33 | 2266 | 58.4 | 30.2 |
| W3311-2.615.8 | 2215 | 57.2 | 25.7 |
| W3311-2.844.8 | 984 | 42.5 | 22.7 |

3.2 Cross Species Target Protein Binding of Antibodies by ELISA and FACS

Binding affinities of the test antibodies to CD3 from different species were analyzed. Homology of the human, monkey, rat and mouse CD3 reference sequences are shown below.

TABLE 4

Human, monkey, rat and mouse CD3 domain sequences homology

| Species | CD3epsilon (%) | CD3delta (%) | CD3gamma (%) |
|---|---|---|---|
| Human | 100 (NP_000724) | 100 (NP_000723) | 100 (NP_000064) |
| Macaca fascicularis (monkey) | 83 (NP_001270544) | 94 (NP_001274617) | 81 (NP_001270839) |
| Macaca mulatta (monkey) | 84 (XP_001097204) | 94 (NP_001097302) | 82 (NP_001253854) |
| Mouse | 59 (NP_031674) | 64 (NP_038515) | 70 (AAA37400) |
| Rattus norvegicus (Rat) | 57 (NP_001101610) | 69 (NP_037301) | 71 (NP_001071114) |

Cross-Binding of Antibodies to Cynomolgus Monkey CD3epsilon and Mouse CD3 Epsilon by ELISA:

Various concentrations of testing antibodies, positive and negative controls were added to the 96-well plates that were pre-coated with Cynomolgus Monkey CD3epsilon protein and mouse CD3epsilon. The binding of the antibodies to the Cynomolgus Monkey CD3epsilon protein and mouse CD3epsilon protein was detected by corresponding HRP labeled $2^{nd}$ antibodies (BETHYL, A90-231P). The $EC_{50}$ were calculated by using GraphPad Prism software.

Data showed that all eight mAbs showed potent cross-binding activity to Cynomolgus Monkey CD3epsilon, but no binding to mouse CD3epsilon. The positive control OKT3 showed neither cross-binding activity to Cynomolgus Monkey CD3epsilon or mouse CD3epsilon Table 7.

TABLE 7

Cross-binding against Cynomolgus Monkey CD3epsilon and mouse CD3epsilon

| | ELISA A450 | | |
|---|---|---|---|
| mAbs | Human CD3epsilon | Cyno-Monkey CD3epsilon | Mouse CD3 epsilon |
| Negative Control | 0.046 | 0.046 | 0.179 |
| OKT3 | 0.048 | 0.052 | 0.24 |
| W3311-2.166.48 | 2.761 | 2.808 | 0.446 |
| W3311-2.306.4 | 2.909 | 2.822 | 0.711 |
| W3311-2.383.47 | 2.786 | 2.756 | 0.666 |
| W3311-2.400.5 | 2.828 | 2.794 | 0.709 |
| W3311-2.482.5 | 2.953 | 2.874 | 0.61 |
| W3311-2.488.33 | 2.914 | 2.831 | 0.607 |
| W3311-2.615.8 | 2.824 | 2.713 | 0.471 |
| W3311-2.844.8 | 2.923 | 2.75 | 0.6 |

Cross-Binding of Antibodies to Cynomolgus Monkey CD3epsilon by FACS:

Cyno PBMCs were isolated from healthy Cyno whole blood by using Ficoll-Paque PLUS gradient centrifugation and 100 g centrifugation steps to remove thrombocytes. PBMC were cultured in complete RPMI-1640 medium until ready to use. Various concentrations of test antibodies were added to Cyno PBMCs, and then the binding activity of the antibodies onto the surface of the cells were detected by $2^{nd}$ antibody-FITC (Jackson, 115-095-008). The stained cells were analyzed by using a BD Biosciences FACSCanto II and FlowJo Version software. The binding $EC_{50}$ were calculated by using GraphPad Prism software equation: Nonlinear regression (curve fit).

Epitope Binning of Antibodies by FACS:

Various concentrations of test antibodies were mixed with certain amount of biotinylated antibody of W3311-2.383.47, respectively. The mixture was then added to CD3-expressing cells in 96-well plates and incubated at 4° C. for 1 hour. The binding of the target antibody onto the cells expressing CD3 was detected using PE-conjugated anti-biotin Ab. Samples were tested by flow cytometry and data were analyzed by FlowJo.

Binding Against Human CD3epsilon and Cynomolgus Monkey CD3epsilon Protein and $EC_{50}$ Calculation by ELISA:

Eight mAbs showed strong binding activity to human CD3epsilon and cross binding to Cynomolgus Monkey CD3epsilon protein and showed comparable $EC_{50}$ in low nM range between human CD3epsilon and Cynomolgus Monkey CD3epsilon in Table 8.

TABLE 8

Eight mAbs $EC_{50}$ for human CD3epsilon and Cynotnolgus Monkey CD3epsilon

| mAbs | Human CD3epsilon $EC_{50}$ (nM) | Cynomolgus Monkey CD3epsilon $EC_{50}$ (nM) |
|---|---|---|
| W3311-2.166.48 | 0.049 | 0.033 |
| W3311-2.306.4 | 0.012 | 0.011 |
| W3311-2.383.47 | 0.074 | 0.028 |
| W3311-2.400.5 | 0.053 | 0.024 |
| W3311-2.482.5 | 0.069 | 0.028 |
| W3311-2.488.33 | 0.026 | 0.019 |

TABLE 8-continued

Eight mAbs EC$_{50}$ for human CD3epsilon and Cynotnolgus Monkey CD3epsilon

| mAbs | Human CD3epsilon EC$_{50}$ (nM) | Cynomolgus Monkey CD3epsilon EC$_{50}$ (nM) |
|---|---|---|
| W3311-2.615.8 | 0.033 | 0.025 |
| W3311-2.844.8 | 0.011 | 0.009 |
| WBP331-BMK1 (UCHT1) | 0.186 | NA |
| Isotype control | NA | NA |

4.3 Detection of Cross-Species Binding of Humanized Antibodies

Cynomolgus Monkey CD3epsilon Protein Binding and EC$_{50}$ Value of Two Humanized mAbs:

All data indicated both humanized mAbs retained their high binding activity to Cynomolgus Monkey CD3epsilon protein (see FIG. 1) with EC$_{50}$ value of 0.043 nM for both humanized antibodies in Table 9.

TABLE 9

Two humanized mAbs EC$_{50}$ for Cynomolgus Monkey CD3epsilon

| mAbs | EC$_{50}$ (nM) |
|---|---|
| W3311-2.166.48-z1-uIgG1K | 0.043 |
| W3311-2.306.4-z1-uIgG1K | 0.043 |
| W3311-2.166.48 | 0.125 |
| Isotype control | N/A |

Affinity of Antibodies by FACS:

$5 \times 10^4$ Jurkat cells/well were seeded in 96-well plates, followed by the addition of purified testing lead antibodies at various concentrations as the 1st antibody for 1 hour at 4° C. The 2$^{nd}$ antibody of Goat Anti-Mouse IgG Fc-FITC was added for 30 min at 4° C., and then stained cells by FITC were detected by FACS. K$_D$ value was calculated according to the method described above.

Figure 2:
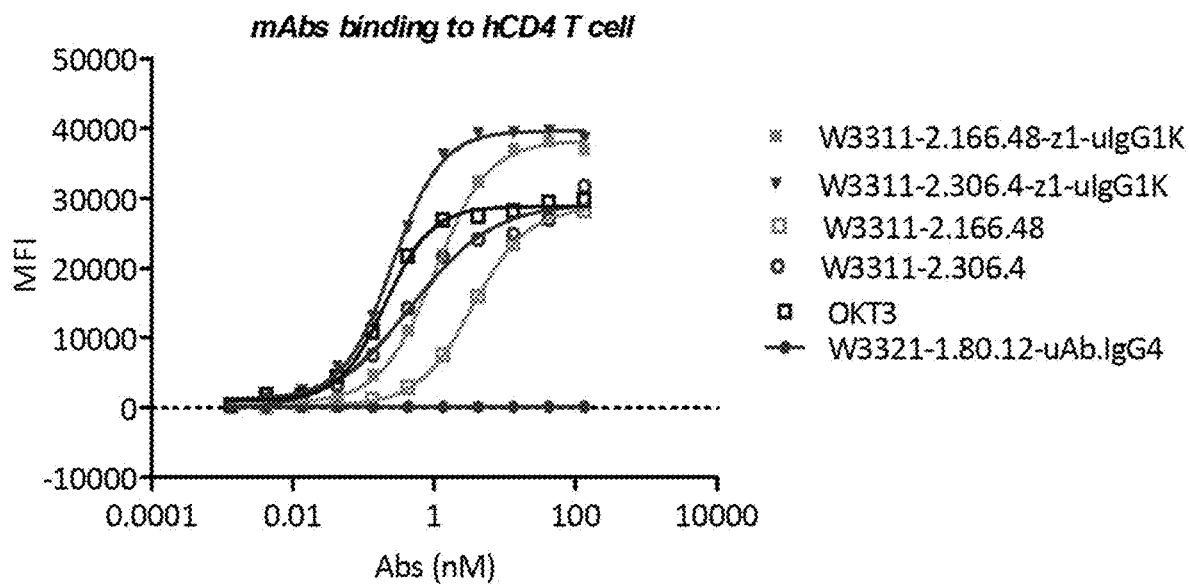
FIG. 2 shows binding of the monoclonal antibodies, WBP3311_2.166.48-uIgG1K, WBP3311_2.306.4-uIgG1K, WBP3311_2.166.48, and WBP3311_2.306.4, to human CD4 T cells as measured by flow cytometry assay.
Figure 3:
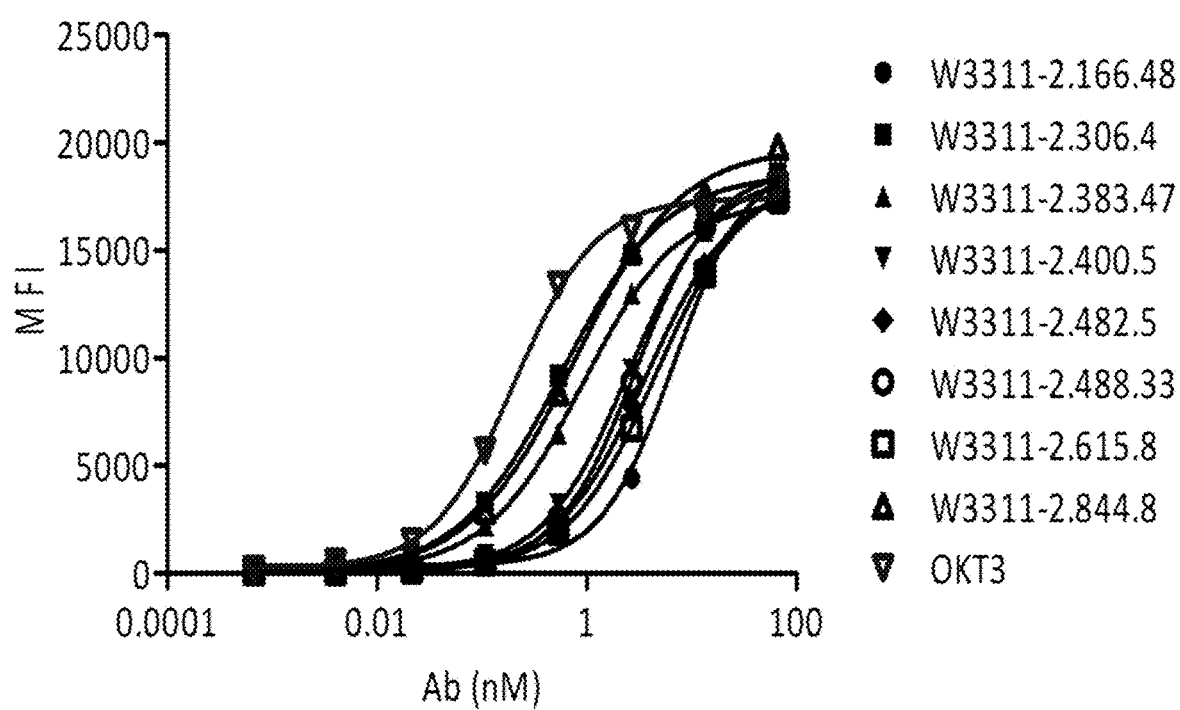
FIG. 3 shows binding affinity of eight mouse antibodies (W3311-2.166.48, W3311-2.306.4, W3311-2.383.47, W3311-2.400.5, W3311-2.482.5, W3311-2.488.33, W3311-2.615.8, and W3311-2.844.8) to human CD3 expressing cells (Jurkat cells) as measured by flow cytometry assay.

Two Humanized mAbs were Tested the Binding Activity on Human CD4 T Cells:

Data indicated that both humanized antibodies retained high binding activity to CD4 T cells (see FIG. 2) with low EC$_{50}$ values of 1.01 and 0.46 nM for WBP3311-2.166.48-z1-uIgG1k and WBP3311-2.306.4-z1-uIgG1k, respectively, which were 0.5-1 fold lower than that of respective parental antibodies in Table 10.

TABLE 10 hCD4 T cell binding of two humanized mAbs by FACS and EC$_{50}$

| mAbs | EC$_{50}$ (nM) |
|---|---|
| W3311-2.166.48-z1-uIgG1K | 1.01 |
| W3311-2.166.48-mIgG2aK | 3.514 |
| W3311-2.306.4-z1-uIgG1K | 0.253 |
| W3311-2.306.4-mIgG2bK | 0.461 |
| OKT3 | 0.202 |
| Isotype control | N/A |

4.5 Affinity and EC$_{50}$ of Antibodies by FACGS

Eight mAbs were tested for their EC$_{50}$ by FACS and were tested affinity to human CD3 expressing cells (Jurkat cells). The EC$_{50}$ of the 8 mAbs ranged from 0.57 nM to 6.91 nM (see Table 11), and the affinity ranged from $1.3 \times 10^{-9}$ to $9.3 \times 10^{-10}$ M in Table 12.

TABLE 11

EC$_{50}$ measurement on Jurkat cells by FACS

| mAbs | EC$_{50}$ (nM) |
|---|---|
| W3311-2.166.48 | 6.91 |
| W3311-2.306.4 | 0.57 |
| W3311-2.383.47 | 0.91 |
| W3311-2.400.5 | 2.5 |
| W3311-2.482.5 | 3.71 |
| W3311-2.488.33 | 2.97 |
| W3311-2.615.8 | 4.65 |
| W3311-2.844.8 | 0.77 |
| OKT3 | 0.2 |

TABLE 12

Eight mAbs K$_D$ value on Jurkat cells by FACS

| | Sample | | | | | | | | |
|---|---|---|---|---|---|---|---|---|---|
| | W3311-2.166.48 | W3311-2.306.4 | W3311-2.383.47 | W3311-2.400.5 | W3311-2.482.5 | W3311-2.488.33 | W3311-2.615.8 | W3311-2.844.8 | WBP3311. OKT3- Average |
| Best fit-Bmax | 1.26E-10 | 1.17E-10 | 1.12E-10 | 1.13E-10 | 1.30E-10 | 1.30E-10 | 1.20E-10 | 1.19E-10 | 9.41E-11 |
| Best fit-K$_D$ | 1.67E-09 | 1.91E-10 | 4.03E-10 | 9.34E-10 | 2.29E-09 | 1.32E-09 | 2.23E-09 | 2.52E-10 | 1.29E-10 |
| Std. Error-Bmax | 1.66E-12 | 1.19E-12 | 1.62E-12 | 1.76E-12 | 2.35E-12 | 2.51E-12 | 2.18E-12 | 1.00E-12 | 1.95E-12 |
| Std. Error-K$_D$ | 5.62E-11 | 8.32E-12 | 2.15E-11 | 4.38E-11 | 9.63E-11 | 6.98E-11 | 9.47E-11 | 8.64E-12 | 1.27E-11 |

4.6 Affinity and Kinetic K$_D$ Measurement of Two Humanized mAb by FACS

Figure 4A:
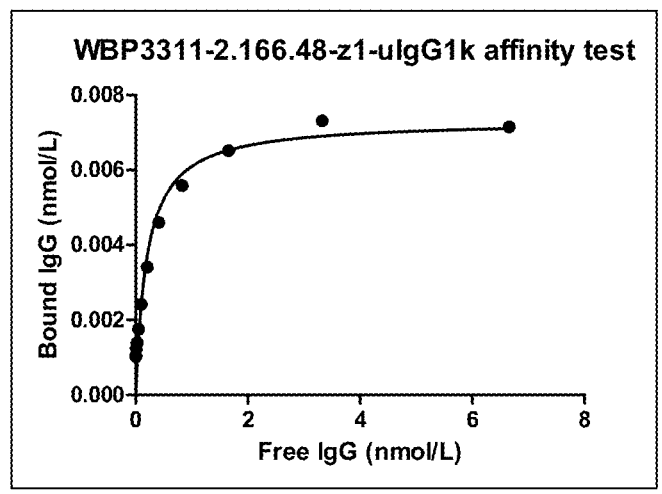
FIG. 4A shows binding affinity of humanized antibody, WBP3311_2.166.48-z1-uIgG1K to human CD3 expressing cells (Jurkat cells) as measured by flowcytometry assay.
Figure 4B:
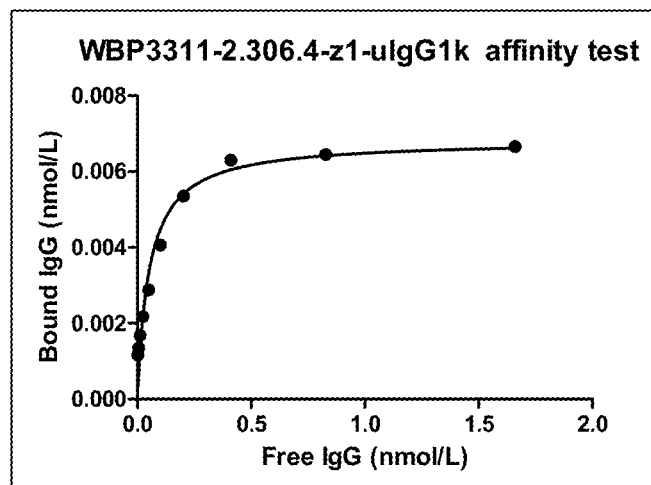
FIG. 4B shows the result of binding affinity of humanized antibody, WBP3311_2.306.4-z1-uIgG1K to human CD3 expressing cells (Jurkat cells) as measured by flow cytometry assay.
Figure 4C:
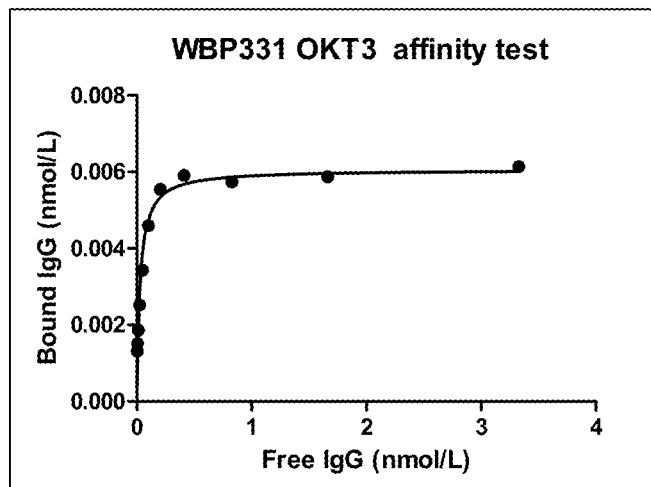
FIG. 4C shows the result of binding affinity of the positive control, OKT3 to human CD3 expressing cells (Jurkat cells) as measured by flow cytometry assay.

Two humanized mAbs were tested for Affinity measurement on Jurkat cells by FACS. The data indicated that both humanized mAbs retained their high affinity activity on Jurkat cells with the K$_D$ values similar to their respective parental mAbs in FIG. 4 and Table 13.

TABLE 13

Kinetic $K_D$ measurement of two humanized mAbs on Jurkat cells by FACS

| Sample | WBP3311-2.166.48-z1-uIgG1k | WBP3311-2.306.4-z1-uIgG1k | OKT3 |
| --- | --- | --- | --- |
| Best fit-Bmax | 7.32E−12 | 6.83E−12 | 6.06E−12 |
| Best fit-KD | 2.01E−10 | 5.30E−11 | 2.77E−11 |
| Std. Error-Bmax | 3.82E−13 | 3.49E−13 | 2.19E−13 |
| Std. Error-KD | 4.38E−11 | 1.14E−11 | 5.13E−12 |

3.3 Cell Based Functional Assays

Cell Internalization of Antibodies by FACS:

Jurkat cells were seeded at 1×10⁵/well in 96-well plates. Testing antibodies (1 μg/mL) were added to the cells, and incubated for 1 hour at 4° C. After incubation, unbound antibodies were washed away, and the cells were then incubated for 3 hours at 4° C. or 37° C. with 5% $CO_2$. After incubation, the presence of antibodies on the cell surface was detected by 2nd antibody (Abcam, ab98742). The stained cells were analyzed by using a BD Biosciences FACSCanto II and FlowJo Version software. The internalization rate was calculated as below: [($MFI_{0\ hour}$−$MFI_{3\ hours}$)/$MFI_{0\ hour}$]*100%.

4.7 Cell Internalization Rate Measurement

Figure 5:
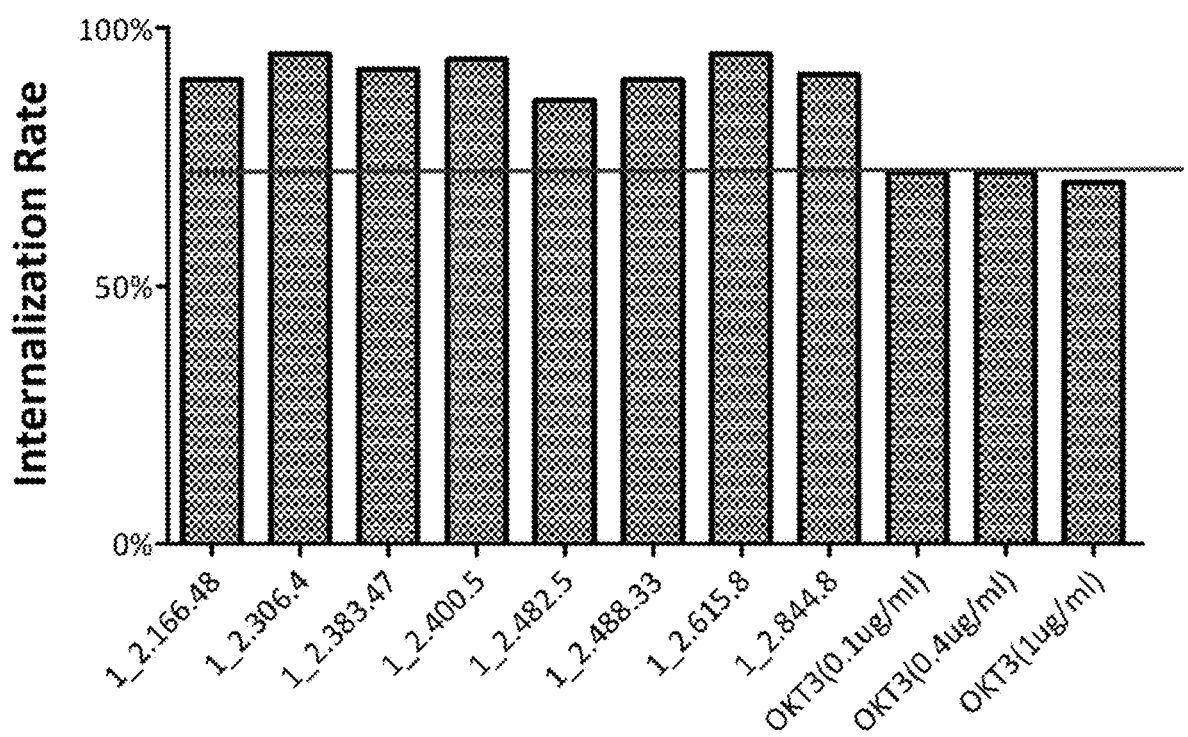
FIG. 5 shows cell internalization rate of eight mouse antibodies (W3311-2.166.48, W3311-2.306.4, W3311-2.383.47, W3311-2.400.5, W3311-2.482.5, W3311-2.488.33, W3311-2.615.8, and W3311-2.844.8) to human CD3 expressing cells (Jurkat cells) as measured by flow cytometry assay.

Internalization rate was tested using Jurkat cells by FACS. The data indicated all 8 mAbs showed high internalization rate ranging from 86-94% antibody internalized after 3 hours study period, whereas the OKT3 showed about 72% internalization rate in FIG. 5.

T Cell Activation of Antibodies with Intracellular Cytokine Staining Assay:

Intracellular cytokine staining is a flow cytometry-based assay that can detect cytokine production by immune cells in combination with cell surface markers. Human PBMCs were isolated from healthy donor. Briefly, Ficoll-Paque PLUS gradient centrifugation was used with subsequent 100 g centrifugation steps to remove thrombocytes. PBMC were cultured in complete RPMI-1640 medium. PBMC were resuspended in cell culture medium supplemented with Golgi Stop and dispended at 2×10⁵/well in 96-well plates. Various concentrations of test antibodies, positive and negative controls were added and then incubated with the cells for 4.5 hours at 37° C. After incubation, the cells were washed two times with 1% BSA, and then stained for their surface makers by using anti-human CD4-FITC antibody (BD, 550628), and anti-human CD8-PE antibody (BD, 560959), followed by fixation and permeabilization using the Human Regulatory T Cell Staining Kit (eBioscience, 88-8999). Post fixation/permeabilization, the cells were detected for cytokine production by using anti-human TNF-APC antibody (BD, 554514) and anti-human IFN-PerCP-Cy5.5 antibody (eBioscience, 45-7319-42). The stained cells were analyzed by using BD Biosciences FACSCanto II and FlowJo Version software.

Figure 6:
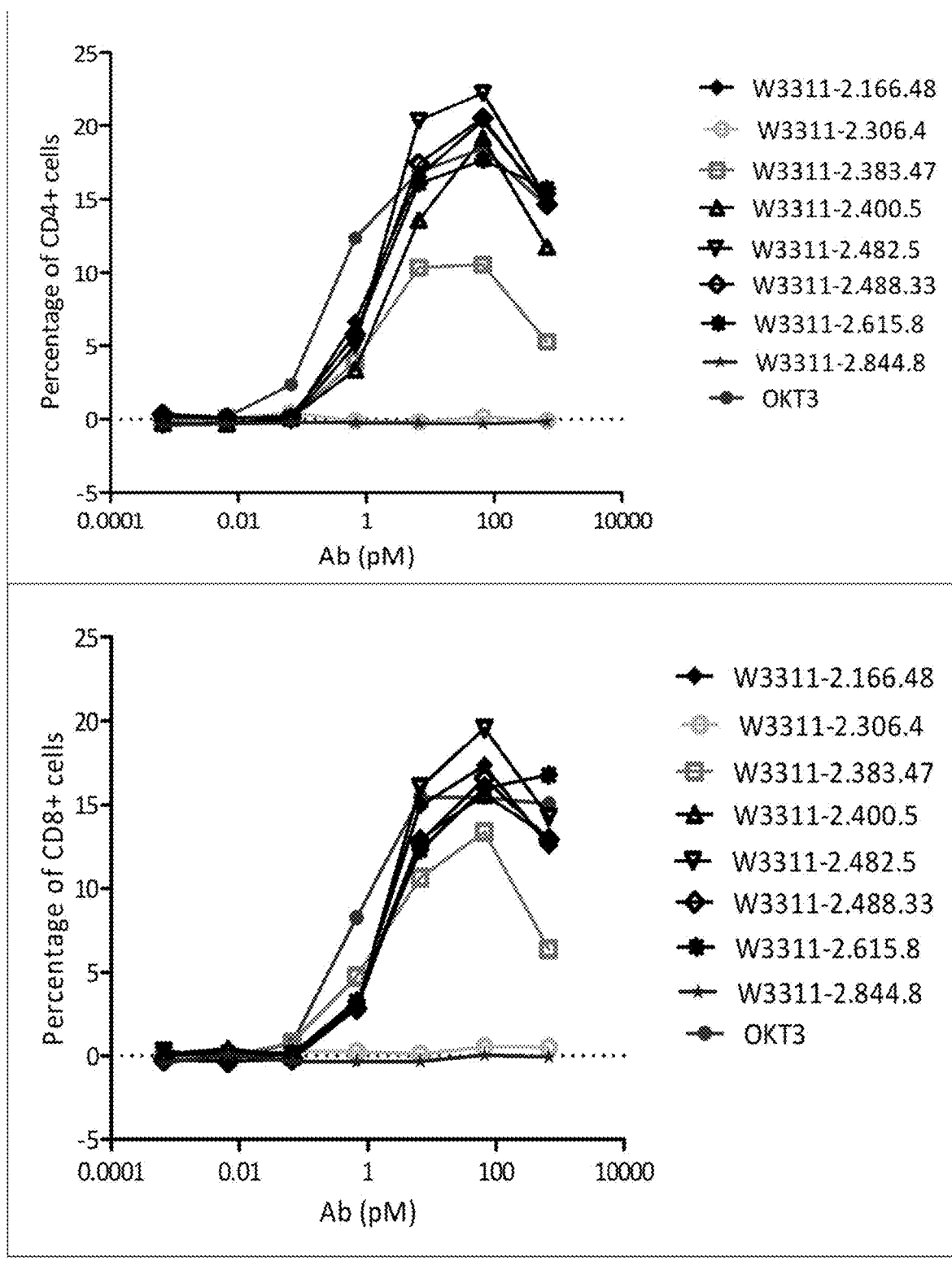
FIG. 6 shows the result of human T cell activation by eight mouse antibodies (W3311-2.166.48, W3311-2.306.4, W3311-2.383.47, W3311-2.400.5, W3311-2.482.5, W3311-2.488.33, W3311-2.615.8, and W3311-2.844.8) as measured by intracellular cytokine TNFalpha and IFNgamma staining.

T Cell Activation:

T cell activation was evaluated using Human PBMCs by Intracellular cytokine staining method and the cytokines of TNFalpha and INFgamma were monitored. The data indicated that among 8 testing mAbs 2.306.4 and 2.844.8 did not show significant T cell activation event as no significant cytokines of TNFalpha and INFgamma release was monitored, whereas all other 6 test mAbs showed T cell activation to the extent similar to that of OKT3, except for clone 2.383.47 which showed a weaker T cell activation as compared to OKT3, data shown in FIG. 6.

Figure 7:
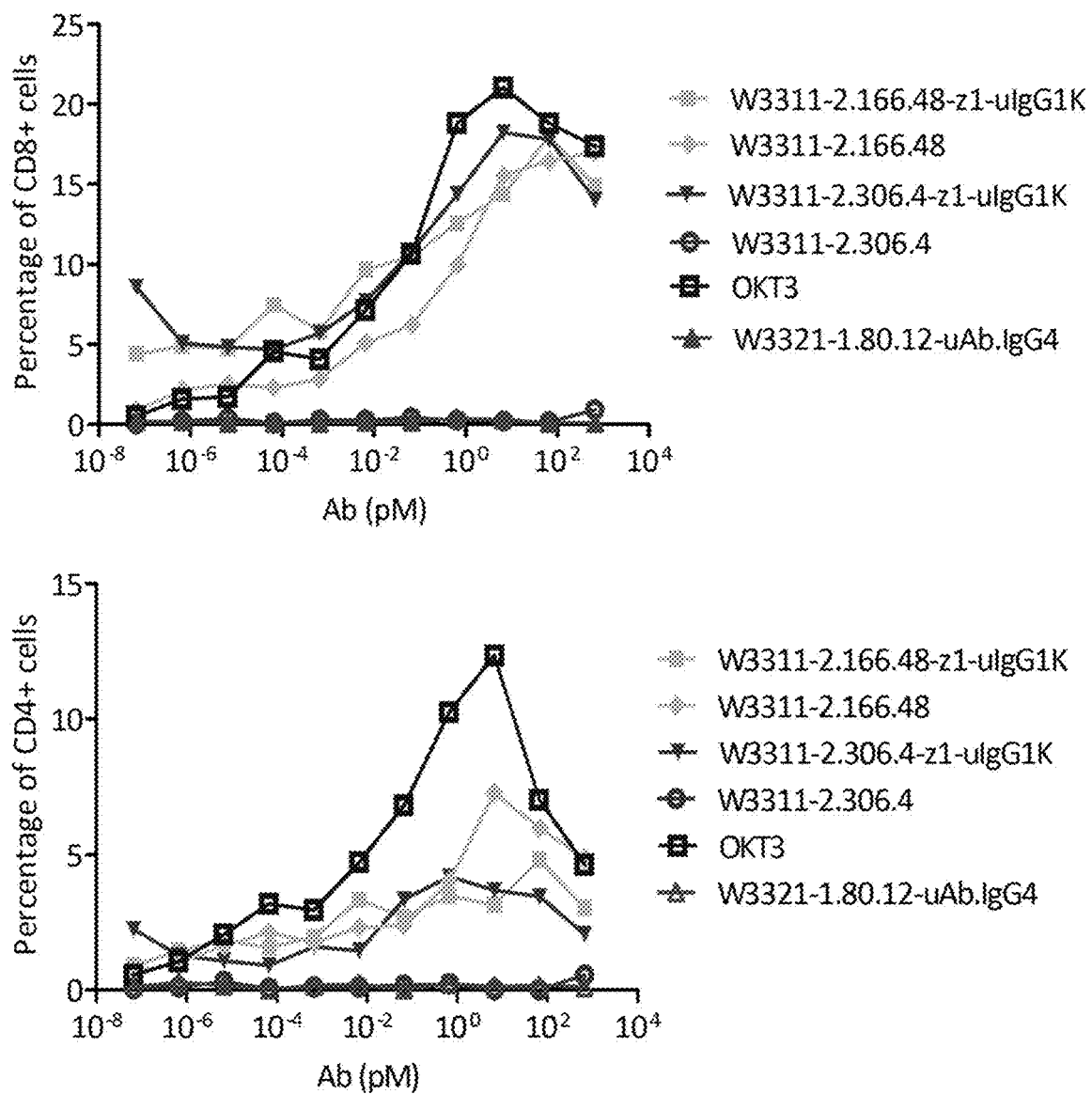
FIG. 7 shows the result of human T cell activation by two humanized antibodies (WBP3311_2.166.48-z1-uIgG1K and WBP3311_2.306.4-z1-uIgG1K) as measured by intracellular cytokine TNFalpha and IFNgamma staining.

Human T Cell Activation of Two Humanized mAbs:

Two humanized mAbs were tested the T cell activation activity on Human PBMCs by Intracellular cytokine staining method and the cytokines of TNFalpha and IFNgamma were monitored. The data indicated that both humanized antibodies showed similar extent T cell activation to OKT3 positive control on CD8+ T cells, whereas both humanized mAbs showed lower extent activation on CD4+ T cells compared to OKT3. It is also noticed that the parental mouse antibody of clone 2.306.4 repeatedly displayed no T cells activation. Data were shown in FIG. 7.

3.4 Epitope Binning of Antibodies by FACS

Figure 8:
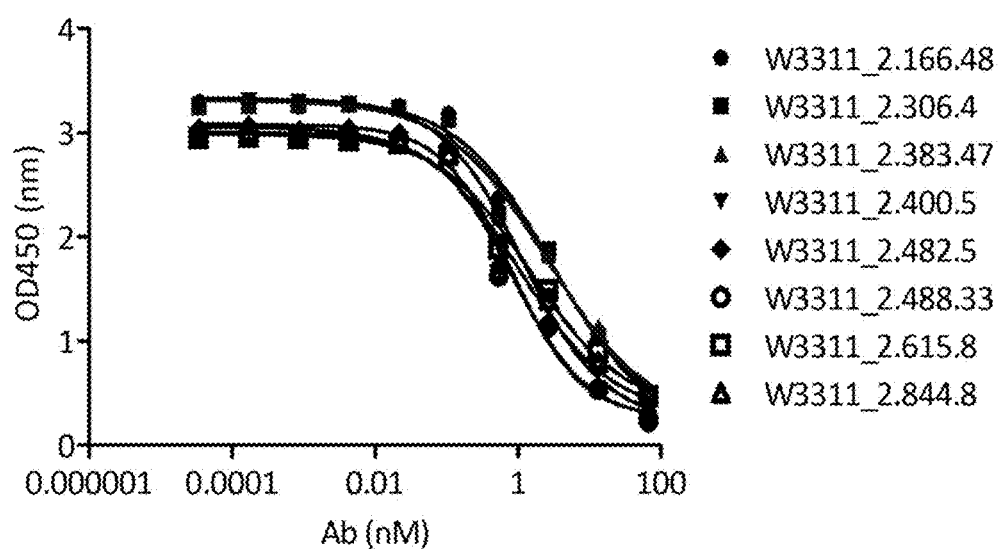
FIG. 8 shows the result of epitope binning of seven mouse antibodies (W3311-2.166.48, W3311-2.306.4, W3311-2.400.5, W3311-2.482.5, W3311-2.488.33, W3311-2.615.8, and W3311-2.844.8) against the clone WBP3311_2.383.47.

Epitope Binning:

Seven of 8 mAbs are binned against clone 2.383.47 and the result showed that all 8 mAbs sharing the same epitope bin in FIG. 8.

What is claimed is:

1. An isolated antibody or an antigen-binding fragment thereof, comprising:

a) heavy chain CDR sequences comprising SEQ ID NO: 7, SEQ ID NO: 9, and SEQ ID NO: 11; and kappa light chain CDR sequences comprising SEQ ID NO: 8, SEQ ID NO: 10, and SEQ ID NO: 12;

b) heavy chain CDR sequences comprising SEQ ID NO: 1, SEQ ID NO: 3, and SEQ ID NO: 5; and kappa light chain CDR sequences comprising SEQ ID NO: 2, SEQ ID NO: 4, and SEQ ID NO: 6;

c) heavy chain, CDR sequences comprising SEQ ID NO: 13, SEQ ID NO: 15, and SEQ ID NO: 17; and kappa light chain CDR sequences comprising SEQ ID NO: 14, SEQ ID NO: 16, and SEQ ID NO: 18;

d) heavy chain CDR sequences comprising SEQ ID NO: 19, SEQ ID NO: 21, and SEQ ID NO: 23; and kappa light chain CDR sequences comprising SEQ ID NO: 20, SEQ ID NO: 22, and SEQ ID NO: 24;

e) heavy chain CDR sequences comprising SEQ ID NO: 25, SEQ ID NO: 27, and SEQ ID NO: 29; and kappa light chain CDR sequences comprising SEQ ID NO: 26, SEQ ID NO: 28, and SEQ ID NO: 30;

f) heavy chain CDR sequences comprising SEQ ID NO: 31, SEQ ID NO: 33, and SEQ ID NO: 35; and kappa light chain CDR sequences comprising SEQ ID NO: 32, SEQ ID NO: 34, and SEQ ID NO: 36;

g) heavy chain CDR sequences comprising SEQ ID NO: 37, SEQ ID NO: 39, and SEQ ID NO: 41; and kappa light chain CDR sequences comprising SEQ ID NO: 38, SEQ ID NO: 40, and SEQ ID NO: 42; or h) heavy chain CDR sequences comprising SEQ ID NO: 43, SEQ ID NO: 45, and SEQ ID NO: 47; and kappa light chain CDR sequences comprising SEQ ID NO: 44, SEQ ID NO: 46, and SEQ ID NO: 48.

2. The antibody or an antigen-binding fragment thereof of claim 1, comprising:

a) a heavy chain variable region comprising SEQ ID NO: 117 and a kappa light chain variable region comprising SEQ ID NO: 119;

b) a heavy chain variable region comprising SEQ ID NO: 81 and a kappa light chain variable region comprising SEQ ID NO: 83;

c) a heavy chain variable region comprising SEQ ID NO: 85 and a kappa light chain variable region comprising SEQ ID NO: 87;

d) a heavy chain variable region comprising SEQ ID NO: 89 and a kappa light chain variable region comprising SEQ ID NO: 91;

e) a heavy chain variable region comprising SEQ ID NO: 93 and a kappa light chain variable region comprising SEQ ID NO: 95;

f) a heavy chain variable region comprising SEQ ID NO: 97 and a kappa light chain variable region comprising SEQ ID NO: 99;

g) a heavy chain variable region comprising SEQ ID NO: 101 and a kappa light chain variable region comprising SEQ ID NO: 103;

h) a heavy chain variable region comprising SEQ ID NO: 105 and a kappa light chain variable region comprising SEQ ID NO: 107;

i) a heavy chain variable region comprising SEQ ID NO: 109 and a kappa light chain variable region comprising SEQ ID NO: 111; or j) a heavy chain variable region comprising SEQ ID NO: 113 and a kappa light chain variable region comprising SEQ ID NO: 115.

3. The antibody or antigen-binding fragment thereof of claim 1, further comprising an immunoglobulin constant region, optionally a constant region of IgG, optionally a constant region of human IgG1.

4. The antibody or an antigen-binding fragment thereof of claim 1, which is a humanized antibody.

5. The antibody or antigen-binding fragment thereof of claim 1, which is a camelized single domain antibody, a diabody, a scFv, an scFv dimer, a BsFv, a dsFv, a (dsFv)2, a dsFv-dsFv', an Fv fragment, a Fab, a Fab', a F(ab')2, a bispecific antibody, a ds diabody, a nanobody, a domain antibody, or a bivalent domain antibody.

6. The antibody or an antigen-binding fragment thereof of claim 5, wherein the antibody or an antigen-binding fragment thereof is bispecific and has a first specificity for CD3epsilon, and a second specificity.

7. The antibody or an antigen-binding fragment thereof of claim 6, wherein the second specificity is for a second antigen different from CD3epsilon wherein presence of the second antigen in proximity to a CD3epsilon-expressing T cells is desirable for the second antigen to be recognized by immune system.

8. The antibody or antigen-binding fragment thereof claim 1 linked to one or more conjugates, wherein the conjugate comprises a chemotherapeutic agent, a toxin, a radioactive isotope, a lanthanide, a luminescent label, a fluorescent label, or an enzyme-substrate label.

9. The antibody or an antigen-binding fragment thereof of claim 1, capable of specifically binding to CD3epsilon, and optionally wherein the CD3epsilon are derived from mouse, rat, monkey or human, and optionally wherein the CD3epsilon is a recombinant CD3epsilon or a CD3epsilon expressed on a cell surface.

10. A pharmaceutical composition comprising the antibody or antigen-binding fragment thereof of claim 1, and a pharmaceutically acceptable carrier.

11. An isolated polynucleotide encoding the antibody or an antigen-binding fragment thereof of claim 1.

12. A vector comprising the isolated polynucleotide of claim 11.

13. A host cell comprising the vector of claim 12.

14. A method of expressing the antibody or antigen-binding fragment thereof of claim 1, comprising culturing a host cell comprising a vector comprising an isolated polynucleotide encoding the antibody or antigen-binding fragment thereof of claim 1 under the condition at which the vector is expressed.

15. A method of treating a CD3 related disease or condition, comprising administering to the subject a therapeutically effective amount of the antibody or antigen-binding fragment thereof of claim 1.

16. The method of claim 15, wherein the antibody or antigen-binding fragment thereof is bispecific and the disease or condition is cancer.

17. A method of activating CD3epsilon-expressing T cells in vivo or in vitro, comprising contacting the CD3epsilon-expressing T cells with the antibody or antigen-binding fragment thereof of claim 1.

18. A method of promoting in vivo or in vitro processing of a second antigen by CD3epsilon —expressing T cell, comprising contacting the CD3epsilon-expressing T cells with the bispecific antibody or antigen-binding fragment thereof of claim 6, wherein the bispecific antibody or antigen-binding fragment is capable of specifically binding to both the CD3epsilon-expressing T cells and a second antigen thereby bringing both in close proximity.

19. A kit comprising the antibody or antigen-binding fragment thereof of claim 1, useful in detecting CD3epsilon, optionally recombinant CD3epsilon, CD3epsilon expressed on cell surface, or CD3epsilon-expressing cells, or useful in diagnosing a CD3 related disease or condition in a subject.

* * * * *

SEQUENCE LISTING

<160> NUMBER OF SEQ ID NOS: 120

<210> SEQ ID NO 1
<211> LENGTH: 10
<212> TYPE: PRT
<213> ORGANISM: Mus musculus

<400> SEQUENCE: 1

Gly Tyr Ser Phe Thr Thr Tyr Tyr Ile His
1               5                   10

<210> SEQ ID NO 2
<211> LENGTH: 17
<212> TYPE: PRT
<213> ORGANISM: Mus musculus

<400> SEQUENCE: 2

Lys Ser Ser Gln Ser Leu Leu Asn Ser Arg Thr Arg Lys Asn Tyr Leu
1               5                   10                  15

Ala

<210> SEQ ID NO 3
<211> LENGTH: 17
<212> TYPE: PRT
<213> ORGANISM: Mus musculus

<400> SEQUENCE: 3

Trp Ile Phe Pro Gly Asn Asp Asn Ile Lys Tyr Ser Glu Lys Phe Lys
1               5                   10                  15

Gly

<210> SEQ ID NO 4
<211> LENGTH: 7
<212> TYPE: PRT
<213> ORGANISM: Mus musculus

<400> SEQUENCE: 4

Trp Ala Ser Thr Arg Lys Ser
1               5

<210> SEQ ID NO 5
<211> LENGTH: 10
<212> TYPE: PRT
<213> ORGANISM: Mus musculus

<400> SEQUENCE: 5

Asp Ser Val Ser Ile Tyr Tyr Phe Asp Tyr
1               5                   10

<210> SEQ ID NO 6
<211> LENGTH: 8
<212> TYPE: PRT
<213> ORGANISM: Mus musculus

<400> SEQUENCE: 6

Thr Gln Ser Phe Ile Leu Arg Thr
1               5

<210> SEQ ID NO 7
<211> LENGTH: 10
<212> TYPE: PRT
<213> ORGANISM: Mus musculus

<400> SEQUENCE: 7

Gly Phe Ala Phe Thr Asp Tyr Tyr Ile His
1               5                   10

<210> SEQ ID NO 8
<211> LENGTH: 17
<212> TYPE: PRT
<213> ORGANISM: Mus musculus

<400> SEQUENCE: 8

Lys Ser Ser Gln Ser Leu Leu Asn Ser Arg Thr Arg Lys Asn Tyr Leu
1               5                   10                  15

Ala

<210> SEQ ID NO 9
<211> LENGTH: 17
<212> TYPE: PRT
<213> ORGANISM: Mus musculus

```
<400> SEQUENCE: 9

Trp Ile Ser Pro Gly Asn Val Asn Thr Lys Tyr Asn Glu Asn Phe Lys
1               5                   10                  15

Gly

<210> SEQ ID NO 10
<211> LENGTH: 7
<212> TYPE: PRT
<213> ORGANISM: Mus musculus

<400> SEQUENCE: 10

Trp Ala Ser Thr Arg Gln Ser
1               5

<210> SEQ ID NO 11
<211> LENGTH: 10
<212> TYPE: PRT
<213> ORGANISM: Mus musculus

<400> SEQUENCE: 11

Asp Gly Tyr Ser Leu Tyr Tyr Phe Asp Tyr
1               5                   10

<210> SEQ ID NO 12
<211> LENGTH: 8
<212> TYPE: PRT
<213> ORGANISM: Mus musculus

<400> SEQUENCE: 12

Thr Gln Ser His Thr Leu Arg Thr
1               5

<210> SEQ ID NO 13
<211> LENGTH: 10
<212> TYPE: PRT
<213> ORGANISM: Mus musculus

<400> SEQUENCE: 13

Gly Phe Thr Phe Thr Asn Tyr Tyr Ile His
1               5                   10

<210> SEQ ID NO 14
<211> LENGTH: 17
<212> TYPE: PRT
<213> ORGANISM: Mus musculus

<400> SEQUENCE: 14

Lys Ser Ser Gln Ser Leu Leu Asn Ser Arg Thr Arg Lys Asn Tyr Leu
1               5                   10                  15

Ala

<210> SEQ ID NO 15
<211> LENGTH: 17
<212> TYPE: PRT
<213> ORGANISM: Mus musculus

<400> SEQUENCE: 15

Trp Ile Ser Pro Glu Asn Gly Asn Thr Lys Tyr Asn Glu Asn Phe Gln
1               5                   10                  15

Asp

<210> SEQ ID NO 16
```

```
<211> LENGTH: 7
<212> TYPE: PRT
<213> ORGANISM: Mus musculus

<400> SEQUENCE: 16

Trp Ala Ser Ile Arg Val Ser
1               5

<210> SEQ ID NO 17
<211> LENGTH: 10
<212> TYPE: PRT
<213> ORGANISM: Mus musculus

<400> SEQUENCE: 17

Asp Gly Tyr Ser Leu Tyr Tyr Phe Asp Tyr
1               5                   10

<210> SEQ ID NO 18
<211> LENGTH: 8
<212> TYPE: PRT
<213> ORGANISM: Mus musculus

<400> SEQUENCE: 18

Thr Gln Ser His Thr Leu Arg Thr
1               5

<210> SEQ ID NO 19
<211> LENGTH: 10
<212> TYPE: PRT
<213> ORGANISM: Mus musculus

<400> SEQUENCE: 19

Gly Tyr Ser Phe Thr Asn Tyr Tyr Leu His
1               5                   10

<210> SEQ ID NO 20
<211> LENGTH: 17
<212> TYPE: PRT
<213> ORGANISM: Mus musculus

<400> SEQUENCE: 20

Lys Ser Ser Gln Ser Leu Val Asn Asn Arg Thr Arg Lys Asn Tyr Leu
1               5                   10                  15

Ala

<210> SEQ ID NO 21
<211> LENGTH: 17
<212> TYPE: PRT
<213> ORGANISM: Mus musculus

<400> SEQUENCE: 21

Trp Ile Phe Pro Glu Ser Asp Asn Thr Lys Tyr Asn Glu Lys Leu Lys
1               5                   10                  15

Gly

<210> SEQ ID NO 22
<211> LENGTH: 7
<212> TYPE: PRT
<213> ORGANISM: Mus musculus

<400> SEQUENCE: 22

Trp Ala Ser Thr Arg Glu Ser
1               5
```

```
<210> SEQ ID NO 23
<211> LENGTH: 10
<212> TYPE: PRT
<213> ORGANISM: Mus musculus

<400> SEQUENCE: 23

Asp Ser Val Gly Asn Tyr Phe Phe Asp Phe
1               5                   10

<210> SEQ ID NO 24
<211> LENGTH: 8
<212> TYPE: PRT
<213> ORGANISM: Mus musculus

<400> SEQUENCE: 24

Ala Gln Ser Phe Ile Leu Arg Thr
1               5

<210> SEQ ID NO 25
<211> LENGTH: 10
<212> TYPE: PRT
<213> ORGANISM: Mus musculus

<400> SEQUENCE: 25

Gly Tyr Thr Phe Thr Thr Tyr Ile His
1               5                   10

<210> SEQ ID NO 26
<211> LENGTH: 17
<212> TYPE: PRT
<213> ORGANISM: Mus musculus

<400> SEQUENCE: 26

Lys Ser Ser Gln Ser Leu Val Asn Asp Arg Thr Arg Lys Asn Tyr Leu
1               5                   10                  15
Ala

<210> SEQ ID NO 27
<211> LENGTH: 17
<212> TYPE: PRT
<213> ORGANISM: Mus musculus

<400> SEQUENCE: 27

Trp Ile Phe Pro Gly Ser Asp Asn Ile Lys Tyr Asn Glu Asn Phe Lys
1               5                   10                  15
Asp

<210> SEQ ID NO 28
<211> LENGTH: 7
<212> TYPE: PRT
<213> ORGANISM: Mus musculus

<400> SEQUENCE: 28

Trp Ala Ser Thr Arg Glu Ser
1               5

<210> SEQ ID NO 29
<211> LENGTH: 10
<212> TYPE: PRT
<213> ORGANISM: Mus musculus

<400> SEQUENCE: 29

Asp Ser Val Ser Arg Tyr Tyr Phe Asp Tyr
```

```
<210> SEQ ID NO 30
<211> LENGTH: 8
<212> TYPE: PRT
<213> ORGANISM: Mus musculus

<400> SEQUENCE: 30

Ala Gln Ser Phe Ile Leu Arg Thr
1               5

<210> SEQ ID NO 31
<211> LENGTH: 10
<212> TYPE: PRT
<213> ORGANISM: Mus musculus

<400> SEQUENCE: 31

Gly Phe Ser Phe Thr Asn Tyr Tyr Ile His
1               5                   10

<210> SEQ ID NO 32
<211> LENGTH: 17
<212> TYPE: PRT
<213> ORGANISM: Mus musculus

<400> SEQUENCE: 32

Lys Ser Ser Gln Ser Leu Leu Asn Asn Arg Thr Arg Lys Asn Tyr Leu
1               5                   10                  15

Ala

<210> SEQ ID NO 33
<211> LENGTH: 17
<212> TYPE: PRT
<213> ORGANISM: Mus musculus

<400> SEQUENCE: 33

Trp Ile Phe Pro Gly Thr Val Asn Thr Lys Tyr Asn Glu Lys Phe Lys
1               5                   10                  15

Gly

<210> SEQ ID NO 34
<211> LENGTH: 7
<212> TYPE: PRT
<213> ORGANISM: Mus musculus

<400> SEQUENCE: 34

Trp Ala Ser Thr Arg Glu Ser
1               5

<210> SEQ ID NO 35
<211> LENGTH: 10
<212> TYPE: PRT
<213> ORGANISM: Mus musculus

<400> SEQUENCE: 35

Asp Ser Val Gly Ile Tyr Tyr Phe Asp Phe
1               5                   10

<210> SEQ ID NO 36
<211> LENGTH: 8
<212> TYPE: PRT
<213> ORGANISM: Mus musculus

<400> SEQUENCE: 36
```

```
Thr Gln Ser Phe Ile Leu Arg Thr
1               5

<210> SEQ ID NO 37
<211> LENGTH: 10
<212> TYPE: PRT
<213> ORGANISM: Mus musculus

<400> SEQUENCE: 37

Gly Tyr Ser Phe Thr Asp Phe Tyr Thr His
1               5                   10

<210> SEQ ID NO 38
<211> LENGTH: 17
<212> TYPE: PRT
<213> ORGANISM: Mus musculus

<400> SEQUENCE: 38

Lys Ser Ser Gln Ser Leu Leu Asn Ile Arg Thr Arg Lys Asn Tyr Leu
1               5                   10                  15

Ala

<210> SEQ ID NO 39
<211> LENGTH: 17
<212> TYPE: PRT
<213> ORGANISM: Mus musculus

<400> SEQUENCE: 39

Trp Ile Phe Pro Gly Ser Asp Asn Ile Lys Tyr Asn Glu Lys Phe Lys
1               5                   10                  15

Gly

<210> SEQ ID NO 40
<211> LENGTH: 7
<212> TYPE: PRT
<213> ORGANISM: Mus musculus

<400> SEQUENCE: 40

Trp Ala Ser Thr Arg Asp Ser
1               5

<210> SEQ ID NO 41
<211> LENGTH: 10
<212> TYPE: PRT
<213> ORGANISM: Mus musculus

<400> SEQUENCE: 41

Asp Ser Val Ser Val Tyr Tyr Phe Asp Tyr
1               5                   10

<210> SEQ ID NO 42
<211> LENGTH: 8
<212> TYPE: PRT
<213> ORGANISM: Mus musculus

<400> SEQUENCE: 42

Thr Gln Ser Phe Ile Leu Arg Thr
1               5

<210> SEQ ID NO 43
<211> LENGTH: 10
<212> TYPE: PRT
<213> ORGANISM: Mus musculus
```

```
<400> SEQUENCE: 43

Gly Phe Ala Phe Thr Asp Tyr Tyr Ile His
1               5                   10

<210> SEQ ID NO 44
<211> LENGTH: 17
<212> TYPE: PRT
<213> ORGANISM: Mus musculus

<400> SEQUENCE: 44

Lys Ser Ser Gln Ser Leu Leu Asn Ser Arg Thr Arg Lys Asn Tyr Leu
1               5                   10                  15

Ala

<210> SEQ ID NO 45
<211> LENGTH: 17
<212> TYPE: PRT
<213> ORGANISM: Mus musculus

<400> SEQUENCE: 45

Trp Ile Ser Pro Gly Asn Val Asn Thr Lys Tyr Asn Glu Asn Phe Lys
1               5                   10                  15

Gly

<210> SEQ ID NO 46
<211> LENGTH: 7
<212> TYPE: PRT
<213> ORGANISM: Mus musculus

<400> SEQUENCE: 46

Trp Ala Ser Thr Arg Glu Ser
1               5

<210> SEQ ID NO 47
<211> LENGTH: 10
<212> TYPE: PRT
<213> ORGANISM: Mus musculus

<400> SEQUENCE: 47

Asp Gly Tyr Ser Leu Tyr Tyr Phe Asp Tyr
1               5                   10

<210> SEQ ID NO 48
<211> LENGTH: 8
<212> TYPE: PRT
<213> ORGANISM: Mus musculus

<400> SEQUENCE: 48

Thr Gln Ser His Thr Leu Arg Thr
1               5

<210> SEQ ID NO 49
<211> LENGTH: 25
<212> TYPE: PRT
<213> ORGANISM: Mus musculus

<400> SEQUENCE: 49

Gln Val Gln Leu Gln Gln Ser Gly Pro Glu Leu Val Lys Pro Gly Ala
1               5                   10                  15

Ser Val Lys Ile Ala Cys Lys Ala Ser
            20                  25
```

```
<210> SEQ ID NO 50
<211> LENGTH: 23
<212> TYPE: PRT
<213> ORGANISM: Mus musculus

<400> SEQUENCE: 50

Asp Ile Val Met Ser Gln Ser Pro Ser Ser Leu Ala Val Ser Ala Gly
1               5                   10                  15

Glu Lys Val Thr Met Ser Cys
            20

<210> SEQ ID NO 51
<211> LENGTH: 14
<212> TYPE: PRT
<213> ORGANISM: Mus musculus

<400> SEQUENCE: 51

Trp Val Lys Gln Arg Pro Gly Gln Gly Leu Glu Trp Ile Gly
1               5                   10

<210> SEQ ID NO 52
<211> LENGTH: 15
<212> TYPE: PRT
<213> ORGANISM: Mus musculus

<400> SEQUENCE: 52

Trp Tyr Gln Gln Lys Pro Gly Gln Ser Pro Lys Leu Leu Ile Tyr
1               5                   10                  15

<210> SEQ ID NO 53
<211> LENGTH: 32
<212> TYPE: PRT
<213> ORGANISM: Mus musculus

<400> SEQUENCE: 53

Lys Ala Thr Leu Thr Ala Asp Thr Ser Ser Thr Ala Tyr Met Gln
1               5                   10                  15

Leu Ser Ser Leu Thr Ser Glu Asp Ser Ala Val Tyr Phe Cys Ala Ile
            20                  25                  30

<210> SEQ ID NO 54
<211> LENGTH: 32
<212> TYPE: PRT
<213> ORGANISM: Mus musculus

<400> SEQUENCE: 54

Gly Val Pro Asp Arg Phe Thr Gly Ser Gly Ser Gly Thr Asp Phe Thr
1               5                   10                  15

Leu Thr Ile Asn Ser Val Gln Ala Glu Asp Leu Ala Val Tyr Tyr Cys
            20                  25                  30

<210> SEQ ID NO 55
<211> LENGTH: 11
<212> TYPE: PRT
<213> ORGANISM: Mus musculus

<400> SEQUENCE: 55

Trp Gly Gln Gly Thr Thr Leu Thr Val Ser Ser
1               5                   10

<210> SEQ ID NO 56
<211> LENGTH: 10
<212> TYPE: PRT
```

<213> ORGANISM: Mus musculus

<400> SEQUENCE: 56

Phe Gly Gly Gly Thr Lys Leu Glu Ile Lys
1               5                   10

<210> SEQ ID NO 57
<211> LENGTH: 25
<212> TYPE: PRT
<213> ORGANISM: Homo sapiens

<400> SEQUENCE: 57

Gln Val Gln Leu Val Gln Ser Gly Ala Glu Val Lys Lys Pro Gly Ser
1               5                   10                  15

Ser Val Lys Val Ser Cys Lys Ala Ser
            20                  25

<210> SEQ ID NO 58
<211> LENGTH: 23
<212> TYPE: PRT
<213> ORGANISM: Homo sapiens

<400> SEQUENCE: 58

Asp Ile Val Met Thr Gln Ser Pro Asp Ser Leu Ala Val Ser Leu Gly
1               5                   10                  15

Glu Arg Ala Thr Ile Asn Cys
            20

<210> SEQ ID NO 59
<211> LENGTH: 14
<212> TYPE: PRT
<213> ORGANISM: Homo sapiens

<400> SEQUENCE: 59

Trp Val Arg Gln Ala Pro Gly Gln Gly Leu Glu Trp Met Gly
1               5                   10

<210> SEQ ID NO 60
<211> LENGTH: 15
<212> TYPE: PRT
<213> ORGANISM: Homo sapiens

<400> SEQUENCE: 60

Trp Tyr Gln Gln Lys Pro Gly Gln Pro Pro Lys Leu Leu Ile Tyr
1               5                   10                  15

<210> SEQ ID NO 61
<211> LENGTH: 32
<212> TYPE: PRT
<213> ORGANISM: Homo sapiens

<400> SEQUENCE: 61

Arg Val Thr Ile Thr Ala Asp Lys Ser Thr Ser Thr Ala Tyr Met Glu
1               5                   10                  15

Leu Ser Ser Leu Arg Ser Glu Asp Thr Ala Val Tyr Tyr Cys Ala Ile
            20                  25                  30

<210> SEQ ID NO 62
<211> LENGTH: 32
<212> TYPE: PRT
<213> ORGANISM: Homo sapiens

<400> SEQUENCE: 62

Gly Val Pro Asp Arg Phe Ser Gly Ser Gly Ser Gly Thr Asp Phe Thr
1               5                   10                  15

Leu Thr Ile Ser Ser Leu Gln Ala Glu Asp Val Ala Val Tyr Tyr Cys
            20                  25                  30

<210> SEQ ID NO 63
<211> LENGTH: 11
<212> TYPE: PRT
<213> ORGANISM: Homo sapiens

<400> SEQUENCE: 63

Trp Gly Gln Gly Thr Leu Val Thr Val Ser Ser
1               5                   10

<210> SEQ ID NO 64
<211> LENGTH: 10
<212> TYPE: PRT
<213> ORGANISM: Homo sapiens

<400> SEQUENCE: 64

Phe Gly Gly Gly Thr Lys Val Glu Ile Lys
1               5                   10

<210> SEQ ID NO 65
<211> LENGTH: 25
<212> TYPE: PRT
<213> ORGANISM: Mus musculus

<400> SEQUENCE: 65

Gln Val Gln Leu Gln Gln Ser Gly Pro Glu Leu Val Lys Pro Gly Ala
1               5                   10                  15

Ser Val Arg Leu Ser Cys Lys Ala Ser
            20                  25

<210> SEQ ID NO 66
<211> LENGTH: 23
<212> TYPE: PRT
<213> ORGANISM: Mus musculus

<400> SEQUENCE: 66

Asp Ile Val Met Ser Gln Ser Pro Ser Ser Leu Thr Val Ser Ala Gly
1               5                   10                  15

Glu Lys Val Thr Met Ser Cys
            20

<210> SEQ ID NO 67
<211> LENGTH: 14
<212> TYPE: PRT
<213> ORGANISM: Mus musculus

<400> SEQUENCE: 67

Trp Met Lys Gln Arg Pro Gly Gln Gly Leu Glu Trp Ile Gly
1               5                   10

<210> SEQ ID NO 68
<211> LENGTH: 15
<212> TYPE: PRT
<213> ORGANISM: Mus musculus

<400> SEQUENCE: 68

Trp Tyr Gln Gln Lys Pro Gly Gln Ser Pro Lys Leu Leu Ile Tyr
1               5                   10                  15

```
<210> SEQ ID NO 69
<211> LENGTH: 32
<212> TYPE: PRT
<213> ORGANISM: Mus musculus

<400> SEQUENCE: 69

Arg Ala Thr Val Thr Ala Asp Leu Ser Ser Thr Ala Tyr Met Gln
1               5                   10                  15

Leu Ser Ser Leu Thr Ser Glu Asp Ser Ala Val Tyr Phe Cys Ala Arg
            20                  25                  30

<210> SEQ ID NO 70
<211> LENGTH: 32
<212> TYPE: PRT
<213> ORGANISM: Mus musculus

<400> SEQUENCE: 70

Gly Val Pro Asp Arg Phe Thr Gly Ser Gly Ser Gly Thr Ala Phe Thr
1               5                   10                  15

Leu Thr Ile Ser Gly Val Gln Ala Glu Asp Leu Ala Val Tyr Phe Cys
            20                  25                  30

<210> SEQ ID NO 71
<211> LENGTH: 11
<212> TYPE: PRT
<213> ORGANISM: Mus musculus

<400> SEQUENCE: 71

Trp Gly Gln Gly Thr Thr Leu Thr Val Ser Ser
1               5                   10

<210> SEQ ID NO 72
<211> LENGTH: 10
<212> TYPE: PRT
<213> ORGANISM: Mus musculus

<400> SEQUENCE: 72

Phe Gly Gly Gly Thr Lys Leu Glu Ile Lys
1               5                   10

<210> SEQ ID NO 73
<211> LENGTH: 25
<212> TYPE: PRT
<213> ORGANISM: Homo sapiens

<400> SEQUENCE: 73

Gln Val Gln Leu Val Gln Ser Gly Ala Glu Val Lys Lys Pro Gly Ser
1               5                   10                  15

Ser Val Lys Val Ser Cys Lys Ala Ser
            20                  25

<210> SEQ ID NO 74
<211> LENGTH: 23
<212> TYPE: PRT
<213> ORGANISM: Homo sapiens

<400> SEQUENCE: 74

Asp Ile Val Met Thr Gln Ser Pro Asp Ser Leu Ala Val Ser Leu Gly
1               5                   10                  15

Glu Arg Ala Thr Ile Asn Cys
            20

<210> SEQ ID NO 75
```

```
<210> SEQ ID NO 75
<211> LENGTH: 14
<212> TYPE: PRT
<213> ORGANISM: Homo sapiens

<400> SEQUENCE: 75

Trp Val Arg Gln Ala Pro Gly Gln Gly Leu Glu Trp Met Gly
1               5                   10

<210> SEQ ID NO 76
<211> LENGTH: 15
<212> TYPE: PRT
<213> ORGANISM: Homo sapiens

<400> SEQUENCE: 76

Trp Tyr Gln Gln Lys Pro Gly Gln Pro Pro Lys Leu Leu Ile Tyr
1               5                   10                  15

<210> SEQ ID NO 77
<211> LENGTH: 32
<212> TYPE: PRT
<213> ORGANISM: Homo sapiens

<400> SEQUENCE: 77

Arg Val Thr Ile Thr Ala Asp Lys Ser Thr Ser Thr Ala Tyr Met Glu
1               5                   10                  15

Leu Ser Ser Leu Arg Ser Glu Asp Thr Ala Val Tyr Tyr Cys Ala Arg
            20                  25                  30

<210> SEQ ID NO 78
<211> LENGTH: 32
<212> TYPE: PRT
<213> ORGANISM: Homo sapiens

<400> SEQUENCE: 78

Gly Val Pro Asp Arg Phe Ser Gly Ser Gly Ser Gly Thr Asp Phe Thr
1               5                   10                  15

Leu Thr Ile Ser Ser Leu Gln Ala Glu Asp Val Ala Val Tyr Tyr Cys
            20                  25                  30

<210> SEQ ID NO 79
<211> LENGTH: 11
<212> TYPE: PRT
<213> ORGANISM: Homo sapiens

<400> SEQUENCE: 79

Trp Gly Gln Gly Thr Leu Val Thr Val Ser Ser
1               5                   10

<210> SEQ ID NO 80
<211> LENGTH: 10
<212> TYPE: PRT
<213> ORGANISM: Homo sapiens

<400> SEQUENCE: 80

Phe Gly Gly Gly Thr Lys Val Glu Ile Lys
1               5                   10

<210> SEQ ID NO 81
<211> LENGTH: 119
<212> TYPE: PRT
<213> ORGANISM: Mus musculus

<400> SEQUENCE: 81

Gln Val Gln Leu Gln Gln Ser Gly Pro Glu Leu Val Lys Pro Gly Ala
```

```
 1               5                   10                  15
Ser Val Lys Ile Ala Cys Lys Ala Ser Gly Tyr Ser Phe Thr Thr Tyr
            20                  25                  30

Tyr Ile His Trp Val Lys Gln Arg Pro Gly Gln Gly Leu Glu Trp Ile
            35                  40                  45

Gly Trp Ile Phe Pro Gly Asn Asp Asn Ile Lys Tyr Ser Glu Lys Phe
    50                  55                  60

Lys Gly Lys Ala Thr Leu Thr Ala Asp Thr Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Ile Asp Ser Val Ser Ile Tyr Tyr Phe Asp Tyr Trp Gly Gln Gly
                100                 105                 110

Thr Thr Leu Thr Val Ser Ser
            115
```

<210> SEQ ID NO 82
<211> LENGTH: 357
<212> TYPE: DNA
<213> ORGANISM: Mus musculus

<400> SEQUENCE: 82

```
caggtccagc tgcagcagtc tggacctgag ctggtgaaac ctggggcttc agtgaagatt      60
gcctgcaagg cttctggcta cagcttcaca acctactata tacactgggt gaagcagagg     120
cctggacagg gacttgagtg gattggatgg attttcctg gaaatgataa tattaagtac      180
agtgagaagt tcaagggcaa ggccacactg acggcagaca cttcctccag tacagcctac     240
atgcagctca gcagcctgac atctgaggac tctgctgtct atttctgtgc tatagactcc     300
gttagtatct actactttga ctattggggc caaggcacca ctctcacagt ctcctca        357
```

<210> SEQ ID NO 83
<211> LENGTH: 112
<212> TYPE: PRT
<213> ORGANISM: Mus musculus

<400> SEQUENCE: 83

```
Asp Ile Val Met Ser Gln Ser Pro Ser Ser Leu Ala Val Ser Ala Gly
1               5                   10                  15

Glu Lys Val Thr Met Ser Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
            35                  40                  45

Ser Pro Lys Leu Leu Ile Tyr Trp Ala Ser Thr Arg Lys Ser Gly Val
    50                  55                  60

Pro Asp Arg Phe Thr Gly Ser Gly Ser Gly Thr Asp Phe Thr Leu Thr
65                  70                  75                  80

Ile Asn Ser Val Gln Ala Glu Asp Leu Ala Val Tyr Tyr Cys Thr Gln
                85                  90                  95

Ser Phe Ile Leu Arg Thr Phe Gly Gly Gly Thr Lys Leu Glu Ile Lys
                100                 105                 110
```

<210> SEQ ID NO 84
<211> LENGTH: 336
<212> TYPE: DNA
<213> ORGANISM: Mus musculus

<400> SEQUENCE: 84

```
gacattgtga tgtcacagtc tccatcctcc ctggctgtgt cagcaggaga gaaggtcact      60
atgagctgca aatccagtca gagtctgctc aacagtagaa cccgaaagaa ctacttggct     120
tggtaccagc agaaaccagg gcagtctcct aaactgctga tctactgggc atccactagg     180
aaatctgggg tccctgatcg cttcacaggc agtggatctg ggacagattt cactctcacc     240
atcaacagtg tgcaggctga agacctggca gtttattact gcacgcaatc ttttattctt     300
cggacgttcg gtggaggcac caagctggaa atcaaa                               336
```

<210> SEQ ID NO 85
<211> LENGTH: 119
<212> TYPE: PRT
<213> ORGANISM: Mus musculus

<400> SEQUENCE: 85

```
Gln Val Gln Leu Gln Gln Ser Gly Pro Glu Leu Val Lys Pro Gly Ala
1               5                  10                  15

Ser Val Arg Ile Ser Cys Lys Ala Ser Gly Phe Ala Phe Thr Asp Tyr
            20                  25                  30

Tyr Ile His Trp Val Lys Gln Arg Pro Gly Gln Gly Leu Glu Trp Ile
        35                  40                  45

Gly Trp Ile Ser Pro Gly Asn Val Asn Thr Lys Tyr Asn Glu Asn Phe
    50                  55                  60

Lys Gly Arg Ala Thr Leu Thr Ala Asp Leu Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Asp Gly Tyr Ser Leu Tyr Tyr Phe Asp Tyr Trp Gly Gln Gly
            100                 105                 110

Thr Thr Leu Thr Val Ser Ser
        115
```

<210> SEQ ID NO 86
<211> LENGTH: 357
<212> TYPE: DNA
<213> ORGANISM: Mus musculus

<400> SEQUENCE: 86

```
caggtccagc tgcagcagtc tggacctgaa ttggtgaagc ctggggcttc cgtgaggata     60
tcctgcaagg cttctggctt cgccttcaca gactactata cactgggt gaagcagagg      120 cctggacagg tcttgagtg gattggatgg atttctcctg gaaatgttaa tactaaatac     180
aatgaaaact tcaagggcag ggccacactg actgcagacc tatcctccag cacagcctac    240
atgcagctca gcagcctgac ctctgaggac tctgcggtct attttctgtgc aagagatgga    300 tattccctgt attactttga ctactggggc caaggcacca ctctcacagt ctcctca       357
```

<210> SEQ ID NO 87
<211> LENGTH: 112
<212> TYPE: PRT
<213> ORGANISM: Mus musculus

<400> SEQUENCE: 87

```
Asp Ile Val Met Ser Gln Ser Pro Ser Ser Leu Thr Val Ser Ala Gly
1               5                  10                  15

Glu Lys Val Thr Met Ser Cys Lys Ser Ser Gln Ser Leu Leu Asn Ser
            20                  25                  30
```

```
Arg Thr Arg Lys Asn Tyr Leu Ala Trp Tyr Gln Gln Lys Pro Gly Gln
            35                  40                  45
Ser Pro Lys Leu Leu Ile Tyr Trp Ala Ser Thr Arg Gln Ser Gly Val
 50                  55                  60
Pro Asp Arg Phe Thr Gly Ser Gly Ser Gly Thr Ala Phe Thr Leu Thr
 65                  70                  75                  80
Ile Ser Gly Val Gln Ala Glu Asp Leu Ala Val Tyr Phe Cys Thr Gln
                     85                  90                  95
Ser His Thr Leu Arg Thr Phe Gly Gly Gly Thr Lys Leu Glu Ile Lys
             100                 105                 110
```

<210> SEQ ID NO 88
<211> LENGTH: 336
<212> TYPE: DNA
<213> ORGANISM: Mus musculus

<400> SEQUENCE: 88

```
gacattgtga tgtcacagtc tccatcctcc ctgactgtgt cagcaggaga gaaggtcact      60
atgagctgca aatccagtca gagtctgctc aacagtagaa cccgaaagaa ctacttggct     120
tggtaccagc agaagccagg gcagtctcct aaactactaa tctactgggc atccactagg     180
caatctgggg tccctgatcg cttcacaggc agtggatctg gacagctttt cactctcacc     240
atcagcggtg tgcaggctga agacctggca gtttatttct gcacgcaatc tcatactctt     300
cggacgttcg gtggaggcac caagctggaa atcaaa                              336
```

<210> SEQ ID NO 89
<211> LENGTH: 119
<212> TYPE: PRT
<213> ORGANISM: Mus musculus

<400> SEQUENCE: 89

```
Gln Val Gln Leu Gln Gln Ser Gly Pro Glu Leu Val Lys Pro Gly Ala
 1               5                  10                  15
Ser Val Arg Ile Ser Cys Lys Thr Ser Gly Phe Thr Phe Thr Asn Tyr
             20                  25                  30
Tyr Ile His Trp Val Ile Gln Arg Pro Gly Gln Gly Leu Glu Trp Ile
         35                  40                  45
Gly Trp Ile Ser Pro Glu Asn Gly Asn Thr Lys Tyr Asn Glu Asn Phe
 50                  55                  60
Gln Asp Lys Ala Thr Leu Thr Ala Asp Ile Ser Ser Thr Ala Tyr
 65                  70                  75                  80
Met His Leu Ser Ser Leu Thr Ser Glu Asp Ser Ala Val Tyr Phe Cys
                     85                  90                  95
Ala Arg Asp Gly Tyr Ser Leu Tyr Tyr Phe Asp Tyr Trp Gly Gln Gly
             100                 105                 110
Thr Thr Leu Thr Val Ser Ser
         115
```

<210> SEQ ID NO 90
<211> LENGTH: 357
<212> TYPE: DNA
<213> ORGANISM: Mus musculus

<400> SEQUENCE: 90

```
caggtccagc tgcagcagtc tggacctgaa ttggtgaagc ctggggcttc agtgaggata      60
tcctgcaaga cttctggctt caccttcaca aactactata cactgggt gatacagagg       120
```

```
cctggacagg gacttgagtg gattggttgg atttctcctg aaaatggtaa tactaaatac      180
aatgaaaact tccaggacaa ggccacactg actgcagaca tatcgtccag cacagcctac      240
atgcacctca gcagcctgac ctctgaggac tctgcggtct atttctgtgc aagagatggg      300 tattccccttt actactttga ctactggggc caaggcacca ctctcacagt ctcctca       357
```

<210> SEQ ID NO 91
<211> LENGTH: 112
<212> TYPE: PRT
<213> ORGANISM: Mus musculus

<400> SEQUENCE: 91

```
Asp Ile Val Met Ser Gln Ser Pro Ser Ser Leu Thr Val Ser Ala Gly
1               5                   10                  15

Glu Lys Val Thr Met Ser Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Ser Pro Lys Leu Leu Ile Tyr Trp Ala Ser Ile Arg Val Ser Gly Val
    50                  55                  60

Pro Asp Arg Phe Thr Gly Ser Gly Ser Gly Thr Thr Phe Thr Leu Thr
65                  70                  75                  80

Ile Ser Gly Val Gln Ala Glu Asp Leu Ala Val Tyr Tyr Cys Thr Gln
                85                  90                  95

Ser His Thr Leu Arg Thr Phe Gly Gly Gly Thr Lys Leu Glu Ile Lys
            100                 105                 110
```

<210> SEQ ID NO 92
<211> LENGTH: 336
<212> TYPE: DNA
<213> ORGANISM: Mus musculus

<400> SEQUENCE: 92

```
gacattgtga tgtcacagtc tccatcctcc ctgactgtgt cagcaggaga gaaggtcact      60
atgagctgca aatccagtca gagtctgctc aacagtagaa cccgaaagaa ctacttggct      120
tggtaccagc agaaaccagg gcagtctcct aagctactga tctactgggc atccattagg      180
gtatctgggg tccctgatcg cttcacaggc agtggatctg gacaactttt cactctcacc      240
atcagcggtg tgcaggctga agacctggca gtttattatt gcacgcaatc tcatactctt      300
cggacgttcg gtggaggcac caagctggaa atcaaa                               336
```

<210> SEQ ID NO 93
<211> LENGTH: 119
<212> TYPE: PRT
<213> ORGANISM: Mus musculus

<400> SEQUENCE: 93

```
Gln Val Gln Leu Gln Gln Ser Gly Pro Glu Leu Val Asn Pro Gly Ala
1               5                   10                  15

Ser Val Lys Ile Ser Cys Lys Ala Ser Gly Tyr Ser Phe Thr Asn Tyr
            20                  25                  30

Tyr Leu His Trp Val Lys Gln Arg Pro Gly Gln Gly Leu Glu Trp Ile
        35                  40                  45

Gly Trp Ile Phe Pro Glu Ser Asp Asn Thr Lys Tyr Asn Glu Lys Leu
    50                  55                  60

Lys Gly Lys Ala Thr Leu Thr Ala Asp Thr Ser Ser Asp Thr Ala Tyr
65                  70                  75                  80
```

```
Met His Leu Ser Ser Leu Thr Phe Glu Asp Ser Ala Val Tyr Phe Cys
                85                  90                  95

Ala Arg Asp Ser Val Gly Asn Tyr Phe Phe Asp Phe Trp Gly Gln Gly
            100                 105                 110

Thr Thr Leu Thr Val Ser Ser
        115

<210> SEQ ID NO 94
<211> LENGTH: 357
<212> TYPE: DNA
<213> ORGANISM: Mus musculus

<400> SEQUENCE: 94
caggtccagc tgcagcagtc tggacctgag ctggtgaatc ctggggcttc agtgaagata     60
tcctgcaagg cttctggcta cagtttcaca aactactatt tacactgggt gaaacagagg    120
cctggacagg gacttgagtg gattggatgg atttttcctg aaagtgataa taccaagtac    180
aatgagaaat tgaagggcaa ggccacactg acggcagaca catcctccga tacagcctac    240
atgcacctca gcagcctgac atttgaggac tctgcagtct atttctgtgc aagagactcc    300
gttggaaact acttctttga cttctggggc caaggcacca ctctcacagt ctcctca      357

<210> SEQ ID NO 95
<211> LENGTH: 112
<212> TYPE: PRT
<213> ORGANISM: Mus musculus

<400> SEQUENCE: 95

Asp Ile Val Met Ser Gln Ser Pro Ser Ser Leu Ala Val Ser Ala Gly
1               5                   10                  15

Glu Lys Val Thr Met Arg Cys Lys Ser Ser Gln Ser Leu Val Asn Asn
            20                  25                  30

Arg Thr Arg Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Ala Gln
                85                  90                  95

Ser Phe Ile Leu Arg Thr Phe Gly Gly Gly Thr Lys Leu Glu Ile Lys
            100                 105                 110

<210> SEQ ID NO 96
<211> LENGTH: 336
<212> TYPE: DNA
<213> ORGANISM: Mus musculus

<400> SEQUENCE: 96
gacattgtga tgtcacagtc tccatcctcc ctggctgtgt cagcgggaga gaaggtcact     60
atgaggtgca atccagtca gagtctggtc aacaatagaa cccgaaagaa ctacttggca    120
tggtaccagc agaaaccagg gcagcctcct aaactattga tctactgggc atccactagg    180
gaatctgggg tccctgatcg cttcacaggc agtggatctg gacagattt cactctcacc    240 atcagcagtg tgcaggctga agacctggca gtttattact gcgcgcaatc ttttattctt    300
cggacgttcg gtggaggcac caaactggaa atcaaa                              336
```

<210> SEQ ID NO 97
<211> LENGTH: 119
<212> TYPE: PRT
<213> ORGANISM: Mus musculus

<400> SEQUENCE: 97

Gln Val Gln Leu Gln Gln Ser Gly Pro Glu Leu Val Lys Pro Gly Ser
1               5                   10                  15

Ser Val Lys Ile Ser Cys Lys Pro Ser Gly Tyr Thr Phe Thr Thr Tyr
            20                  25                  30

Tyr Ile His Trp Val Lys Gln Arg Pro Gly Gln Gly Leu Glu Trp Ile
        35                  40                  45

Gly Trp Ile Phe Pro Gly Ser Asp Asn Ile Lys Tyr Asn Glu Asn Phe
    50                  55                  60

Lys Asp Lys Ala Thr Leu Thr Ala Asp Thr Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Asp Ser Val Ser Arg Tyr Tyr Phe Asp Tyr Trp Gly Gln Gly
            100                 105                 110

Thr Ile Leu Thr Val Ser Ser
        115

<210> SEQ ID NO 98
<211> LENGTH: 357
<212> TYPE: DNA
<213> ORGANISM: Mus musculus

<400> SEQUENCE: 98
caggttcagc tgcagcagtc tggacctgag ctggtgaaac ctgggtcttc agtgaagata      60
tcctgcaaac cttctggcta caccttcaca acttactata cattgggt gaagcagagg      120 cctggacagg gacttgagtg gattggatgg attttcctg gaagtgataa tattaaatac      180
aatgagaatt tcaaggacaa ggccacactg acggcagaca catcctccag cacagcctac      240
atgcagctca gcagcctgac atctgaagac tctgcagtct atttctgtgc aagagactcc      300
gtcagtaggt actactttga ctactggggc caaggcacca ttctcacagt ttcttca      357

<210> SEQ ID NO 99
<211> LENGTH: 112
<212> TYPE: PRT
<213> ORGANISM: Mus musculus

<400> SEQUENCE: 99

Asp Ile Val Met Ser Gln Ser Pro Ser Ser Leu Ala Val Ser Ala Gly
1               5                   10                  15

Glu Lys Val Thr Met Ser Cys Lys Ser Ser Gln Ser Leu Val Asn Asp
            20                  25                  30

Arg Thr Arg Lys Asn Tyr Leu Ala Trp Tyr Gln Gln Lys Pro Gly Leu
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Ala Gln
                85                  90                  95

Ser Phe Ile Leu Arg Thr Phe Gly Gly Gly Thr Lys Leu Glu Ile Lys

<210> SEQ ID NO 100
<211> LENGTH: 336
<212> TYPE: DNA
<213> ORGANISM: Mus musculus

<400> SEQUENCE: 100
gacattgtga tgtcacagtc tccatcctcc ctggctgtgt cagcaggaga gaaggtcact    60
atgagctgca atccagtca gagtctggtc aatgatagaa cccgaaaaaa ctacttggct   120
tggtaccagc agaaaccagg gctgtctcct aaactgctga tctactgggc ttccactagg   180
gaatctgggg tccctgatcg cttcacaggc agtggatctg ggacagattt cactctcacc   240
atcagcagtg tgcaggctga agacctggct gtttattact gcgcgcaatc ttttattctt   300
cggacgttcg gtggaggcac caagctggaa atcaaa                              336

<210> SEQ ID NO 101
<211> LENGTH: 119
<212> TYPE: PRT
<213> ORGANISM: Mus musculus

<400> SEQUENCE: 101

Gln Val Gln Leu Gln Gln Ser Gly Pro Glu Leu Val Lys Pro Gly Thr
1               5                   10                  15

Ser Val Lys Ile Ser Cys Lys Ala Ser Gly Phe Ser Phe Thr Asn Tyr
            20                  25                  30

Tyr Ile His Trp Val Lys Gln Arg Pro Gly Gln Gly Pro Glu Trp Ile
        35                  40                  45

Gly Trp Ile Phe Pro Gly Thr Val Asn Thr Lys Tyr Asn Glu Lys Phe
    50                  55                  60

Lys Gly Lys Ala Thr Leu Thr Ala Asp Thr Ser Ser Asn Thr Ala Phe
65                  70                  75                  80

Met Gln Leu Ser Ser Leu Thr Ser Ala Asp Ser Ala Val Tyr Phe Cys
                85                  90                  95

Ala Arg Asp Ser Val Gly Ile Tyr Tyr Phe Asp Phe Trp Gly Leu Gly
            100                 105                 110

Thr Thr Leu Thr Val Ser Ser
        115

<210> SEQ ID NO 102
<211> LENGTH: 357
<212> TYPE: DNA
<213> ORGANISM: Mus musculus

<400> SEQUENCE: 102
caggtccagc tgcaacagtc tggacctgaa ctggtgaaac ctgggacttc agtgaagata    60
tcctgcaagg cttctggctt cagcttcaca aactactata tacactgggt gaagcagagg   120
cctggacagg gacctgagtg gattggatgg atttttcctg gaactgttaa tactaagtac   180
aatgagaagt tcaagggtaa ggccacactg acggcagaca catcctccaa tacagccttc   240
atgcagctca gcagcctgac ttctgcggac tctgcagtct atttctgtgc aagagactcc   300
gttggtatct actactttga cttctggggc ctaggcacca ctctcacagt ctcctca      357

<210> SEQ ID NO 103
<211> LENGTH: 112
<212> TYPE: PRT
<213> ORGANISM: Mus musculus

<400> SEQUENCE: 103

Asp Ile Val Met Ser Gln Ser Pro Ser Ser Leu Ala Val Ser Ala Gly
1               5                   10                  15

Glu Lys Val Thr Val Ser Cys Lys Ser Gln Ser Leu Leu Asn Asn
            20                  25                  30

Arg Thr Arg Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Thr Gln
                85                  90                  95

Ser Phe Ile Leu Arg Thr Phe Gly Gly Gly Thr Lys Leu Glu Ile Lys
            100                 105                 110

<210> SEQ ID NO 104
<211> LENGTH: 336
<212> TYPE: DNA
<213> ORGANISM: Mus musculus

<400> SEQUENCE: 104
gacattgtga tgtcacagtc tccatcctcc ctggctgtgt cagcaggaga gaaggtcact    60
gtgagttgca atccagtca gagtctgctc aacaatagaa cccgaaaaaa ctacttggct   120
tggtaccagc agaaaccagg gcagtctcct aaactactaa tctactgggc atccactagg   180
gaatctgggg tccctgatcg cttcacaggc agtggatctg gtacagattt cactctcacc   240
atcagcagtg tgcaggctga agacctggca gtttattact gcacgcaatc ttttattctt   300
cggacgttcg gtggaggcac caagctggag atcaaa                             336

<210> SEQ ID NO 105
<211> LENGTH: 119
<212> TYPE: PRT
<213> ORGANISM: Mus musculus

<400> SEQUENCE: 105

Gln Val Gln Leu Gln Gln Ser Gly Pro Glu Leu Val Lys Pro Gly Thr
1               5                   10                  15

Ser Met Lys Ile Ser Cys Lys Ala Ser Gly Tyr Ser Phe Thr Asp Phe
            20                  25                  30

Tyr Thr His Trp Val Arg Gln Arg Pro Gly Gln Gly Leu Glu Trp Ile
        35                  40                  45

Gly Trp Ile Phe Pro Gly Ser Asp Asn Ile Lys Tyr Asn Glu Lys Phe
    50                  55                  60

Lys Gly Lys Ala Thr Leu Thr Ala Asp Thr Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Asp Ser Val Ser Val Tyr Tyr Phe Asp Tyr Trp Gly Gln Gly
            100                 105                 110

Thr Thr Leu Thr Val Ser Ser
            115

<210> SEQ ID NO 106
<211> LENGTH: 357

<212> TYPE: DNA
<213> ORGANISM: Mus musculus

<400> SEQUENCE: 106
caggtccagc tgcagcagtc tggacctgag ctggtaaaac ctgggacttc aatgaaaata     60
tcctgcaagg cttctggcta cagtttcaca gacttctata cacactgggt gaggcagagg    120
cctggacagg gacttgagtg gattggatgg attttcctg gaagtgataa tattaaatac     180
aatgagaagt tcaagggcaa ggccacactg acggcagaca catcctccag cacagcctac    240
atgcagctca gcagcctgac atctgaggac tctgcagtct atttctgtgc aagagactcc    300
gttagtgtct actactttga ctattggggc caaggcacca ctctcacagt ctcctca       357

<210> SEQ ID NO 107
<211> LENGTH: 112
<212> TYPE: PRT
<213> ORGANISM: Mus musculus

<400> SEQUENCE: 107

Asp Ile Val Met Ser Gln Ser Pro Ser Ser Leu Ala Val Thr Ala Gly
1               5                   10                  15

Glu Lys Val Thr Met Ser Cys Lys Ser Ser Gln Ser Leu Leu Asn Ile
            20                  25                  30

Arg Thr Arg Lys Asn Tyr Leu Ala Trp Tyr Gln Gln Lys Pro Gly Gln
        35                  40                  45

Ser Pro Lys Leu Leu Ile Tyr Trp Ala Ser Thr Arg Asp Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Thr Gln
                85                  90                  95

Ser Phe Ile Leu Arg Thr Phe Gly Gly Gly Thr Lys Leu Glu Ile Lys
            100                 105                 110

<210> SEQ ID NO 108
<211> LENGTH: 336
<212> TYPE: DNA
<213> ORGANISM: Mus musculus

<400> SEQUENCE: 108
gacatcgtga tgtcacagtc tccatcctcc ctggctgtga cagcaggaga gaaggtcact     60
atgagctgca atccagtca gagtctgctc aacattagaa cccgaaagaa ctacttggct    120
tggtaccaac agaaaccagg gcagtctcct aaactgctga tctactgggc atccactagg    180
gactctgggg tccctgatcg cttcacaggc agtggatctg gacagattt cactctcacc    240
atcagcagtg tgcaggctga agacctggca gtttattact gcacgcaatc ttttattctt    300
cggacgttcg gtggaggcac caagctggaa atcaaa                              336

<210> SEQ ID NO 109
<211> LENGTH: 119
<212> TYPE: PRT
<213> ORGANISM: Mus musculus

<400> SEQUENCE: 109

Gln Val Gln Leu Gln Gln Ser Gly Pro Glu Leu Val Lys Pro Gly Ala
1               5                   10                  15

Ser Val Arg Ile Ser Cys Lys Ala Ser Gly Phe Ala Phe Thr Asp Tyr
            20                  25                  30

Tyr Ile His Trp Val Lys Gln Arg Pro Gly Gln Gly Leu Glu Trp Ile
            35                  40                  45

Gly Trp Ile Ser Pro Gly Asn Val Asn Thr Lys Tyr Asn Glu Asn Phe
        50                  55                  60

Lys Gly Arg Ala Thr Leu Thr Ala Asp Leu Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Asp Gly Tyr Ser Leu Tyr Tyr Phe Asp Tyr Trp Gly Gln Gly
            100                 105                 110

Thr Thr Leu Thr Val Ser Ser
        115

<210> SEQ ID NO 110
<211> LENGTH: 357
<212> TYPE: DNA
<213> ORGANISM: Mus musculus

<400> SEQUENCE: 110
caggtccagc tgcagcagtc tggacctgaa ttggtgaagc ctggggcttc cgtgaggata      60
tcctgcaagg cttctggctt cgccttcaca gactactata tacactgggt gaagcagagg     120
cctggacagg gtcttgagtg gattggatgg atttctcctg gaaatgttaa tactaaatac     180
aatgaaaact tcaagggcag ggccacactg actgcagacc tatcctccag cacagcctac     240
atgcagctca gcagcctgac ctctgaggac tctgcggtct atttctgtgc aagagatgga     300
tattccctgt attactttga ctactggggc caaggcacca ctctcacagt ctcctca        357

<210> SEQ ID NO 111
<211> LENGTH: 112
<212> TYPE: PRT
<213> ORGANISM: Mus musculus

<400> SEQUENCE: 111

Asp Ile Val Met Ser Gln Ser Pro Ser Ser Leu Thr Val Ser Ala Gly
1               5                   10                  15

Glu Lys Val Thr Met Ser Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Ala Phe Thr Leu Thr
65                  70                  75                  80

Ile Ser Gly Val Gln Ala Glu Asp Leu Ala Val Tyr Phe Cys Thr Gln
                85                  90                  95

Ser His Thr Leu Arg Thr Phe Gly Gly Gly Thr Lys Leu Glu Ile Lys
            100                 105                 110

<210> SEQ ID NO 112
<211> LENGTH: 336
<212> TYPE: DNA
<213> ORGANISM: Mus musculus

<400> SEQUENCE: 112
gacattgtga tgtcacagtc tccatcctcc ctgactgtgt cagcaggaga gaaggtcact      60
atgagctgca aatccagtca gagtctgctc aacagtagaa cccgaaagaa ctacttggct     120

```
tggtaccagc agaaaccagg gcagtctcct aagctactaa tctactgggc atccactagg    180
gaatctgggg tccctgatcg cttcacaggc agtggatctg ggacagcttt cactctcacc    240
atcagcggtg tgcaggctga agacctggca gtttatttct gcacgcaatc tcatactctt    300
cggacgttcg gtggaggcac caagctggaa atcaaa                              336
```

<210> SEQ ID NO 113
<211> LENGTH: 119
<212> TYPE: PRT
<213> ORGANISM: Artificial Sequence
<220> FEATURE:
<223> OTHER INFORMATION: Synthetic
<400> SEQUENCE: 113

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ser Phe Thr Thr Tyr
            20                  25                  30

Tyr Ile His Trp Val Arg Gln Ala Pro Gly Gln Gly Leu Glu Trp Met
        35                  40                  45

Gly Trp Ile Phe Pro Gly Asn Asp Asn Ile Lys Tyr Ser Glu Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ile Asp Ser Val Ser Ile Tyr Tyr Phe Asp Tyr Trp Gly Gln Gly
            100                 105                 110

Thr Leu Val Thr Val Ser Ser
        115
```

<210> SEQ ID NO 114
<211> LENGTH: 357
<212> TYPE: DNA
<213> ORGANISM: Artificial Sequence
<220> FEATURE:
<223> OTHER INFORMATION: Synthetic
<400> SEQUENCE: 114

```
caggtgcaac tcgtgcagtc tggagctgaa gtgaagaagc ctgggtcttc agtcaaggtc     60
agttgcaagg ccagtgggta ttccttcact acctactaca tccactgggt gcggcaggca    120
ccaggacagg gcttgagtg gatgggctgg atctttcccg gcaacgataa tattaagtac    180
agcgagaagt tcaaagggag ggtcaccatt accgccgaca atccacttc cacagcctac    240 atggagttga gcagcctgag atccgaggat acagccgtgt actactgtgc cattgacagc    300
gtgtccatct actactttga ctactggggc cagggcacac tggtcacagt gagcagc       357
```

<210> SEQ ID NO 115
<211> LENGTH: 112
<212> TYPE: PRT
<213> ORGANISM: Artificial Sequence
<220> FEATURE:
<223> OTHER INFORMATION: Synthetic
<400> SEQUENCE: 115

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
```

```
                20                  25                  30
Arg Thr Arg Lys Asn Tyr Leu Ala Trp Tyr Gln Gln Lys Pro Gly Gln
            35                  40                  45

Pro Pro Lys Leu Leu Ile Tyr Trp Ala Ser Thr Arg Lys Ser Gly Val
        50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Thr Gln
                85                  90                  95

Ser Phe Ile Leu Arg Thr Phe Gly Gly Gly Thr Lys Val Glu Ile Lys
            100                 105                 110
```

<210> SEQ ID NO 116
<211> LENGTH: 336
<212> TYPE: DNA
<213> ORGANISM: Artificial Sequence
<220> FEATURE:
<223> OTHER INFORMATION: Synthetic

<400> SEQUENCE: 116

```
gacatcgtca tgacccagtc cccagactct ttggcagtgt ctctcgggga aagagctacc      60
atcaactgca agagcagcca gtcccttctg aacagcagga ccaggaagaa ttacctcgcc     120
tggtaccaac agaagcccgg acagcctcct aagctcctga tctactgggc ctcaacccgg     180
aagagtggag tgcccgatcg ctttagcggg agcggctccg ggacagattt cacactgaca     240
atttcctccc tgcaggccga ggacgtcgcc gtgtattact gtactcagag cttcattctg     300
cggacatttg gcggcgggac taaagtggag attaag                              336
```

<210> SEQ ID NO 117
<211> LENGTH: 119
<212> TYPE: PRT
<213> ORGANISM: Artificial Sequence
<220> FEATURE:
<223> OTHER INFORMATION: Synthetic

<400> SEQUENCE: 117

```
Gln Val Gln Leu Val Gln Ser Gly Ala Glu Val Lys Lys Pro Gly Ser
1               5                   10                  15

Ser Val Lys Val Ser Cys Lys Ala Ser Gly Phe Ala Phe Thr Asp Tyr
            20                  25                  30

Tyr Ile His Trp Val Arg Gln Ala Pro Gly Gln Gly Leu Glu Trp Met
        35                  40                  45

Gly Trp Ile Ser Pro Gly Asn Val Asn Thr Lys Tyr Asn Glu Asn Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Gly Tyr Ser Leu Tyr Tyr Phe Asp Tyr Trp Gly Gln Gly
            100                 105                 110

Thr Leu Val Thr Val Ser Ser
        115
```

<210> SEQ ID NO 118
<211> LENGTH: 357
<212> TYPE: DNA
<213> ORGANISM: Artificial Sequence
<220> FEATURE:

<223> OTHER INFORMATION: Synthetic

<400> SEQUENCE: 118

```
caggtgcagc ttgtgcagtc tggggcagaa gtgaagaagc tgggtctag tgtcaaggtg      60 tcatgcaagg ctagcgggtt cgcctttact gactactaca tccactgggt gcggcaggct    120
cccggacaag ggttggagtg gatgggatgg atctccccag gcaatgtcaa cacaaagtac    180
aacgagaact tcaaaggccg cgtcaccatt accgccgaca agagcacctc cacagcctac    240
atggagctgt ccagcctcag aagcgaggac actgccgtct actactgtgc cagggatggg    300
tactccctgt attactttga ttactggggc cagggcacac tggtgacagt gagctcc      357
```

<210> SEQ ID NO 119
<211> LENGTH: 112
<212> TYPE: PRT
<213> ORGANISM: Artificial Sequence
<220> FEATURE:
<223> OTHER INFORMATION: Synthetic

<400> SEQUENCE: 119

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Arg Thr Arg Lys Asn Tyr Leu Ala Trp Tyr Gln Lys Pro Gly Gln
        35                  40                  45

Pro Pro Lys Leu Leu Ile Tyr Trp Ala Ser Thr Arg Gln Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Thr Gln
                85                  90                  95

Ser His Thr Leu Arg Thr Phe Gly Gly Gly Thr Lys Val Glu Ile Lys
            100                 105                 110
```

<210> SEQ ID NO 120
<211> LENGTH: 336
<212> TYPE: DNA
<213> ORGANISM: Artificial Sequence
<220> FEATURE:
<223> OTHER INFORMATION: Synthetic

<400> SEQUENCE: 120

```
gatatcgtga tgacccagag cccagactcc cttgctgtct ccctcggcga aagagcaacc     60
atcaactgca agagctccca aagcctgctg aactccagga ccaggaagaa ttacctggcc    120
tggtatcagc agaagcccgg ccagcctcct aagctgctca tctactgggc ctccaccggg    180
cagtctgggg tgcccgatcg gtttagtgga tctgggagcg gacagactt cacattgaca    240 attagctcac tgcaggccga ggacgtggcc gtctactact gtactcagag ccacactctc    300
cgcacattcg gcggagggac taaagtggag attaag                              336
```